(12) United States Patent
Herold et al.

(10) Patent No.: US 7,799,779 B2
(45) Date of Patent: Sep. 21, 2010

(54) SUBSTITUTED PIPERIDINES AS RENIN INHIBITORS

(75) Inventors: Peter Herold, Basel (CH); Robert Mah, Muttenz (CH); Vincenzo Tschinke, Binningen (CH); Dirk Behnke, Grenzach-Wyhlen (DE); Christiane Marti, Rheinfelden (CH); Nathalie Jotterand, Basel (CH); Stefan Stutz, Basel (CH); Michael Quirmbach, Basel (CH)

(73) Assignee: Novartis AG, Basel (CH)

( * ) Notice: Subject to any disclaimer, the term of this patent is extended or adjusted under 35 U.S.C. 154(b) by 468 days.

(21) Appl. No.: 11/887,355

(22) PCT Filed: Mar. 30, 2006

(86) PCT No.: PCT/EP2006/061190

§ 371 (c)(1),
(2), (4) Date: Sep. 28, 2007

(87) PCT Pub. No.: WO2006/103273

PCT Pub. Date: Oct. 5, 2006

(65) Prior Publication Data

US 2009/0306064 A1 Dec. 10, 2009

(30) Foreign Application Priority Data

Mar. 31, 2005 (CH) .................... 0592/05

(51) Int. Cl.
C07D 413/12 (2006.01)
C07D 413/14 (2006.01)
A61K 31/538 (2006.01)
(52) U.S. Cl. .................... 514/230.5; 544/105
(58) Field of Classification Search ............... 544/105; 514/230.5
See application file for complete search history.

(56) References Cited

U.S. PATENT DOCUMENTS 6,376,672 B1 4/2002 Breu et al.

FOREIGN PATENT DOCUMENTS

| WO | 97/09311 | 3/1997 |
|---|---|---|
| WO | 00/64873 | 11/2000 |
| WO | 02/076440 | 10/2002 |
| WO | 2004/089903 | 10/2004 |
| WO | 2005/061457 | 7/2005 |
| WO | 2006/005741 | 1/2006 |

OTHER PUBLICATIONS

International Search Report issued Jul. 11, 2006 in the International (PCT) Application of which the present application is the U.S. National Stage.
International Preliminary Report on Patentability for PCT/EP2006/061190 dated Jun. 14, 2007.

*Primary Examiner*—Kahsay T Habte
(74) *Attorney, Agent, or Firm*—Wenderoth, Lind & Ponack, L.L.P.

(57) ABSTRACT

Compounds of the general formula (I) in which the meanings of the substituents $R^1$, $R^2$, $R^3$, $R^4$, X, Z and n as stated in claim 1 have renin-inhibiting properties and can be used as medicines.

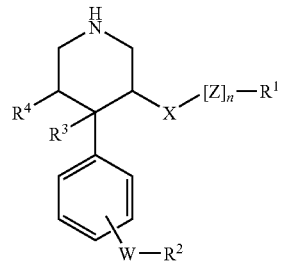

(I)

14 Claims, No Drawings

SUBSTITUTED PIPERIDINES AS RENIN INHIBITORS

FIELD OF THE INVENTION

The present invention relates to novel substituted piperidines, process for their preparation and the use of the compounds as medicines, especially as renin inhibitors.

BACKGROUND OF THE INVENTION

Piperidine derivatives for use as medicines are disclosed for example in WO 97/09311. However, especially in relation to renin inhibition, there is still a need for active ingredients of high potency. A priority in this connection is improving the pharmacokinetic properties. These properties, which are directed at better bioavailability, are for example absorption, metabolic stability, solubility or lipophilicity.

DETAILED DESCRIPTION OF THE INVENTION

The invention therefore relates to substituted piperidines of the general formula.

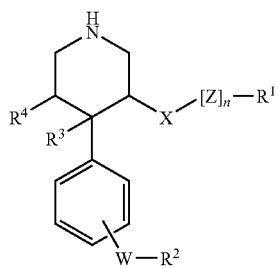

(I)

in which
(A) $R^1$ is aryl when $R^2$ is tetrazolyl or imidazolyl, each of which may be substituted $C_{1-6}$alkoxy-$C_{1-6}$alkoxy-$C_{1-6}$alkyl, $C_{1-6}$-alkoxy-$C_{1-6}$alkyl, aryloxy-$C_{1-6}$alkyl, heterocyclyloxy-$C_{1-6}$alkyl; or
(B) $R^1$ is aryl when X is —O—$CHR^5$—CO—$NR^6$—; or
(C) $R^1$ is aryl when Z is -alk—$NR^6$—, where alk is $C_{1-6}$alkylene, and n is 1; or
(D) $R^1$ is aryl which is unsubtituted by 1-4 acetamidinyl-$C_{1-6}$-alkyl, acyl-$C_{1-6}$alkoxy-$C_{1-6}$alkyl (N-acyl)-$C_{1-6}$alkoxy-$C_{1-6}$alkylamino, $C_{1-6}$alkoxy, $C_{1-6}$alkoxy-$C_{1-6}$alkoxy, $C_{1-6}$alkoxy-$C_{1-6}$alkoxy-$C_{1-6}$alkyl, $C_{1-6}$alkoxy-$C_{1-6}$ alkyl, (N—$C_{1-6}$alkoxy)-$C_{1-6}$alkylaminocarbonyl-$C_{1-6}$ alkoxy, (N—$C_{1-6}$alkoxy)-$C_{1-6}$alkylaminocarbonyl-$C_{1-6}$ alkyl, $C_{1-6}$alkoxy-$C_{1-6}$alkyl-carbamoyl, $C_{1-6}$-alkoxy-$C_{1-6}$ alkylcarbonyl, $C_{1-6}$alkoxy-$C_{1-6}$alkylcarbonylamino, 1-$C_{1-6}$alkoxy-$C_{1-6}$-alkylimidazol-2-yl, 2-$C_{1-6}$-alkoxy-$C_{1-6}$-alkyl-4-oxoimidazol-1-yl, 1-$C_{1-6}$alkoxy-$C_{1-6}$-alkyltetrazol-5-yl, 5-$C_{1-6}$-alkoxy-$C_{1-6}$-alkyltetrazol-1-yl, 6-alkoxyamino-carbonyl-$C_{1-6}$alkoxy, $C_{1-6}$-alkoxyaminocarbonyl-$C_{1-6}$alkyl, $C_{1-6}$alkoxycarbonyl, $C_{1-6}$alkoxycarbonyl-$C_{1-6}$alkoxy, $C_{1-6}$alkoxycarbonyl-$C_{1-6}$alkyl, $C_{1-6}$alkoxycarbonylamino-$C_{1-6}$alkoxy, $C_{1-6}$-alkoxycarbonylamino-$C_{1-6}$alkyl, $C_{1-6}$alkyl, (N—$C_{1-6}$alkyl)-$C_{1-6}$alkoxy-$C_{1-6}$alkylcarbamoyl, (N—$C_{1-6}$-alkyl)-$C_{1-6}$ alkoxy-$C_{1-6}$alkylcarbonylamino, (N—$C_{1-6}$alkyl)-$C_{1-6}$ alkoxy-carbonylamino, (N—$C_{1-6}$alkyl)-$C_{0-6}$ alkylcarbonylamino-$C_{1-6}$alkoxy, (N—$C_{1-6}$alkyl)-$C_{0-6}$ alkylcarbonylamino-$C_{1-6}$ alkyl, (N—$C_{1-6}$alkyl)-$C_{1-6}$alkysulphonylamino-$C_{1-6}$ alkoxy, (N—$C_{1-6}$alkyl)-$C_{1-6}$alkylsulphonylamino-$C_{1-6}$ alkyl, $C_{1-6}$alkylamidinyl, $C_{1-6}$alkylaminocarbonyl-$C_{1-6}$ alkoxy, di-$C_{1-6}$alkylaminocarbonyl-$C_{1-6}$alkoxy, $C_{1-6}$alkylaminocarbonyl-$C_{1-6}$alkoxy-$C_{1-6}$alkyl, $C_{1-6}$alkylaminocarbonyl-$C_{1-6}$alkyl, $C_{1-6}$alkylaminocarbonylamino-$C_{1-6}$ alkoxy, $C_{1-6}$alkylaminocarbonylamino-$C_{1-6}$alkyl, di-$C_{1-6}$-alkylaminocarbonyl-$C_{1-6}$-alkyl, $C_{1-6}$alkylamino-$C_{2-6}$alkoxy, di-$C_{1-6}$alkylamino-$C_{2-6}$alkoxy, $C_{1-6}$alkylamino-$C_{1-6}$alkyl, di-$C_{1-6}$alkylamino-$C_{1-6}$alkyl, $C_{1-6}$alkylcarbamoyl, di-$C_{1-6}$alkylcarbamoyl, $C_{0-6}$alkylcarbonylamino-$C_{1-6}$alkoxy, $C_{0-6}$alkylcarbonylamino, $C_{0-6}$alkylcarbonylamino-$C_{1-6}$-alkyl, $C_{1-6}$alkylcarbonyloxy-$C_{1-6}$alkoxy, $C_{1-6}$alkylcarbonyl-oxy-$C_{1-6}$alkyl, $C_{1-6}$alkylsulphonyl, $C_{1-6}$alkylsulphonyl-$C_{1-6}$alkoxy, $C_{1-6}$alkylsulphonyl-$C_{1-6}$alkyl, $C_{1-6}$alkylsulphonylamino-$C_{1-6}$alkoxy, $C_{1-6}$alkylsulphonylamino-$C_{1-6}$alkyl, carbamoyl, carbamoyl-$C_{1-6}$alkoxy, carbamoyl-$C_{1-6}$alkyl, carboxy-$C_{1-6}$alkoxy, carboxy-$C_{1-6}$alkoxy-$C_{1-6}$alkyl, carboxy-$C_{1-6}$alkyl, cyano, cyano-$C_{1-6}$alkoxy, cyano-$C_{1-6}$ alkyl, $C_{3-6}$cycloalkylcarbonylamino-$C_{1-6}$alkoxy, $C_{3-6}$cycloalkylcarbonylamino-$C_{1-6}$alkyl, cyclopropyl-$C_{1-6}$alkyl, O,N-dimethylhydroxylamino-$C_{1-6}$alkyl, halogen, hydroxy-$C_{2-6}$alkoxy-$C_{1-6}$alkoxy, hydroxy-$C_{2-6}$alkoxy-$C_{1-6}$ alkyl, hydroxy-$C_{1-6}$alkyl, (N-hydroxy)-$C_{1-6}$alkylaminocarbonyl-$C_{1-6}$alkoxy, (N-hydroxy)-$C_{1-6}$alkylaminocarbonyl-$C_{1-6}$alkyl, (N-hydroxy)aminocarbonyl-$C_{1-6}$alkoxy, (N-hydroxy)aminocarbonyl-$C_{1-6}$alkyl, 2-oxooxazolidinyl-$C_{1-6}$alkoxy, 2-oxooxazolidinyl-$C_{1-6}$alkyl, O-methyloximyl-$C_{1-6}$alkyl or trifluoromethyl; or
(E) $R^1$ is aryl which is substituted by 3-acetamidomethylpyrrolidinyl, 3-$C_{1-6}$alkoxy-$C_{1-6}$alkyl-pyrrolidinyl, 3,4-dihydroxypyrrolidinyl, 2,6-dimethylmorpholinyl, 3,5-dimethyl-morpholinyl, dioxanyl, dioxolanyl, 4,4-dioxothiomorpholinyl, dithianyl, dithiolanyl, 2-hydroxymethylpyrrolidinyl, 4-hydroxypiperidinyl, 3-hydroxypyrrolidinyl, imidazolyl-alkoxy, imidazolylalkyl, 2-methylimidazolyalkoxy, 2-methylimidazolylalky, 3methyl-[1,2,4]-oxadiazol-5-ylalkoxy, 5-methyl-[1,2,4]-oxadiazol-3-ylalkoxy, 3-methyl-[1,2,4]-oxadiazol-5-ylalky, 5-methyl-[1,2,4]-oxadiazol-3-ylalky, 4-methylpiperazinyl, 5-methyltetrazol-1-ylalkoxy, 5-methyltetrazol-1-ylalkyl, morpholinyl, [1,2,4]-oxadiazol-5-ylalkoxy, [1,2,4]-oxadiazol,-5-ylalkyl, oxazol-4-ylalkoxy, oxazol-4ylalkyl, 2-oxo-[1,3]oxazinyl, 2-oxooxazolidinyl, 2-oxoimidazolidinyl, 2-oxopyrrolidinyl, 4-oxopiperidinyl, 2-oxopyrrolidinylalkoxy, 2-oxopyrrlidinyalkyl, 2-oxotetrahydropyrimidinyl, 4-oxothiomorpholinyl, piperazinyl, piperidinyl, pyrrolidinyl, pyrrolyl, [1,2,4]-triazol-1 -ylalkoxy, [1,2,4]-triazol-4-ylalkoxy [1,2,4]-triazol-1ylalkyl, [1,2,4]-triazol-4-ylalkyl, tetrazol-1-ylalkoxy, tetrazol-2-ylalkoxy, tetrazol-5-ylalkoxy, tetrazol-1-ylalkyl, tetrazol-2-ylalkyl, tetrazol-5-ylalkyl, thiazol-4-ylalkoxy, thiazol-4-ylalkyl, thiomorpholinyl; or
(F) $R^1$ is heterocyclyl optionally substituted as indicated under (D) or (E), in particular benzo[1,3]dioxolyl, benzofuranyl, benzooxazolyl, dihydrobenzofuranyl, 3,4-dihydro-2H-benzo[1,4]oxazinyl, dihydro-3H-benzo[1,4]oxazinyl, dihydro-2H-benzo[1,4]thiazinyl, 2,3-dihydroindolyl, dihydro-1H-pyrido[2,3-b][1,4]oxazinyl, 1,1-dioxodihydro-2H-benzo[1,4]thiazinyl, indazolyl, indolyl, [1,5]naphthyridyl, oxazolyl, 2-oxoazepanyl, 3-oxo-4H-benzo[1,4]oxazinyl, 2-oxobenzooxazolyl, 3-oxo-4H-benzo[1,4]thiazinyl, 2-oxodihydrobenzo[e][1,4]diazepinyl, 2-oxodihydrobenzo-[d][1,3]oxazinyl, 2-oxodihydo-1H-quinazolinyl, 4-oxodihydroimidazolyl, 2-oxo-1,3-dihydroindolyl, 1-oxo-3H-isobenzofuranyl, 2-oxopiperidinyl 2-oxo-1H-pyrido[2,3-b][1,4]oxazinyl, 1-oxopyridyl, 2-oxotetrahydrobenzo[e][1,4]diazepinyl, 4-oxo-3H-thieno[2,3-d]pyrimidinyl, 5-oxo-4H-[1,2,4]triazinyl, phthalazinyl pyrazoly, 1H-pyrrolizinyl, 1H-pytrolo[2,3-b]pyridyl, pyrrolyl, tetrahydroquinoxalinyl, tetrahydro-pyranyl, triazinyl or 1,1,3-trioxodihydro-2H-1lambda*6*-benzo[1,4]thiazinyl;

$R^2$ is phenyl or heterocycly which is linked via a C atom, each of which radicals may be substituted by 1-4$C_{1-6}$alkanoyl, $C_{1-6}$alkoxy, $C_{1-6}$alkoxy-$C_{1-6}$alkoxy, $C_{1-6}$alkoxy-$C_{1-6}$alkyl, $C_{1-6}$alkoxycarbonylamino, $C_{1-6}$alkyl, $C_{0-6}$alkylcarbonylamino, $C_{1-6}$alkylenedioxy, $C_{1-6}$alkylsulphanyl, $C_{1-6}$alkylsulphonyl, optionally N-mono- or N,N-di-$C_{1-6}$-alkylated amino, optionally N-mono- or N,N-di-$C_{1-6}$alkylated carbamoyl, optionally esterified carboxy cyano, cyano-$C_{1-6}$alkyl, $C_{3-8}$cycloalkoxy, $C_{3-8}$cycloalkyl, halogen, hydroxy-$C_{1-6}$alkyl, nitro, oxide-oxo trifluoromethyl, trifluoromethoxy or optionally N—$C_{1-6}$-alkylated piperazinyl-$C_{1-6}$alkyl;

$R^3$ is hydrogen, hydroxy, $C_{1-6}$alkoxy or $C_{2-6}$alkenyloxy;

$R^4$ is $C_{1-6}$alkoXy, $C_{1-6}$alkoxy-$C_{1-6}$alkoxy, optionally N-mono- or N,N-di-$C_{1-6}$-alkylated amino-$C_{1-6}$alkoxy, optionally N—$C_{1-6}$-alkylated $C_{1-6}$alkoxycarbonylamino-$C_{1-6}$ alkoxy, optionally N—$C_{1-6}$-alkylated $C_{1-6}$alkcaronylamino-$C_{1-6}$alkoxy, $C_{3-8}$cycloalkyloxy, $C_{3-8}$cycloalkyloxy-$C_{1-6}$alkoxy hydroxy, hydroxy-$C_{2-6}$alkoxy, hydroxy-$C_{2-6}$-alkoxy-$C_{1-6}$alkoxy, heterocyclyl-$C_{1-6}$alkoxy, hetero-cycloxy, heterocyclyloxy-$C_{1-6}$alkoxy or oxo;

$R^5$ is acyl, $C_{2-8}$alkenyl $C_{1-6}$alkyl, aryl-$C_{1-6}$alkyl or hydrogen;

$R^6$ is acyl, $C_{1-6}$alkoxy-$C_{1-6}$alkyl, $C_{1-6}$alkyl or aryl-$C_{1-6}$alkyl or hydrogen;

$R^7$ is $C_{1-6}$, alkoxycarbonyl-$C_{1-6}$alkyl, $C_{1-6}$alkyl, carboxy-$C_{1-6}$alkyl or hydrogen;

W is oxygen, methylene or difluoromethylene;

X is a bond, oxygen or sulphur, where the bond originating from an oxygen or sulphur atom leads to a saturated C atom of group Z or $R^1$, or a group >CH—$R^5$, >$CHOR^6$, —O—CO—, >CO, >C=$NOR^7$, —O—$CHR^5$— or —O—$CHR^5$—CO—$NR^6$—;

Z is $C_{1-6}$alkylene, $C_{2-8}$alkenylene, hydroxy-$C_{1-6}$alkylidene, —O—, —S—, —O-alk , —S-alk-, -alk-O—, -alk-S— or -alk-$NR^6$—, where alk is $C_{1-6}$alkylene; and where
  (a) if Z is —O-alk- or —S-alk-, then X is —$CHR^5$—; and
  (b) if X is a bond, then Z is $C_{2-8}$alkenylene, -alk-O— or -alk-S—;

n is 1 or if X is —O—CO— or —O—$CHR^5$—CO—$NR^6$—, 0 or 1;

and their salts, preferably their pharmaceutically acceptable salts.

Examples of $C_{1-6}$alkyl and alkoxy radicals are methyl, ethyl, n-propyl, isopropyl, n-butyl, isobutyl, sec-butyl, pentyl, hexyl, and methoxy, ethoxy, propoxy, isopropoxy, butoxy, isobutoxy, sec-butoxy and tert-butoxy. $C_{1-6}$Akylenedioxy radicals are preferably methylenedioxy, ethylenedioxy and propylenedioxy. Examples of $C_{1-6}$alkanoyl radicals are acetyl, propionyl and butyryl. Cycloalkyl is a saturated, cyclic hydrocarbon radical having 3 to 12 carbon atoms, for example cyclopropyl, cyclobutyl, cyclopentyl, cyclohexyl, cycloheptyl, bicyclo[2.2.1]heptyl, cyclooctyl, bicyclo[2.2.2]octyl and adamantyl $C_{1-8}$Alkylene radicals are, for example, methylene, ethylene, propylene, 2-methylpropylene, tetra-, penta- and hexamethylene, $C_{2-8}$alkenylene radicals are, for example, vinylene and propenylene, $C_{2-8}$alkynylene radical is, for example, ethynylene, acyl radicals are alkanoyl radicals, preferably $C_{1-6}$alkanoyl radicals, or aroyl radicals such as benzoyl. Aryl refers to mono- or polynuclear aromatic radicals which may be substituted one or more times, such as, for example, phenyl, substituted phenyl, naphthyl, substituted naphthyl, tetrahydronaphthyl or substituted tetrahydronaphthyl. Examples of substituents on such aryl radicals are $C_{1-6}$alkyl, trifluoromethyl, nitro, amino, $C_{2-8}$alkenyl, $C_{1-6}$alkoxy, $C_{1-6}$alkylcarbonyloxy, hydroxy, halogen, cyano, carbamoyl, carboxy and $C_{1-6}$alkylenedioxy, and optionally halogen-, $C_{1-6}$alkyl-, $C_{1-6}$alkoxy- or dihydroxy-$C_{1-6}$alkylaminocarbonyl-substituted phenyl, phenoxy, phenylthio, phenyl-$C_{1-6}$alkyl or phenyl-$C_{1-6}$alkoxy. Further examples of substituents on aryl or heterocyclyl radicals are $C_{1-6}$alkoxycarbonylphenyl, hydroxy-$C_{1-6}$alkylphenyl, benzyloxy, pyridylcarbonyl-amino-$C_{1-6}$alkyl, $C_{2-6}$alkenyloxy, $C_{1-6}$alkoxy-$C_{1-6}$alkoxy, $C_{1-6}$alkoxy-$C_{1-6}$alkoxy-$C_{1-6}$alkoxy-$C_{1-6}$alkyl, methoxybenzyloxy, hydroxybenzyloxy, phenethyloxy, methylenebdioxybeenzyloxy, dioxolanyl-$C_{1-6}$alkoxy, cyclopropyl-$C_{1-6}$alkyl, cyclopropyl-$C_{1-6}$alkoxy, hydroxy-$C_{2-6}$ alkoxy, carbamoyloxy-$C_{1-6}$alkoxy, pyridylcarbamoyloxy-$C_{1-6}$alkoxy, benzoyloxy-$C_{1-6}$alkoxy, $C_{1-6}$alkoxycarbonyl, $C_{0-6}$alkylcarbonylamino, $C_{0-6}$alkylcarbonylamino-$C_{1-6}$alkyl, $C_{0-6}$alkylcarbonylamino-$C_{1-6}$alkoxy, (N-$C_{1-6}$alkyl)-$C_{0-6}$alkylcarbonylamino-$C_{1-6}$alkyl, (N—$C_{1-6}$alkyl)-$C_{0-6}$alkylcarbonylamino-$C_{1-6}$alkoxy, $C_{3-6}$cycloalkylcarbonylamino-$C_{1-6}$alkyl, $C_{3-6}$cycloalkylcarbonylamino-$C_{1-6}$alkoxy, $C_{1-6}$alkoxy-$C_{1-6}$alkyl, hydroxy-$C_{1-6}$alkyl, hydroxy-$C_{2-6}$alkoxy-$C_{1-6}$alkyl, hydroxy-$C_{2-6}$alkoxy-$C_{1-6}$alkoxy, $C_{1-6}$alkoxycarbonylamino-$C_{1-6}$alkyl, $C_{1-6}$alkoxycarbonylamino-$C_{1-6}$alkoxy, $C_{1-6}$alkyl-aminocarbonylamino-$C_{1-6}$alkyl, $C_{1-6}$alkylaminocarbonylamino-$C_{1-6}$alkoxy, $C_{1-6}$alkylamino-carbonyl-$C_{1-6}$alkyl, $C_{1-6}$alkylaminocarbonyl-$C_{1-6}$alkoxy, $C_{1-6}$alkylaminocarbonyl-$C_{1-6}$alkoxy-$C_{1-6}$alkyl, di-$C_{1-6}$alkylaminocarbonyl-$C_{1-6}$alkyl, di-$C_{1-6}$alkylaminocarbonyl-$C_{1-6}$alkoxy, $C_{1-6}$alkylcarbonyloxy-$C_{1-6}$alkyl, $C_{1-6}$alkylcarbonyloxy-$C_{1-6}$alkoxy, cyano-$C_{1-6}$alkyl, cyano-$C_{1-6}$alkoxy, 2-oxooxazolidinyl-$C_{1-6}$alkyl, 2-oxooxazolidinyl-$C_{1-6}$alkoxy, $C_{1-6}$alkoxycarbonyl-$C_{1-6}$alkyl, $C_{1-6}$alkoxycarbonyl-$C_{1-6}$alkoxy, $C_{1-6}$alkylsulphonylamino-$C_{1-6}$alkyl, $C_{1-6}$alkylsulphonyl-amino-$C_{1-6}$alkoxy, (N—$C_{1-6}$alkyl)-$C_{1-6}$alkylsulphonylamino-$C_{1-6}$alkyl, (N-$C_{1-6}$alkyl)-$C_{1-6}$alkylsulphonylamino-$C_{1-6}$alkoxy, $C_{1-6}$alkylamino-$C_{1-6}$alkyl, $C_{1-6}$alkylamino-$C_{2-6}$alkoxy, di-$C_{1-6}$alkylamino-$C_{1-6}$alkyl, di-$C_{1-6}$alkylamino-$C_{2-6}$alkoxy, $C_{1-6}$alkylsulphonyl-$C_{1-6}$alkyl, $C_{1-6}$alkylsulphonyl-$C_{1-6}$alkoxy, carboxy-$C_{1-6}$alkyl, carboxy-$C_{1-6}$alkoxy, carboxy-$C_{1-6}$alkoxy-$C_{1-6}$alkoxy, $C_{1-6}$alkoxy-$C_{1-6}$alkylcarbonyl, acyl-$C_{1-6}$alkoxy-$C_{1-6}$alkyl, (N—$C_{1-6}$alkyl)-$C_{1-6}$alkoxy-carbonylamino, (N-hydroxy)-$C_{1-6}$alkylaminocarbonyl-$C_{1-6}$alkyl, (N-hydroxy)-$C_{1-6}$alkylamino-carbonyl-$C_{1-6}$alkoxy, (N-hydroxy)aminocarbonyl-$C_{1-6}$alkyl, (N-hydroxy)aminocarbonyl-$C_{1-6}$alkoxy, $C_{1-6}$alkoxyaminocarbonyl-$C_{1-6}$alkyl, 6-alkoxyaminocarbonyl-$C_{1-6}$alkoxy, (N—$C_{1-6}$alkoxy)-$C_{1-6}$alkylaminocarbonyl-$C_{1-6}$alkyl, (N—$C_{1-6}$alkoxy)-$C_{1-6}$alkylaminocarbonyl-$C_{1-6}$alkoxy, (N-acyl)-$C_{1-6}$alkoxy-$C_{1-6}$alkylamino, $C_{1-6}$alkoxy-$C_{1-6}$alkylcarbamoyl, (N—$C_{1-6}$alkyl)-$C_{1-6}$alkoxy-$C_{1-6}$ alkylcarbamoyl, $C_{1-6}$alkoxy-$C_{1-6}$alkylcarbonyl, $C_{1-6}$alkoxy-$C_{1-6}$alkylcarbonyl-amino, (N-$C_{1-6}$alkyl)-$C_{1-6}$ alkoxy-$C_{1-6}$ alkylcarbonylamino, 1-$C_{1-6}$alkoxy-$C_{1-6}$alkylimidazol-2-yl, 1-$C_{1-6}$ alkoxy-$C_{1-6}$alkytetrazol-5-yl, 5-$C_{1-6}$alkoxy-$C_{1-6}$alkyltetraxol-1yl, 2-$C_{1-6}$alkoxy-$C_{1-6}$alkyl-4 -oxoimidazol-1-yl, carbamoyl-$C_{1-6}$alkyl, carbamoyl-$C_{1-6}$alkoxy, $C_{1-6}$alkylcarbamoyl, di-$C_{1-6}$alkyl-carbamoyl, $C_{1-6}$alkylsulphonyl, $C_{1-6}$alkylamidinyl, acetamidinyl-$C_{1-6}$alkyl, O-methyloximyl-$C_{1-6}$alkyl, O,N-dimethylhydroxyamino-$C_{1-6}$alkyl, $C_{3-6}$cycloalkyl-$C_{1-6}$alkanoyl, aryl-$C_{1-6}$alkanoyl, heterocyclyl-$C_{1-6}$alkanoyl; and optionally halogen-, $C_{1-6}$alkyl-, $C_{1-6}$alkoxy- or dihydroxy-$C_{1-6}$alkylaminocarbonyl-substituted pyridyl, pyridyloxy, pyridythio, pyridylamino, pyridyl-$C_{1-6}$alkyl, pyridyl-$C_{1-6}$ alkoxy, pyrimidinyl, pyrimidinyloxy, pyrimidinylthio, pyrimidinylamino, pyrimidinyl-$C_{1-6}$alkyl, pyrimidinyl-$C_{1-6}$ alkoxy, thienyl, thienyl-$C_{1-6}$alkyl, thienyl-$C_{1-6}$alkoxy, furyl, furyl-$C_{1-6}$alkyl, furyl-$C_{1-6}$alkoxy.

The term heterocyclyl refers to mono-, bi or tricyclic, saturated and unsaturated heterocyclic radicals having 1 to 4 nitrogen and/or 1 or 2 sulphur or oxygen atoms, which may be substituted one or more times, in particular by (in the case of unsaturated heterocyclyl radicals) alkyl, hydroxy, alkoxy, nitro or halogen or by substituents as defined above for aryl radicals, or (in the case of saturated heterocyclyl radicals) may be substituted by alkyl or alkoxy. Examples of heterocyclyl radicals are pyridyl, thienyl, pyrazinyl, triazolyl, imidazolyl, benzothiazolyl, furyl, pyranyl, tetrahydropyranyl, azetidihyl, pyrimidintyl, morpholinyl, quinazolinyl, quinolyl, quinoxalinyl, isoquinolyl, benzo (b) thienyl, isobenzofuranyl, benzoimidazolyl, 2-oxobenzimidazolyl, oxazolyl, thiazolyl, indolyl, pyrrolyl, 2-oxodihydro-benzo-[d][1,3]oxazinyl, 4-oxodihydroimidazolyl, 5oxo-4H-[1,2,4]triazinyl, 3-oxo-4H-benzo[1,4]thiazinyl, tetrahydroquinoxalinyl, 2-oxodihydro-1H-quinazolinyl, 1,1,3-trioxo-dihydro-2H-1lambda*6*-benzo[1,4]thiazinyl, 1-oxopyridyl, 3,4-dihydro-2H-benzo[1,4]oxazinyl, dihydro-3H-benzo[1,4]oxazinyl, 2-oxotetrahydrobenzo[e][1,4]diazepinyl, 2-oxodihydro-benzo[e][1,4]diazpinyl, 1H-pyrrolizinyl, phthalazinyl, phthalazinyl, 1-oxo-3H-isobenzofuranyl, 4oxo-3H-thieno[2,3-d]pyrimidinyl, 3-oxo-4H-benzo[1,4]oxazinyl, [1,5]naphthyridyl, [1,7]naphthyridyl, [1,8]naphthyridyl, dihydro-2H-benzo[1,4]thiazinyl, 1,1-dioxodihydro-2H-benzo[1,4]thiazinyl, 2-oxo-1H-pyrido[2,3-b][1,4]oxazinyl, dihydro-1H-pyrido[2,3-b][1,4]oxazinyl, 1H-pyrrolo[2,3-b]pyridyl, 3H-imidazo[4,5-c]pyridyl, 1H-pyrrolo[3,2-c]pyridyl, benzo[1,3]dioxolyl, benzooxazolyl, 2-oxobenzooxazolyl, 2-oxo-1,3-dihydroindolyl, 2,3-dihydroindolyl, spiro[cyclopropyl-1,3-(2-oxo-1,3dihydroindolyl), indazolyl or benzofuranyl. Examples of substituted heterocyclyl radicals are nitrobenzothiazolyl, phenyltetrazolyl, phenyloxadiazolyl, phenylpiperidinyl, phenypiperazinyl, phenylpyrrolidinyl, thienyloxadiazolyl, furanyloxadiazolyl, benzyloxadiazolyl or phenyloxazolyl. Examples of saturated heterocyclyl radicals are dioxolanyl, dioxanyl, dithiolanyl, dithianyl, pyrrolidinyl, piperidinyl, piperazinyl, 4-methyl-piperazinyl, morpholinyl, thiomorpholinyl, 2-hydroxymethylpyrrolidinyl, 3-hydroxypyrrolidinyl, 3,4-dihydroxypyrrolidinyl, 4-hydroxypiperidinyl, 4oxopiperidinyl, 3,5-dimethylmorpholinyl, 4,4-dioxothiomorpholinyl, 4-oxothiomorpholinyl, 2,6-dimethylmorpholinyl, tetrahydropyranyl, 2-oxoimidazolidinyl, 2-oxooxazolidinyl, 2-oxopiperidinyl, 2-oxopyrrolidinyl, 2-oxo-[1,3]oxazinyl, 2-oxoazepanyl, 2 oxotetrahydropyrimidinyl and the like.

In the case of $R^1$, the aryl, aroyl and heterocyclyl radicals may additionally be substituted by heterocyclylalkyl, heterocyclylalkoxy, heterocyclylalkoxyalkyl or heterocyclyl such as, for example, piperidinoalkyl, piperidinoalkoxy, piperidinoalkoxyalkyl, morpholinoalkyl, morpholinoalkoxy, morpholinoalkoxyalkyl, piperazinoalkyl, piperazinoalkoxy, piperainoalkoxyalkyl, [1,2,4]-triazol-1-ylalkyl, [1,2,4]-triazol-1ylalkoxy, [1,2,4]-triazol-4-ylalkyl, [1,2,4]-triazol-4-ylalkoxy, [1,2,4]-oxadiazol-5-1ylalkyl, [1,2,4]-oxadiazol-5-ylalkoxy, 3-methyl-[1,2,4]-oxadiazol-5-ylalkyl, 3-methyl-[1,2,4]-oxadiazol-5-ylalkoxy, 5-methyl-[1,2,4]-oxadiazol-3-ylalkyl, 5-methyl-[1,2,4]-oxadiazol-3-ylalkoxy, tetrazol-1-ylalkyl, tetrazol-1-ylalkoxy, tetrazol-2-ylalkyl, tetrazol-2-ylalkoxy, tetrazol-5-ylalkyl, tetrazol-5-ylalkoxy, 5-methyl-tetrazol-1-ylalkyl, 5-methyltetrazol-1-ylalkoxy, thiazol-4ylalkyl, thiazol-4-ylalkoxy, oxazol-4-ylalkyl, oxazol-4-ylalkoxy, 2-oxopyrrolidinylalkyl, 2-oxopyrrolidinylalkoxy, imidazolylalkyl, imidazolylalkoxy, 2-methylimidazolylalkyl, 2-methylimidazolylalkoxy or N-methylpiperazinoalkyl, N-methylpiperazinoalkoxy, N-methylpiperazinoalkoxyalkyl, and alkylaminoalkyl, alkylaminoalkoxy, alkyaminoalkoxyalkyl, mono- and polyhydroxyalkyl, -alkoxy, -alkoxyalkyl and -alkoxyalkoxy, carbamoylalkyloxy, $C_{1-6}$alkoxy, amino-$C_{1-6}$alkoxy, hydroxy-$C_{2-6}$alkoxy, dioxolanyl, dioxanyl, dithiolanyl, dithianyl, pyrrolidinyl, piperidinyl, piperazinyl, pyrroly, 4-methylpiperazinyl, morpholinyl, thiomorpholinyl, 2-hydroxymethypyrrolinyl, 3-hydroxy-pyrrolidinyl, 3,4-dihydroxypyrrolidinyl,3-acetamidomethylpyrrolidinyl, 3-$C_{1-6}$alkoxy,-$C_{1-6}$alkylpyrrolidinyl, 4-hyroxypiperdinyl, 4-oxopiperidinyl, 3,5-dimethylmorpholinyl, 4,4-dioxothio-morpholinyl, 4-oxothiomorpholinyl, 2,6-dimethylmorpholinyl, 2-oxoimidazolidinyl, 2-oxo-oxazolidinyl, 2-oxopyrrolidinyl, 2-oxo-[1,3]oxazinyl, 2-oxotetrahydropyrimidinyl and the like or by the radical —O—$CH_2CH(OH)CH_2NRx$, where NRx is a mono- or di-$C_{1-6}$alkylamino, piperidino, morpholino, piperazino or N-methylpiperazino radical.

The term polyhydroxyalky refers to $C_{1-7}$alkyl radicals which may be substituted by 2-6hydroxy groups, such as, for example, glyceryl, arabityl, sorbityl etc.

The compounds of the formula (I) have at least two asymmetric carbon atoms and can therefore exist in the form of optically pure diastereomers, mixtures of diastereomers, diastereomeric racemates, mixtures of diastereomeric racemates or as meso compounds. The invention includes all these forms.

Mixtures of diastereomers, diastereomeric racemates or mixtures of diastereomeric racedmate's can be fractionated conventional methods, e.g. by column chromatography, thin-layer chromatography, HPLC and the like.

Salts of comppounds with salt-forming groups are in particular acid addition salts, salts with bases or, if a plurality of salt-forming groups is present, optionally also mixed salts or inner salts.

Salts are primarily the pharmaceutically acceptable or non-toxic salts of compounds of the formula (I).

Such salts are formed for example by compounds of the formula (I) having an acidic group, e.g. a carboxy or sulpho group, and are for example their salts with suitable bases, such as non-toxic metal salts derived from metals of group Ia, Ib, IIa and IIb of the Periodic Table of the Elements, e.g. alkali metal, in particular lithium, sodium or potassium, salts, alkaline earth metal salts, for example magnesium or calcium salts, furthermore zinc salts or ammonium salts, also salts formed with organic amines such as optionally hydroxyl-substituted mono-, di- or trialkylamines, expecially mono-, di or tri-lower-alkylamines or with quaternary ammonium bases, e.g. methyl-, ethyl-, diethyl- or triethylamine, mono-, bis- or tris(2-hydroxy-lower-alkyl)amines such as ethanol-, diethanol- or triethanolamine, tris(hydroxymethyl)methylamine or 2-hydroxy-tertiary-butylamine, N.N-di-loer-alkyl-N-(hydroxyl-lower-alkyl)amine, such as N,N-dimethyl-N-(2-hydroxyethyl)amine, or N-methyl-D-glucamine, or quaternary ammonium hydroxides such as tetrabutylammonium hydroxide. The compounds of the formula I having a basic group, e.g. an amino group, can form acid addition salts, e.g. with suitable inorganic acids, e.g. hydrohalic acid such as hydrochloric acid, hydrobromic acid, sulphuric acid with replacement of one or both protons, phosphoric acid with replacement of one or more protons, e.g. orthophosphoric acid or metaphosphoric acid, or pyrophosphoric acid with replacement of one or more protons, or with organic carboxylic, sulphonic or phosphonic acids or N-substituted sulphamic acids, e.g. acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid, isonicotinic acid, furthermore amino acids such as, for example, the α-amino acids mentioned herein below, methanesulphonic acid, ethanesulphonic acid, 2-hydroxyethanesulphonic acid, ethane-1,2-disulphonic acid, benzenesulphonic acid, 4-toluenesulphonic acid, naphthalene-2-sulphonic acid, 2- or 3-phosphoglycerate, glucose 6-phosphate, N-cyclohexylsulphamic acid (to form cyclamates) or with other acidic organic compounds such as asorbic acid. Compounds of the formula (I) having acidic and basic groups may also form inner-salts.

Pharmaceutically unsuitable salts may also be used for isolation and purification.

Where this is possible groups of compounds mentioned hereinafter are not to be regarded as dosed; on the contrary, it is possible for parts of the groups of compounds to be interchanged or replaced by the definitions given above, or omitted, in a worthwhile manner, e.g. to replace general by more specific definitions.

Preferred compounds of the invention are those of the general formula (IA)

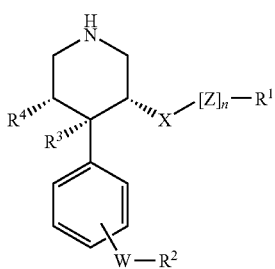

(IA)

in which $R^1$, $R^2$, $R_3$, $R^4$, W, X, Z and n have the meaning indicated above for the compounds of the formula (I).

A further preferred group of compounds of the formula (I), or particularly preferably of the formula (IA), are compounds in which $R^1$ is aryl under the conditions indicated for (A), (B) or (C), or heterocyclyl, substituted as indicated under (D), or (E), where heterocydyl is particularly preferably selected from benzo[1,3]dioxolyl, benzofuranyl, benzooxazolyl, dihydrobenzofuranyl, 3,4-dihydro-2H-benzo[1,4]oxazinyl, dihydro-3H-benzo[1,4]oxazinyl, dihydro-2H-benzo[1,4]thiazinyl, 2,3-dihydro-1H-pyrido[2,3-b][1,4]oxazinyl, 1,1-dioxodihydro-2H-benzo[1,4]thiazinyl, indazolyl, indolyl, [1,5]naphthyridyl, oxazoyl, 2-oxoazepanyl, 3-oxo4H-benzo[1,4]oxazinyl, 2-oxobenzooxazolyl, 3-oxo-4H-benzo[1,4]thiazinyl, 2-oxodihydro-benzo[e][1,4] diazepinyl, 2-oxodihydrobenzo-[di][1,3]oxazinyl, 2-oxodihydro-1H-quinazolinyl, 4-oxodihydroimidazolyl, 2oxo-1,3-dihydroindolyl, 1-oxo-3H-isobenzofuranyl, 2-oxopiperidinyl 2oxo-1H-pyrido[2,3,b][1,4]oxazinyl, 1-oxopyridyl, 2-oxotetrahydrobenzo[e][1,4]diazepinyl, 4-oxo-3H-thieno[2,3-d]pyrimidinyl, 5-oxo-4H-[1,2,4]triazinyl, phthalazinyl, pyrazolyl, 1H-pyrrolizinyl, 1H-pyrrolo[2,3-b]pyridyl, pyrrolyl, tetrahydroquinoxalinyl, tetrahydropyranyl, triazinyl and 1,1,3-trioxodihydro-2H-1lambda*6*-benzo[1,4]thiazinyl.

A further preferred group of compounds of the formula (I), or particularly preferably of the formula (IA), are compounds in which $R^1$ had the meaning as indicated for (A), (B), (C), (D), (E) or (F), particularly preferably as indicated for (B), (D), (E) or (F);

$R^2$ is phenyl or a heterocyclyl linked via a C atom, each of which radicals may be substituted by 1-4 $C_{1-6}$alkanoyl, $C_{1-6}$alkoxy, $C_{1-6}$alkoxy-$C_{1-6}$alkoxy, $C_{1-6}$alkyoxy-$C_{1-6}$alkyl, $C_{1-6}$alkoxy-carbonylamino, $C_{1-6}$alkyl, $C_{0-6}$alkylcarbonylamino, $C_{1-6}$alkylenedioxy, $C_{1-6}$alkylsulphanyl, $C_{1-6}$alkylsulphonyl, optionally N-mono- or N,N-di-$C_{1-6}$-alkylated amino, optionally-N-mono- or N,N-di-$C_{1-6}$-alkylated carbamoyl, optionally esterified carboxy, cyano, cyano-$C_{1-6}$alkyl, $C_{3-8}$cycloalkoxy, $C_{3-8}$cycloalkyl, halogen, hydroxy-$C_{1-6}$alkyl, nitro, oxide, oxo, trifluoromethyl, trifluoromethoxy or optionally N-$C_{1-6}$-alkylated piperazinyl-$C_{1-6}$alkyl;

$R^3$ is hydrogen, hydroxy, $C_{1-6}$alkoxy or $C_{2-6}$-alkenyloxy;

$R^4$ is $C_{1-6}$alkoxy, $C_{1-6}$alkoxy-$C_{1-6}$alkoxy, optionally N-mono- or N,N-di-$C_{1-6}$alkylated amino-$C_{1-6}$alkoxy, optionally N-$C_{1-6}$-alkylated $C_{1-6}$-alkoxycarbonylamino-$C_{1-6}$alkoxy, optionally N—$C_{1-6}$-alkylated $C_{1-6}$alkylcarbonylamino-$C_{1-6}$alkoxy, $C_{3-8}$cycloalkyloxy, $C_{3-8}$cycloalkyloxy-$C_{1-6}$alkoxy, hydroxy, hydroxy-$C_{2-6}$alkoxy, hydroxy-$C_{2-6}$alkoxy-$C_{1-6}$alkoxy, heterocyclyl-$C_{1-6}$alkoxy, heterocyclyloxy, heterocyclyloxy-$C_{1-6}$alkoxy or oxo;

$R^5$ is acyl, $C_{2-8}$alkenyl, $C_{1-6}$alkyl, aryl-$C_{1-6}$alkyl or hydrogen;

$R^6$ is acyl, $C_{1-6}$alkoxy-$C_{1-6}$-alkyl, $C_{1-6}$alkyl or aryl-$C_{1-6}$alkyl or hydrogen;

$R^7$ is $C_{1-6}$alkoxycarbonyl-$C_{1-6}$alkyl, $C_{1-6}$alkyl, carboxy-$C_{1-6}$alkyl or hydrogen;

X is a bond, oxygen or sulphur, where the bond originating from an oxygen or sulphur atom leads to a saturated C atom of the group Z or to $R^1$, or a group >CH—$R^5$, >CHOR$^6$, —O—CO—, >CO, >C=NOR—, —O—CHR$^5$— or —O—CHR$^5$—CO—NR$^6$—;

Z is $C_{1-6}$alkylene, $C_{2-8}$alkenylene, hydroxy-$C_{1-6}$alkylidene, —O—, —S—, —O-alk-, —S-alk-, -alk-O—, -alk-S— or -alk-NR$^6$—, where alk is $C_{1-6}$alkylene, and where (a) if Z is —O-alk- or —S-alk-, then X is —CHR$^5$—, and
(b) if X is a bond, then Z is $C_{2-8}$alkenylene, -alk-O— or -alk-S—;

n is1 is or, if X is —O—CO— or —O—CHR$^5$—CO—NR$^6$—, 0 or 1;

and pharmaceutically acceptable salts thereof.

Further preferred compounds of the formula (I) and (IA) are those in which X is preferably oxygen, sulphur, —O-CHR$^5$—, —O—CHR$^5$—CO—NR$^6$— or —CO, Z is preferably methylene or -alk-O—m Further preferred compounds of the formulae (I) and (IA) are those in which W is oxygen.

Further preferred compounds of the formulae (I) and (IA) are those in which $R^3$ is hydrogen.

Further preferred compounds of the formulae (I) and (IA) are those in which $R^3$ is hydrogen.

Further preferred compounds of the formulae (I) and (IA) are those in which $R^4$ is optionally N-mono- or N,N-di-$C_{1-6}$ alkylated amino-$C_{1-6}$alkoxy or hydroxyl.

A group of preferred radicals $R^1$ includes the above mentioned substituted phenyl and naphthyl radicals, and tetrahydronaphthyl and methyl-substituted tetrahydronaphthyl.

Likewise preferred radicals, $R^1$ are pyridyl benzoimidazolyl, pyrimidinyl, 2- and 5-benzo[b]thienyl, 6- and 7-quinolyl, 6- and 7-isoquinolyl, 6,-and 7-tetrahydroquinolyl, 6- and 7-tetrahydroisoquinolyl, 6-quinoxalinyl, 6- and 7-quinazolinyl, indolyl, 3,4-dihydro-2H-benzo[1,4]oxazinyl, dihydro-3H-benzo[1,4]oxazinyl, 3-oxo-4H-benzo[1,4]oxazinyl, benzooxazolyl, 2,3-dihydroindolyl, indazolyl or benzofuranyl, and halogen-, oxide-, oxo-, $C_{1-6}$alkoxy-, $C_{1-6}$alkoxy-$C_{1-6}$alkoxy-, $C_{1-6}$alkoxy-$C_{1-6}$alkyl-, $C_{1-6}$alkoxycarbonyamino-$C_{1-6}$-alkoxy-, $C_{1-6}$alkoxycarbonylamino-$C_{1-6}$ alkyl-, $C_{1-6}$alkyl-, $C_{0-6}$alkylcarbonylamino-$C_{1-6}$alkoxy-, $C_{0-6}$alkylcarbonylamino-$C_{1-6}$alkyl-, $C_{1-6}$alkoxy-$C_{1-6}$alkoxy-$C_{1-6}$alkyl-, cyano-$C_{1-6}$alkoxy-, cyano-$C_{1-6}$alkyl- or trifluoromethyl-substituted 6- and 7-quinolyl, 6- and 7-isoquinolyl, 6- and 7-tetrahydroquinolyl, 6- and 7-tetrahydroisoquinolyl, 6-quinoxalinyl 6- and 7-quinazolinyl, indolyl, 3,4-dihydro-2H-benzo[1,4]oxazinyl, dihydro-3H-benzo[1,4]oxazinyl, 3-oxo-4H-benzo[1,4]oxazinyl, benzooxazolyl, 2,3dihydroindolyl, indazolyl or benzofuranyl.

$R^1$ is very particularly preferably substituted 3,4-dihydro-2H-benzo[1,4]oxazinyl.

Preferred radicals $R^2$ in the meaning of a heterocyclyl linked via a C atom are pyridyl, pyrimidinyl, pyrazinyl, benzo[b]thienyl, quinolyl, isoquinolyl, quinoxalinyl, indolyl, 3,4diydro-2H-benzo[1,4]oxazinyl, 2,3-dihydrobenzofuranyl or benzofuranyl.

Preferred radicals $R^2$ are phenyl or a heterocyclyl linked via a C atom, which radicals may be substituted by 1-4$C_{1-6}$ alkanoyl, $C_{1-6}$alkoxy, $C_{1-6}$alkoxy-$C_{1-6}$alkoxy, $C_{1-6}$alkoxy-$C_{1-6}$alkyl, $C_{1-6}$alkyl, $C_{0-6}$alkylcarbonylamino, $C_{1-6}$alkylenedioxy, $C_{1-6}$alkylsulphanyl, $C_{1-6}$alkylsulphonyl, optionally N-mono- or N,N-di-$C_{1-6}$alkylated amino, optionally N-mono- or N,N-di-$C_{1-6}$-alkylated carbamoyl, cyano, halogen, hydroxy-$C_{1-6}$alkyl, oxide or trifluoromethyl.

The compounds of the formula (I) can be prepared in a manner analogous to preparation processes disclosed in the literature. Similar preparation processes are described for example in WO 97/09311. Details of the specific preparation variants can be found in the examples.

The compounds of the formula (I) can also be prepared in optically pure form. Separation into antipodes can take place by methods known per se, either preferably at an early stage in the synthesis by salt formation with an optically active acid such as, for example, (+)- or (−)- mandelic acid and separation of the diastearomeric salts by fractional crystallization or preferably at a rather late stage by derivatizing with a chiral auxiliary component such as, for example, (+)- or (−)-camphanoyl chloride, and separation of the diastereomeric products by chromatography and/or crystalization and subsequent cleavage of the linkage to the chiral auxiliary. The pure diastereomeric salts and derivatives can be analysed to determine the absolute configuration of the contained piperidine by conventional spectroscopic methods, with X-ray spectroscopy on single crystals representing a particularly suitable method.

The compounds of the formula (I) and (IA) also include compounds in which one or more atoms are replaced by their stable, nonradioactive isotopes; for example a hydrogen atom by deuterium.

Prodrug derivatives of the compounds described herein are derivatives thereof which on in vivo use liberate the original compound by a chemical or physiological process. A prodrug may for example be converted into the original compound when a physiological pH is reached or by enzymatic conversion. Possible examples of prodrug derivatives are esters of freely available carboxylic acids, S- and O-acl derivatives of thiols, alcohols or phenols, the acyl group being defined as above. Preferred derivatives are pharmaceutically acceptable esters which are converted by solvolysis in physiological medium into the original carboxylic acid, such as, for example, lower alkyl esters, cycloalkyl esters, lower alkenyl esters, benzyl esters, mono- or disubstituted lower alkyl esters such as lower ω-(amino, mono- or dialkyl-amino, carboxy, lower alkoxycarbonyl)-alkyl esters or such as lower α-(alkanoyloxy, alkxycarbonyl or dialkylaminocarbonyl)-alkyl esters; conventionally; pivaloyloxymethy, esters and similar esters are used as such.

Because of the cloaw relationship between a free compound, a prodrug derivative and a salt compound, a particular compround in this invention also includes its prodrug derivative and salt form, where possible and appropriate. The definitions mentioned apply within the framework of general chemical principles such as, for example, the usual valences for atoms.

The compounds of the formula (I), and of the formula (IA), and their pharmaceutically acceptable salts have an inhibitory effect on the natural enzyme renin. The latter passes from the kidneys into the blood and there brings about the deavage of angiotensinogen to form the decapeptide angiotensin I which is then cleaved in the lung, the kidneys and other organs to the octapepbde angiotensin II. Angiotensin II raises the blood pressure both directly by arterial constriction, and indirectly by releasing the hormone aldosterone, which retains sodium ions, from the adrenals, which is associated with an increase in the extracellular fluid volume. This increase is attributable to the effect of angiotensin II itself or of the heptapeptide angiotensin III formed therefrom as cleavage product. The inhibitors of the enzymatic activity rerin bring about a reduction as in the formation of angiotension I and; as a consequence thereof, the formation of a smaller amount of angiotensin II. The reduced concentration of this active peptide hormone is the direct cause of the blood pressure-lowering effect of renin inhibitors.

The effect of renin inhibitors is detected inter alia experimentally by means of in vitro tests where the reduction in the formation of angiotensin I is measured in various systems (huuman plasma, purified human renin together with synthetic or natural renin substrate). The following in vitro test of Nussberger et al. (1987) J. Cardiovascular Pharmacol., Vol. 9, p. 39-44, is used inter alia. This test measures the formation of angiotensin I in human plasma. The amount of angiotensin I formed is determined in a subsequent radio-immunoassay. The effect of inhibitors on the formation of angiotensin I is tested in the system by adding various concentrations of these substances. The $IC_{50}$ is defined as the concentration of the particular inhibitor which reduces the formation of angiotensin I, by 50%. The compounds of the present invention show inhibitory effects in the in vitro systems at minimal concentrations of about $10^{-6}$ to about $10^{-10}$ mol/l.

Renin inhibitors bring about a fall in blood pressure in salt-depleted animals. Human renin differs from renin of other species. Inhibitors of human renin are tested using primates (marmosets, Callithrix jacchus) because human renin and primate renin are substantally homologous in the enzymatically active region. The following in vivo test is employed inter alia: the test compounds are tested on normotensive marmosets of both sexes with a bodyweight of about 350 g, which are conscious, unrestrained and in their normal cages. Blood pressure and heart rate are measufed withh a catheter in the descending aorta and are recorded radiometrically. Endogenous release of renin is stimulated by combining a low-salt diet for 1 week with a single intramuscular injection of furosemide (5-(aminosulphonyl)4-chloro-2-[(2-furanylmethyl)amino]benzoic acid) (5 mg/kg). 16 hours after the furosemide injection, the test substances are administered either directly into the femoral artery by means of a hypodermic needle or as suspension or solution by gavage into the stomach, and their effect on blood pressure and heart rate is evaluated. The compounds of the present invention have a blood pressure-lowering effect in the described in vivo test with i.v. doses of about 0,.003 to about 0.3 mg/kg and with oral doses of about 0.3 to about 30 mg/kg.

The compounds of the formula (I), and preferably of the formula (IA), and their pharmaceuticaly acceptable salts can be uses as medicines, e.g. in the form of pharmaceutical products. The pharmaceutical products can be administered enterally, such as orally, e.g.in the form of tablets, laquered tablets, sugar-coated tablets, hard and soft gelatine capsules, solutions, emulsions or suspensions, nasally, e.g. in the form of nasal sprays, rectally, e.g. in the form of suppositories, or transdermally, e.g. in the form of ointments or patches. However, administration is also possible parenterally, such as intramuscularly or intravenously, e.g. in the form of solutions for injection.

Tablets, lacquered tablets, sugar-coated tablets and hard gelatine capsules can be produced by processing the comppunds of the formula (I), or preferably of the formula (IA), and their pharmaceutically acceptable salts with pharmaceutically inert inorganic or organic excipients. Excipients of these types which can be used for example for tablets, sugar-coated tablets and hard gelatine capsules are lactose, maize starch or derivatives thereof, talc, stearic acid or salts thereof etc.

Excipients suitable for soft gelatine capsules are, for example, vegetable oils, waxes, fats, semisolid and liquid polyols etc.

Excipients suitable for producing solutions and syrups are, for example, water, polyols, sucrose invert sugar, glucose etc.

Excipients suitable for solutions for injection are, example, water, alcohols, polyols, glycerol, vegetable oils, bile acids, lecithin etc.

Excipients suitable for suppositories are, for example, natural or hardened oils, waxes, fats, semiliquid or liquid polyols etc.

The pharmaceutical products may in addition comprise preservatives, solubilizers, viscosity-increasing substances, stabilizers, wetting agents, emulsifiers, sweeteners, colorants, aromatizers, salts to alter the osmotic pressure, buffers, coating agents or antioxidants. They may also comprise other substances of therapeutic value.

The present invention further provides the use of the compounds of the formula (I), or preferably of the formula (IA), and their pharmaceutically acceptable salts in the treatment or prevention of high blood pressure, heart failure, glaucoma, myocardial infarction, renal failure, restenoses and stroke.

The compounds of the formula (I), and preferably of the formula (IA), and their pharmaceutically acceptable salts can also be administered in combination with one or more agents having cardiovascular activity, e.g. α- and β-blockers such as phentolamine, phenoxy-benzamine, prazosin, terazosin, tolazine, atenolol, metoprolal, nadolo, propranolol, timolol, carteolol etc.; vasodilators such as hydralazine, minoxidil, diazoxide, nitroprusside, flosequinan etc.; calcium antagonists such as amrinone, bencyclan, diltiazem, fendiline, flunarizine, nicardipine, nimodipine, perhexiline, verapamil, gallopamil nifedipine etc.; ACE inhibitors such as cilazapril, captopril, enalapril, lisinopril etc.; potassium activators such as pinacidil; antiserotoninergics such as ketanserine; thromboxane synthetase inhibitors; neutral endopeptidase inhibitors (NEP inhibitors); angiotensin II antagonists; and diuretics such as hydrochlorothiazide, chlorothiazide, acetazolamide, amiloride, bumetanide, benzthiazide, ethacrynic acid, furosemide, indacrinone, metolazone, spironolactone, triamterene, chlorthalidone etc.; sympatholytics such as methyl dopa, clonidine, guanabenz, reserpine; and other agents suitable for the treatment of high blood pressure, heart failure or vascular disorders associated with diabetes or renal disorders such as acute or chronic renal failure in humans and animals. Such combinations can be used separately or in products which comprise a plurality of components.

Further substances which can be used in combination with the compounds of the formulae (I) or (IA) are the compounds of classes (i) at (ix) on page 1 of WO 02/40007 and the preferences and examples detailed further therein) and the substances mentioned on pages 20 and 21 of WO 03/027091.

The dosage may vary within wide limits and must of course be adapted to the individual circumstances in each individual case. In qeneral, a daily dose appropriate for oral administration ought to be from about 3 mg to about 3 g, preferably about 10 mg to about 1 g, e.g. approximatey 300 mg per adult person (70 kg), divided into preferably 1-3 single doses, which may be for example of equal size, although the stated upper limit may also be exceeded where this proves necessary; children will usually receive a lower dose, appropriately reduced for their age and bodyweight.

EXAMPLE

The following examples illustrate the present invention. All temperatures are stated in. degrees Celsius and pressures in mbar. Unless mentioned otherwise, the reactions take place at room temperature. The abbreviation "Rf=xx (A)" means for example that the Rf is found in solvent system A to be xx. The ratio of amounts of solvents to one another is always stated in parts by volume. Chemical names for final products and intermediates have been generated on the basis of the chemical structural formulae with the aid of the AutoNom 2000 (Automatic Nomenclature) programme. Unless mentioned otherwise, the absolute stereochemistry of the 3,4,5-trisubstituted piperidine unit is (3S,4S,5R), with the absolute, stereochemistry of the 4-substituents being dependent on the relative priorities of the 3- and 5-substituents.

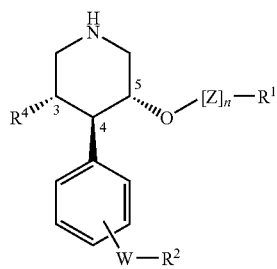
| No. | Structure | Appearance | R$_f$ (system) | Rt (method) |
|---|---|---|---|---|
| 1 | 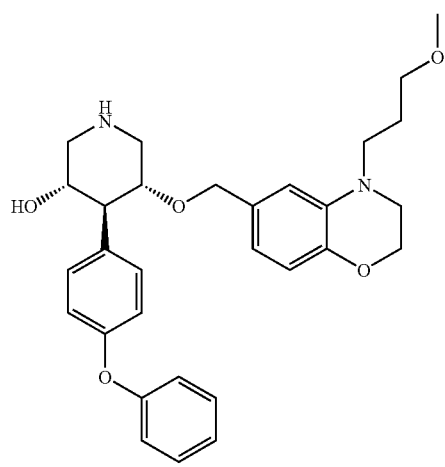 | colourless oil | 0.07 (A) | 4.04 (I) |
| 2 | 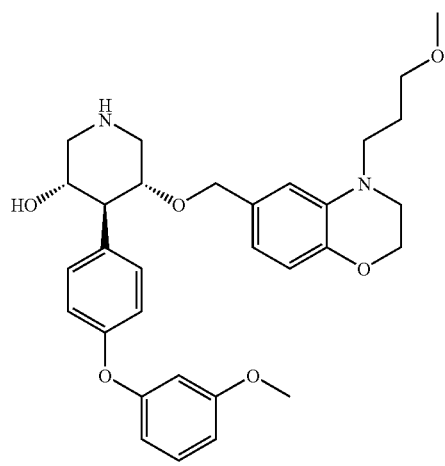 | beige resin | 0.32 (B) | 3.92 (I) |

-continued
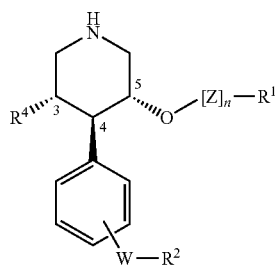
| No. | Structure | Appearance | R$_f$ (system) | Rt (method) |
|---|---|---|---|---|
| 3 | 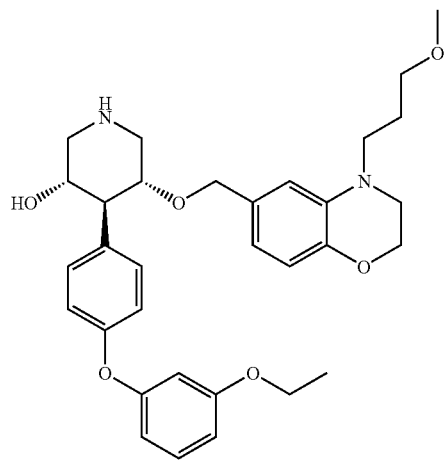 | yellow resin | 0.39 (B) | 4.28 (I) |
| 4 | 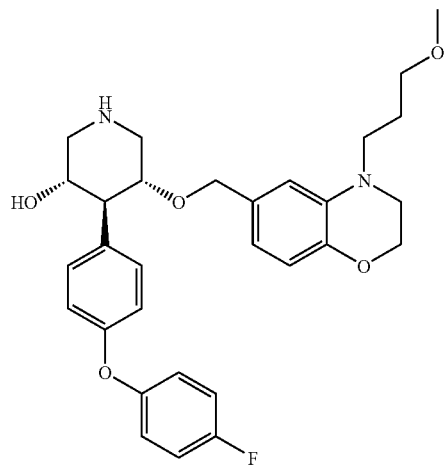 | brown oil | 0.37 (B) | 4.09 (I) |

-continued
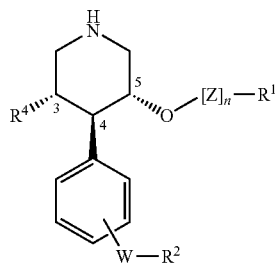
| No. | Structure | Appearance | R_f (system) | Rt (method) |
|---|---|---|---|---|
| 5 | 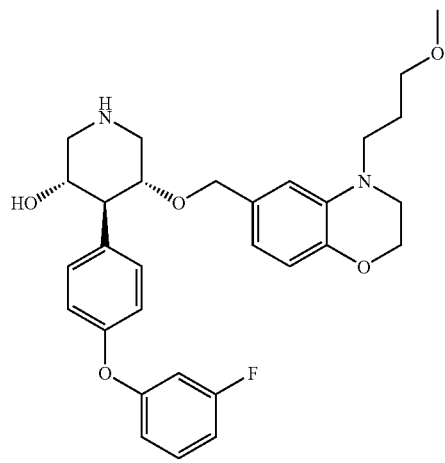 | yellow resin | 0.36 (B) | 4.11 (I) |
| 6 | 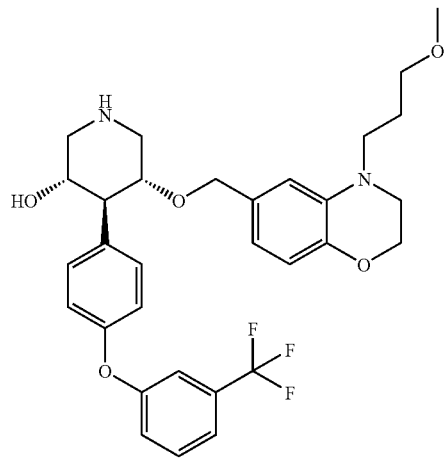 | colourless resin | 0.35 (B) | 4.44 (I) |

-continued
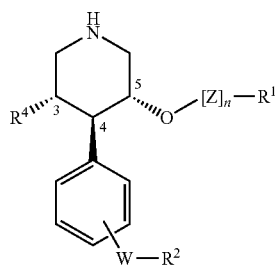
| No. | Structure | Appearance | R$_f$ (system) | Rt (method) |
|---|---|---|---|---|
| 7 | 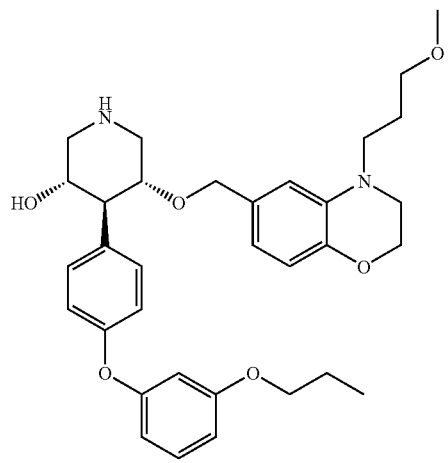 | colourless resin | 0.34 (B) | 4.58 (I) |
| 8 | 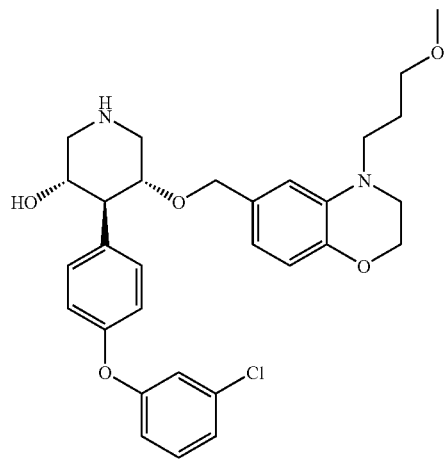 | colourless film | 0.19 (B) | 4.34 (I) |

-continued
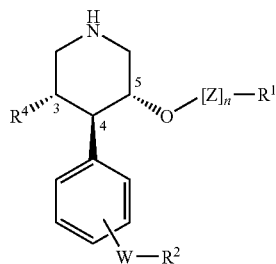
| No. | Structure | Appearance | $R_f$ (system) | Rt (method) |
|---|---|---|---|---|
| 9 | 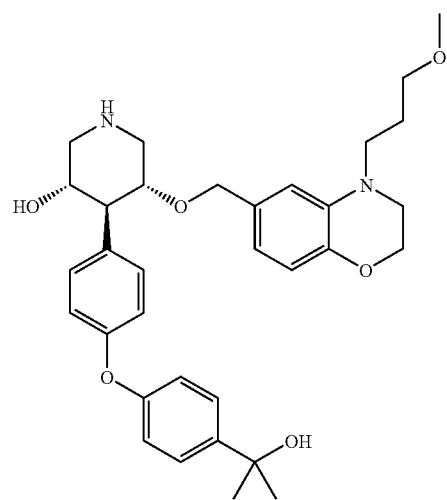 | colourless film | 0.15 (B) | 3.58 (I) |
| 10 | 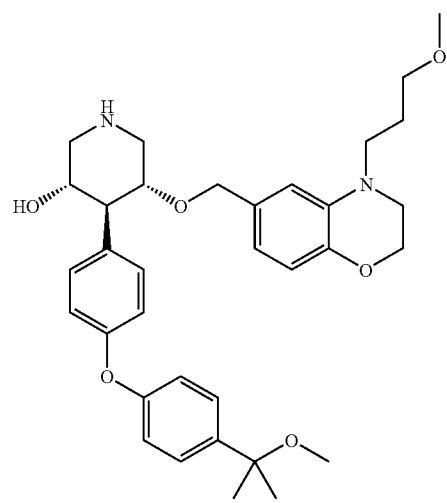 | colourless film | 0.36 (B) | 3.68 (I) |

-continued
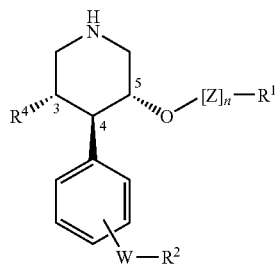
| No. | Structure | Appearance | R$_f$(system) | Rt (method) |
|---|---|---|---|---|
| 11 | 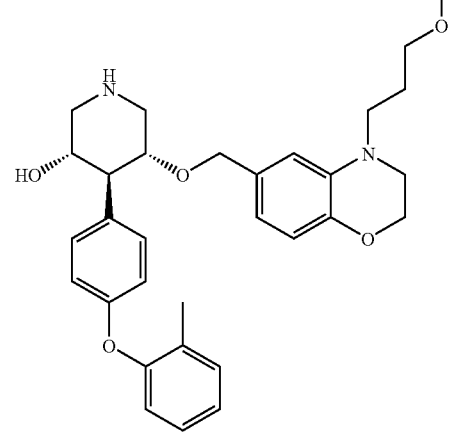 | beige resin | 0.30 (B) | 4.26 (I) |
| 12 | 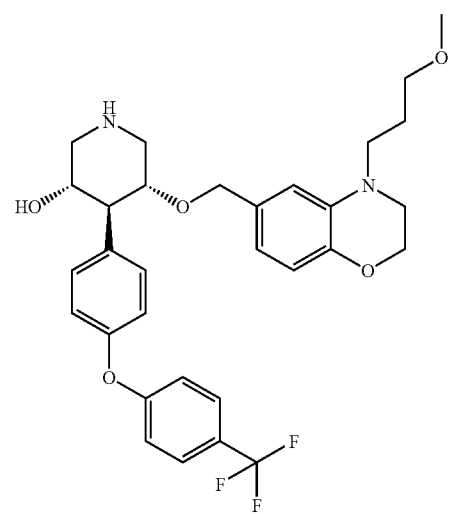 | beige oil | 0.24 (B) | 4.37 (I) |

-continued
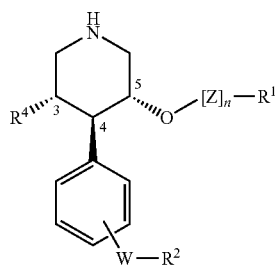
| No. | Structure | Appearance | R_f (system) | Rt (method) |
|---|---|---|---|---|
| 13 | 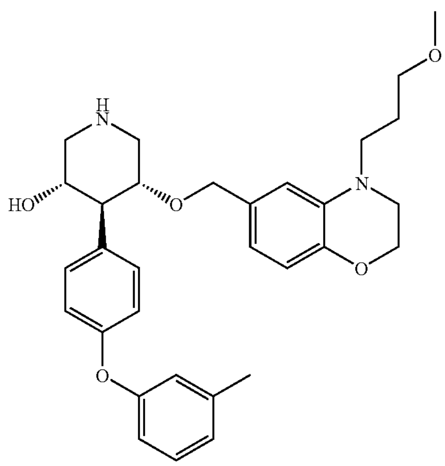 | beige oil | 0.28 (B) | 4.23 (I) |
| 14 | 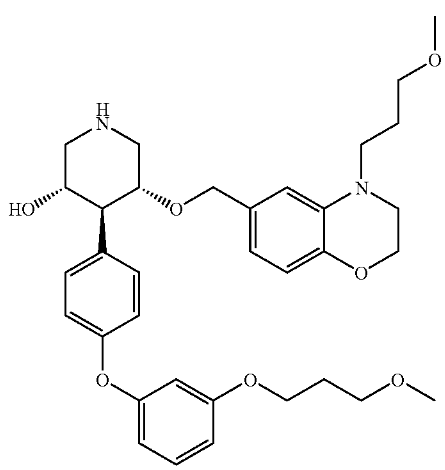 | colourless oil | 0.24 (B) | 4.13 (I) |

-continued
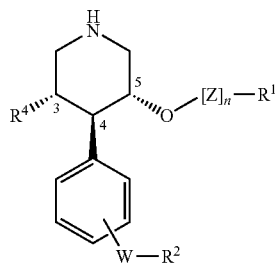
| No. | Structure | Appearance | R$_f$(system) | Rt (method) |
|---|---|---|---|---|
| 15 | 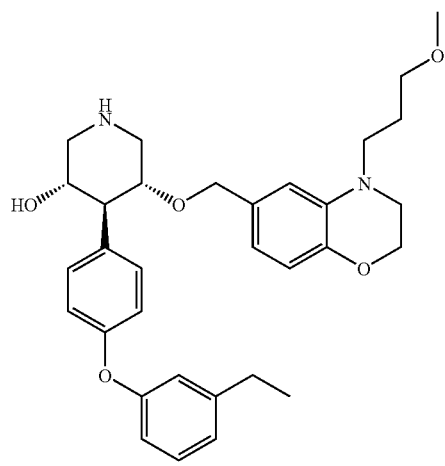 | colourless oil | 0.32 (B) | 4.46 (I) |
| 16 | 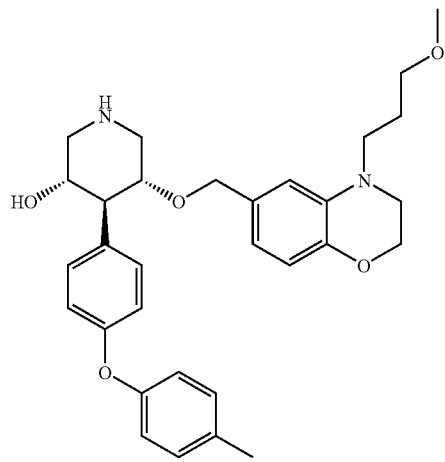 | colourless oil | 0.26 (B) | 4.25 (I) |

-continued
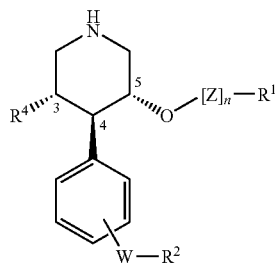
| No. | Structure | Appearance | R_f (system) | Rt (method) |
|---|---|---|---|---|
| 17 | 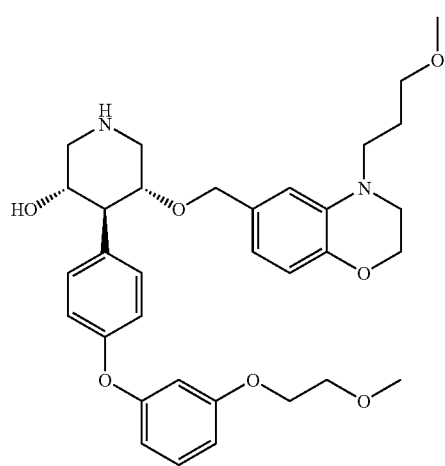 | yellow oil | 0.27 (B) | 3.92 (I) |
| 18 | 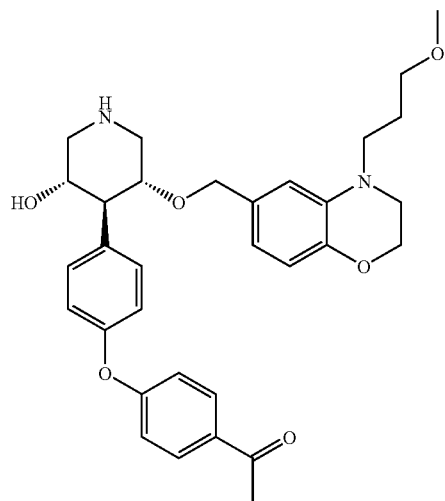 | colourless film | 0.17 (B) | 3.70 (I) |

-continued
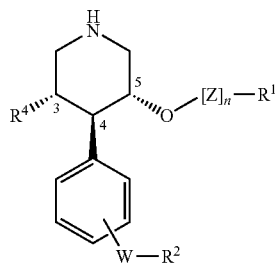
| No. | Structure | Appearance | R$_f$ (system) | Rt (method) |
|---|---|---|---|---|
| 19 | 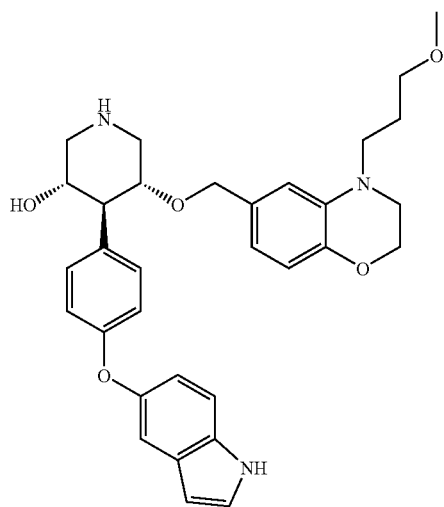 | yellowish solid | 0.11 (B) | 3.73 (I) |
| 20 | 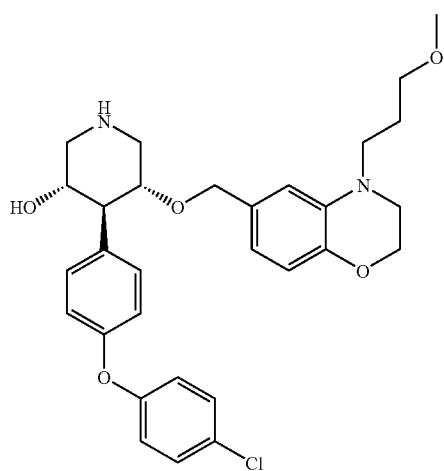 | yellow resin | 0.21 (B) | 4.32 (I) |

-continued
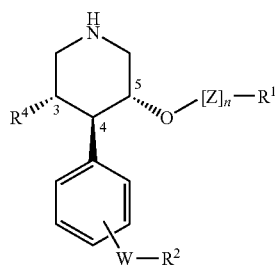
| No. | Structure | Appearance | R*f* (system) | Rt (method) |
|---|---|---|---|---|
| 21 | 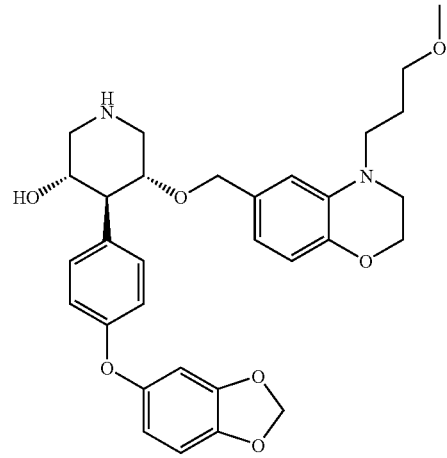 | yellowish solid | 0.26 (B) | 3.88 (I) |
| 22 | 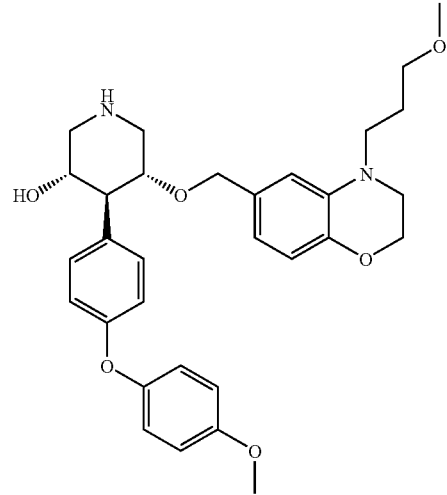 | yellowish solid | 0.21 (B) | 3.92 (I) |

-continued
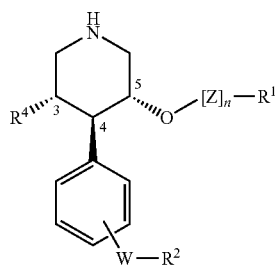
| No. | Structure | Appearance | $R_f$ (system) | Rt (method) |
|---|---|---|---|---|
| 23 | 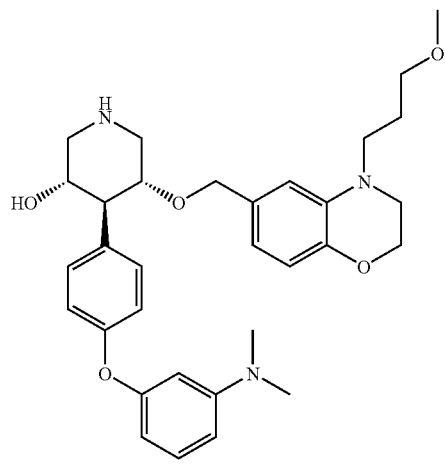 | white foam | 0.30 (B) | 3.12 (I) |
| 24 | 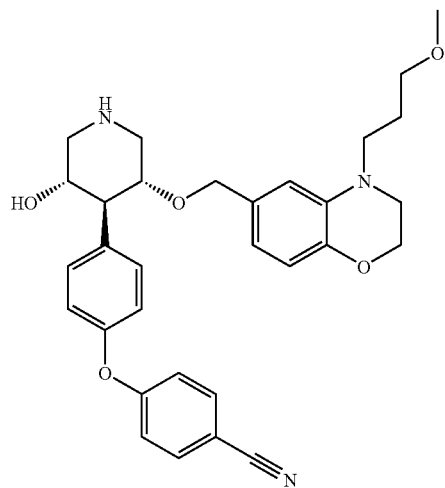 | white foam | 0.28 (B) | 3.78 (I) |

-continued
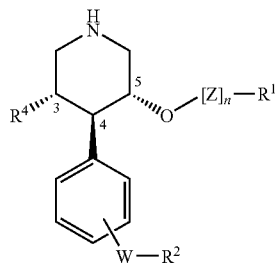
| No. | Structure | Appearance | R$_f$ (system) | Rt (method) |
|---|---|---|---|---|
| 25 | 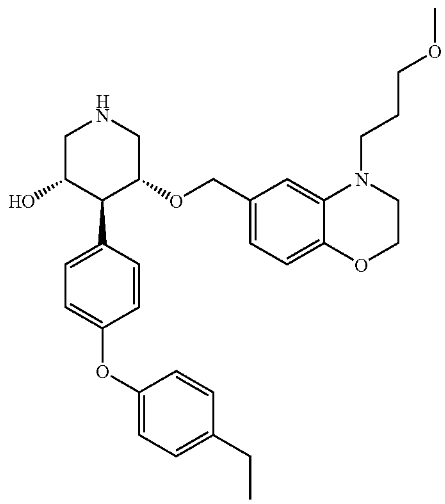 | yellowish foam | 0.36 (B) | 4.47 (I) |
| 26 | 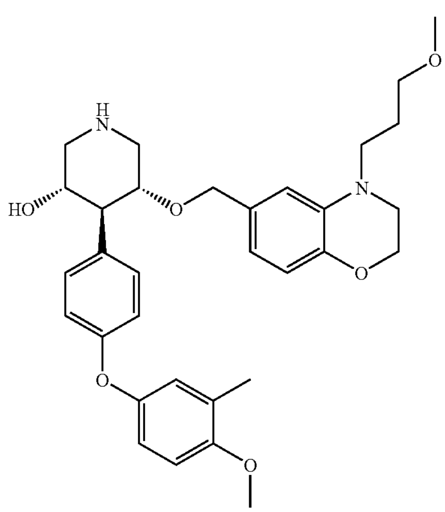 | yellowish foam | 0.30 (B) | 4.19 (I) |

-continued
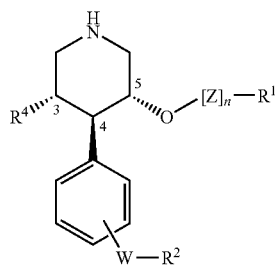
| No. | Structure | Appearance | R_f (system) | Rt (method) |
|---|---|---|---|---|
| 27 | 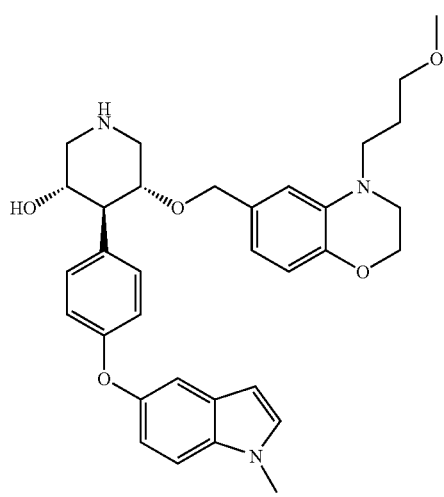 | yellowish foam | 0.25 (B) | 4.06 (I) |
| 28 | 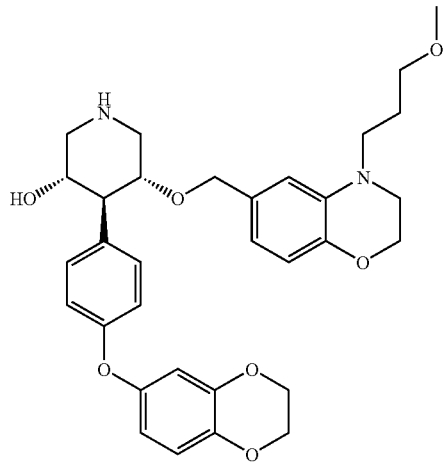 | yellowish foam | 0.23 (B) | 3.88 (I) |

-continued
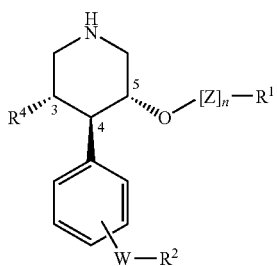
| No. | Structure | Appearance | R*f* (system) | Rt (method) |
|---|---|---|---|---|
| 29 | 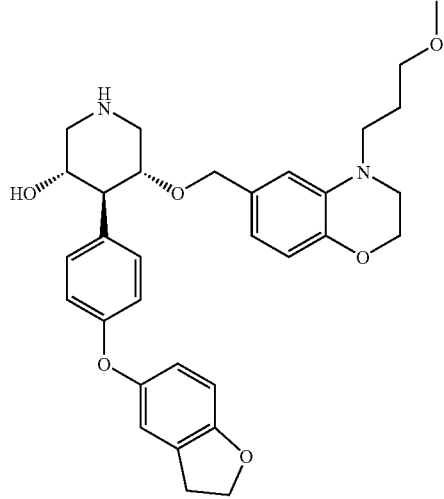 | yellowish foam | 0.33 (B) | 3.96 (I) |
| 30 | 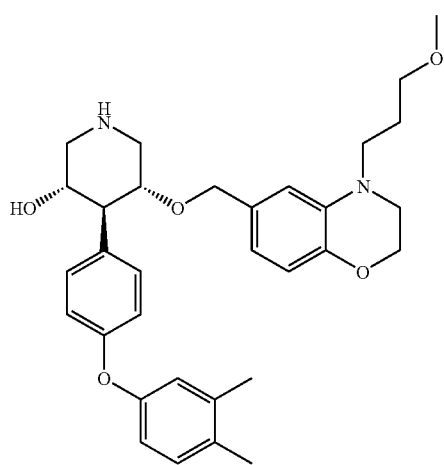 | yellowish foam | 0.33 (B) | 4.48 (I) |

-continued
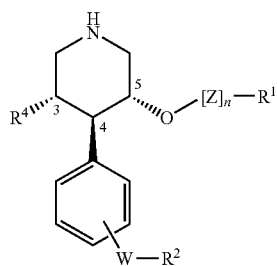
| No. | Structure | Appearance | R$_f$ (system) | Rt (method) |
|---|---|---|---|---|
| 31 | 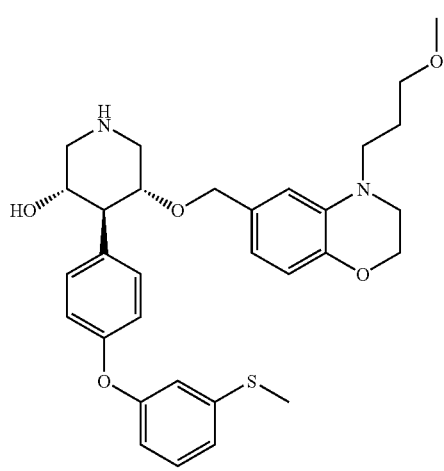 | yellowish foam | 0.27 (B) | 4.29 (I) |
| 32 | 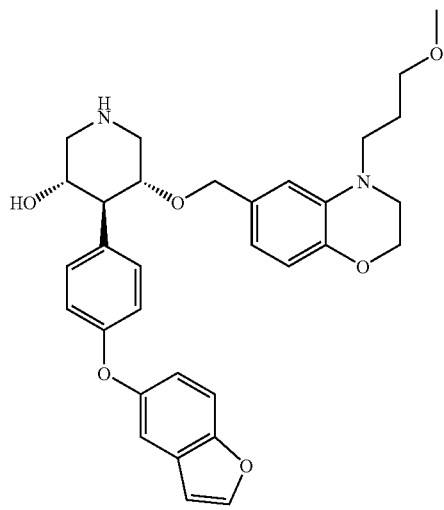 | yellowish foam | 0.25 (B) | 4.12 (I) |

-continued
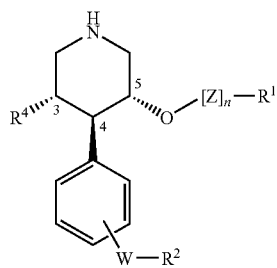
| No. | Structure | Appearance | R<sub>f</sub> (system) | Rt (method) |
| --- | --- | --- | --- | --- |
| 33 | 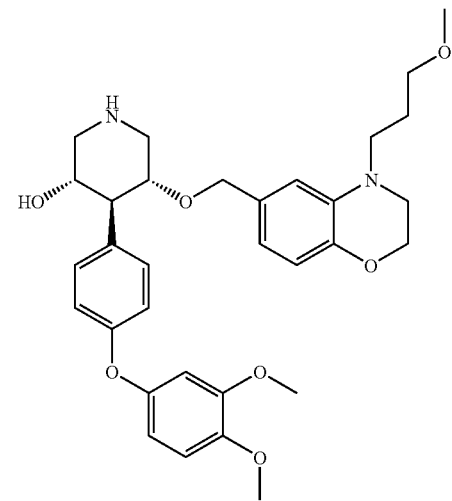 | yellow foam | 0.26 (B) | 3.73 (I) |
| 34 | 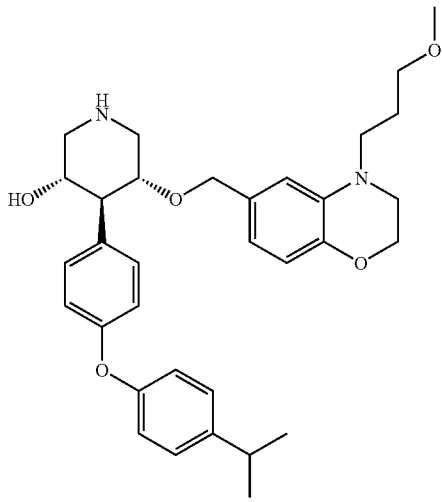 | yellow foam | 0.24 (B) | 4.77 (I) |

-continued
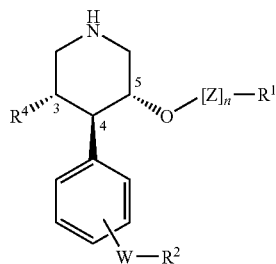
| No. | Structure | Appearance | R_f (system) | Rt (method) |
|---|---|---|---|---|
| 35 | 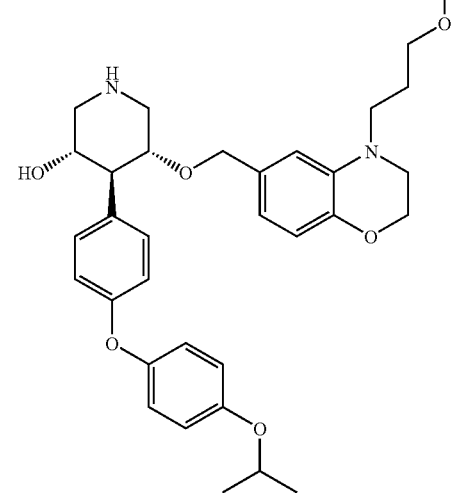 | yellowish foam | 0.24 (B) | 4.41 (I) |
| 36 | 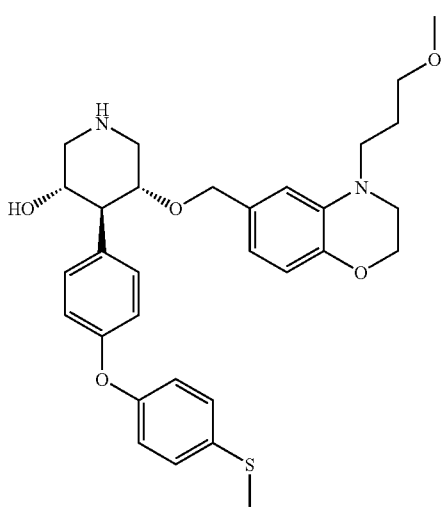 | yellow oil | 0.14 (B) | 4.29 (I) |

-continued
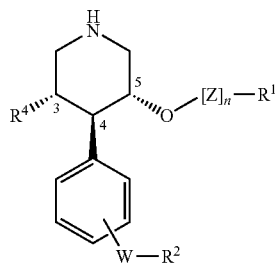
| No. | Structure | Appearance | R_f (system) | Rt (method) |
|---|---|---|---|---|
| 37 | 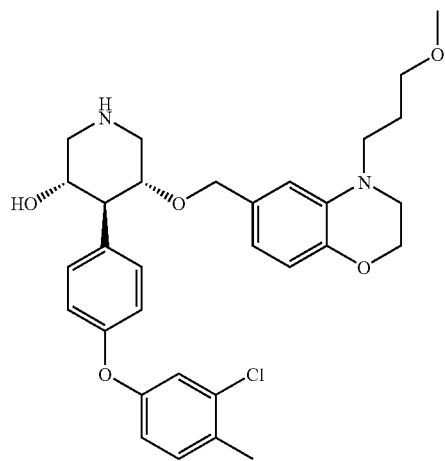 | yellow oil | 0.19 (B) | 4.65 (I) |
| 38 | 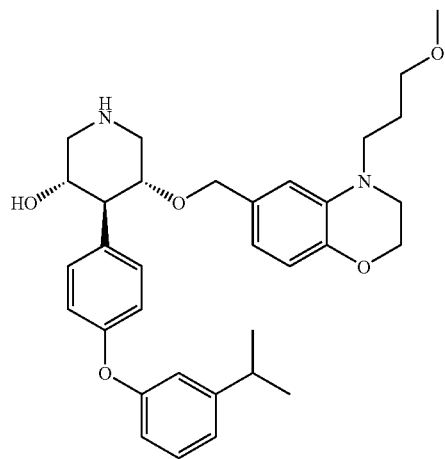 | yellow oil | 0.21 (B) | 4.73 (I) |

-continued
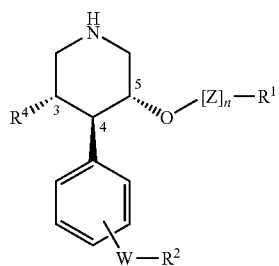
| No. | Structure | Appearance | R_f (system) | Rt (method) |
|---|---|---|---|---|
| 39 | 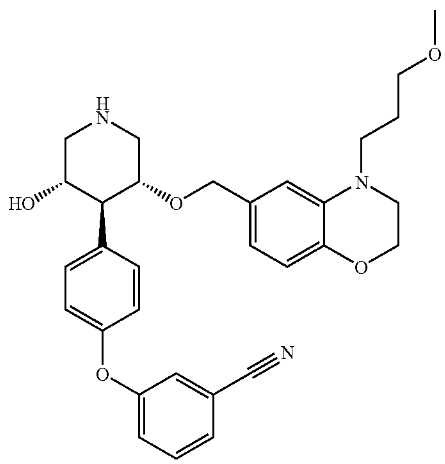 | yellowish foam | 0.31 (C) | 3.87 (I) |
| 40 | 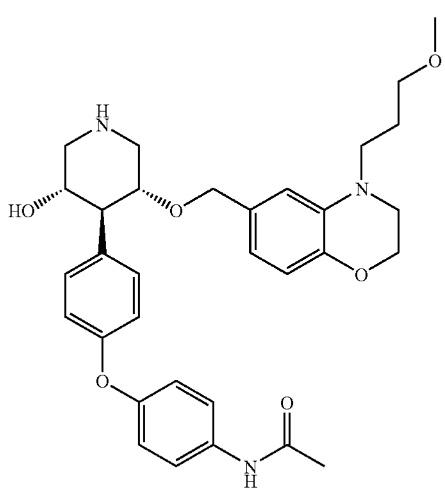 | colourless film | 0.18 (C) | 3.25 (I) |

-continued
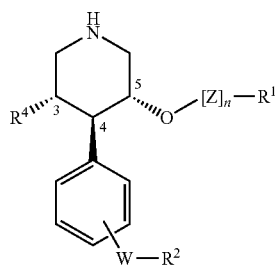
| No. | Structure | Appearance | R_f (system) | Rt (method) |
|---|---|---|---|---|
| 41 | 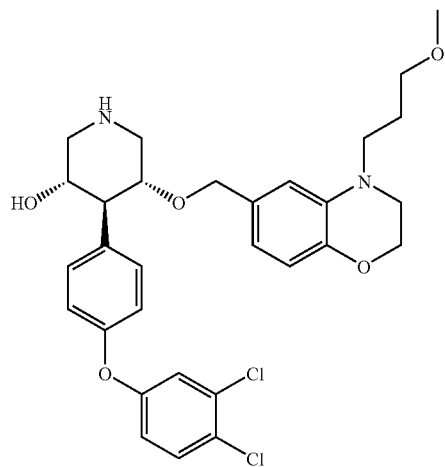 | yellowish oil | 0.38 (B) | 4.52 (I) |
| 42 | 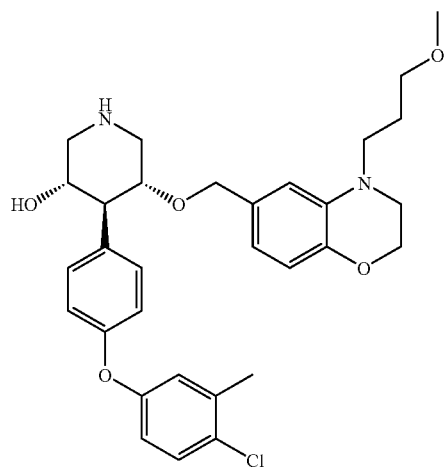 | yellowish oil | 0.26 (B) | 4.49 (I) |

-continued
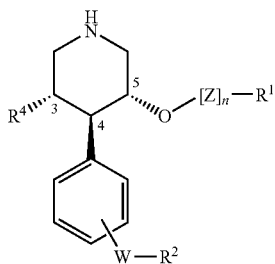
| No. | Structure | Appearance | R$_f$ (system) | Rt (method) |
|---|---|---|---|---|
| 43 | 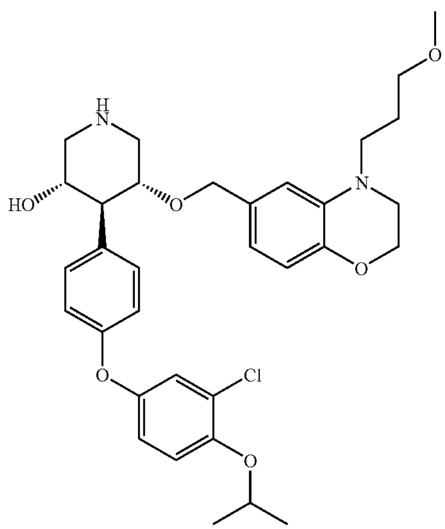 | yellowish oil | 0.26 (B) | 4.55 (I) |
| 44 | 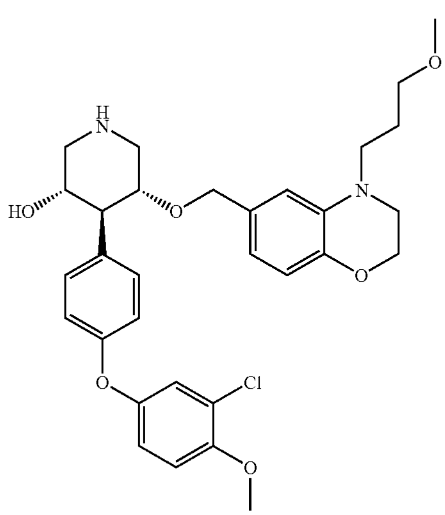 | colourless resin | 0.12 (D) | 4.21 (I) |

-continued
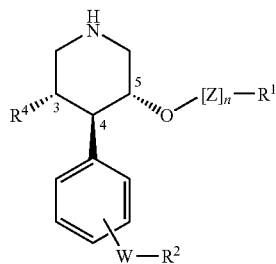
| No. | Structure | Appearance | R$_f$ (system) | Rt (method) |
|---|---|---|---|---|
| 45 | 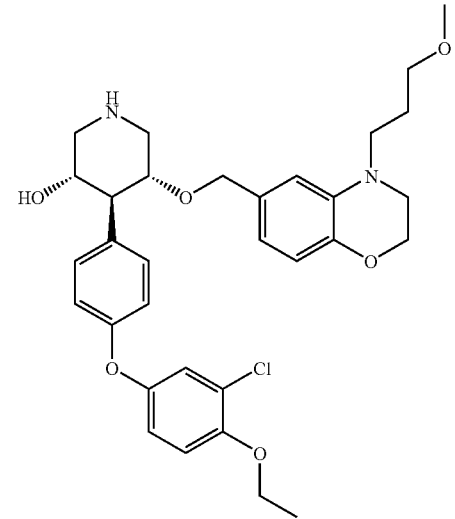 | colourless resin | 0.11 (D) | 4.51 (I) |
| 46 | 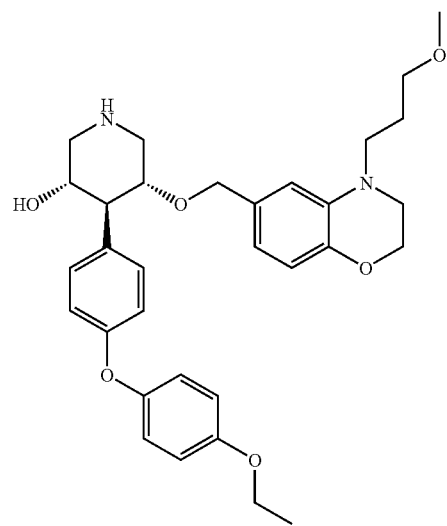 | colourless resin | 0.12 (D) | 4.25 (I) |

-continued
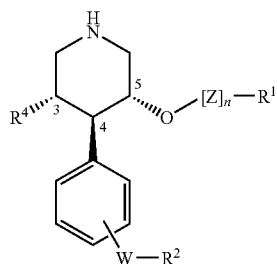
| No. | Structure | Appearance | R_f (system) | Rt (method) |
|---|---|---|---|---|
| 47 | 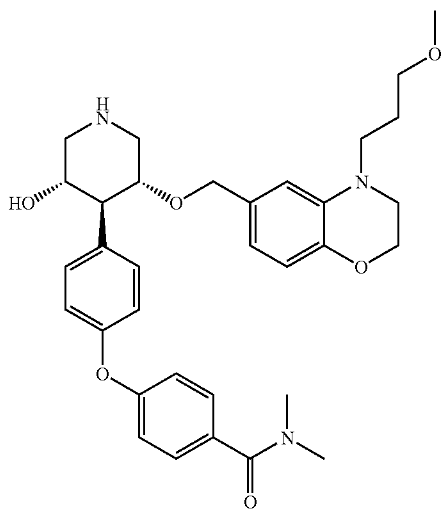 | colourless resin | 0.17 (C) | 3.29 (I) |
| 48 | 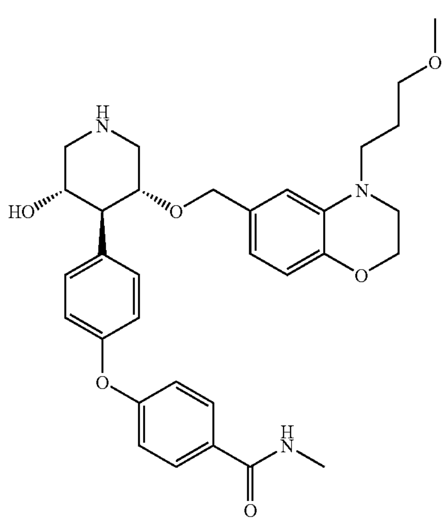 | colourless resin | 0.10 (C) | 3.11 (I) |
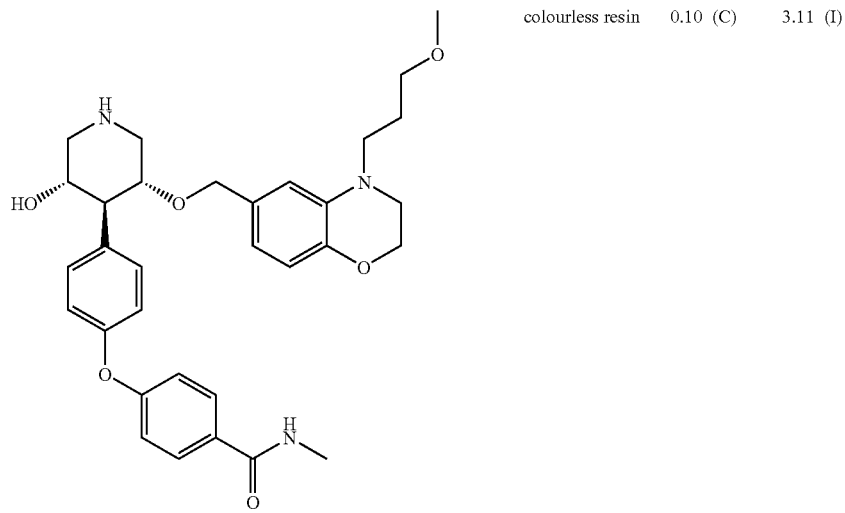

-continued
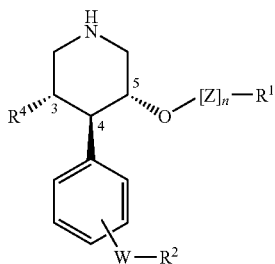
| No. | Structure | Appearance | R$_f$ (system) | Rt (method) |
|---|---|---|---|---|
| 49 | 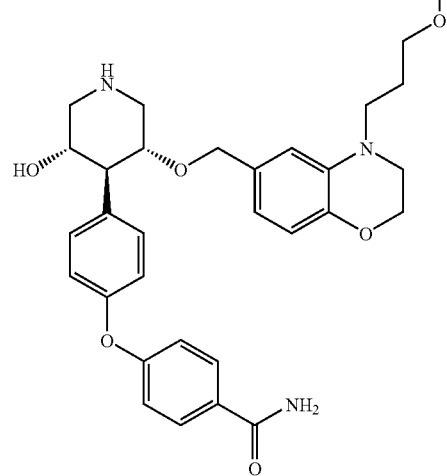 | yellow solid | 0.14 (E) | 3.05 (I) |
| 50 | 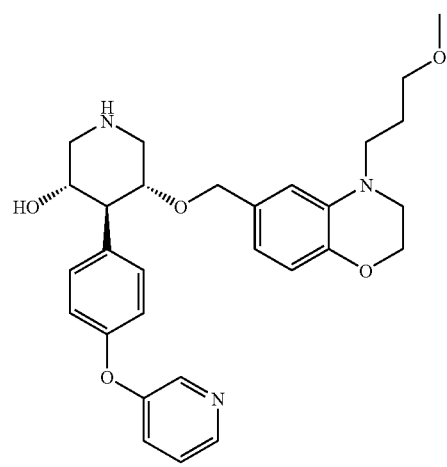 | yellowish film | 0.19 (E) | 2.81 (I) |

-continued
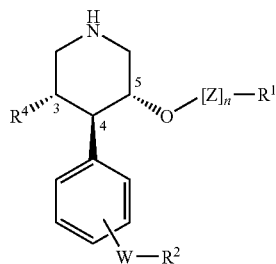
| No. | Structure | Appearance | R$_f$ (system) | Rt (method) |
|---|---|---|---|---|
| 51 | 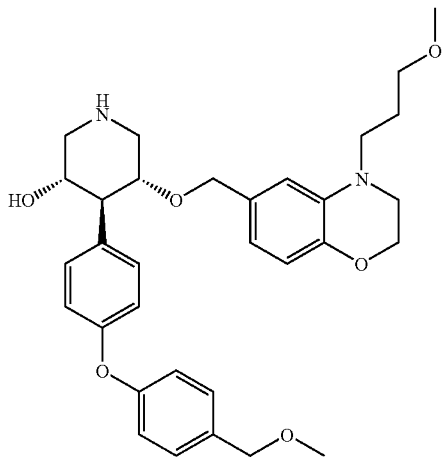 | colourless resin | 0.15 (D) | 3.91 (I) |
| 52 | 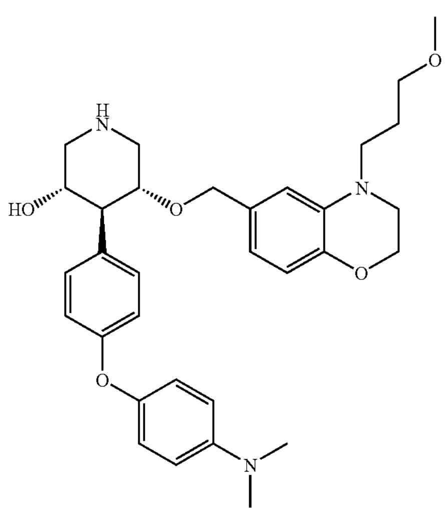 | colourless resin | 0.14 (D) | 2.91 (I) |

-continued
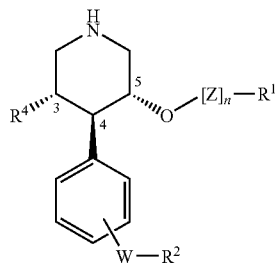
| No. | Structure | Appearance | R_f (system) | Rt (method) |
|---|---|---|---|---|
| 53 | 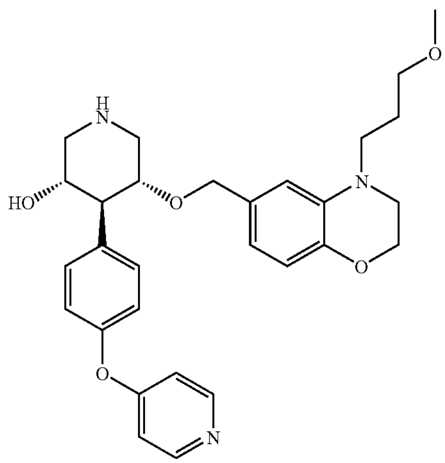 | yellow foam | 0.17 (E) | 2.71 (I) |
| 54 | 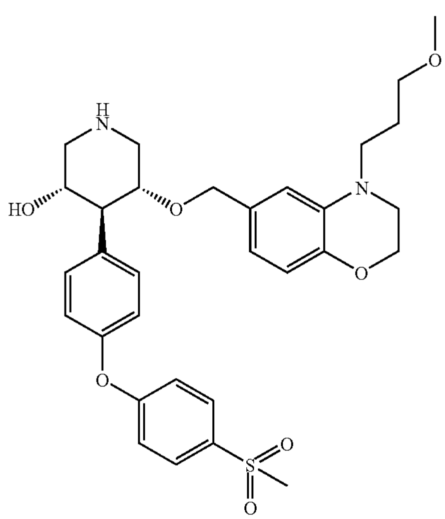 | yellow foam | 0.11 (B) | 3.46 (I) |

-continued
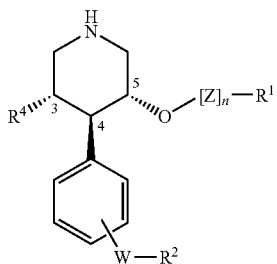
| No. | Structure | Appearance | R_f (system) | Rt (method) |
|---|---|---|---|---|
| 55 | 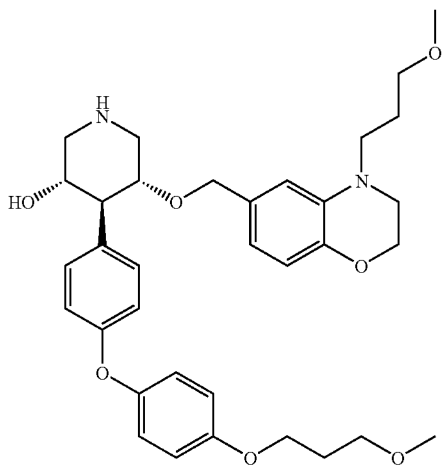 | colourless resin | 0.06 (D) | 4.12 (I) |
| 56 | 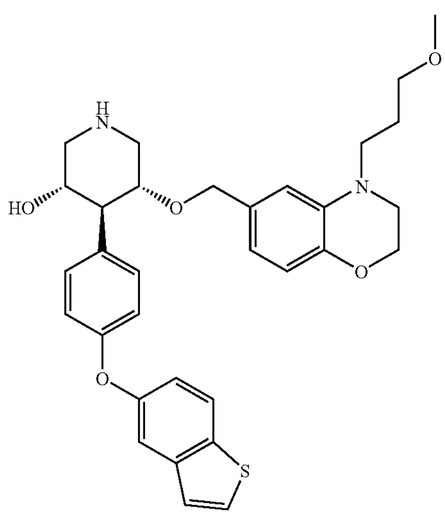 | colourless foam | 0.20 (B) | 4.36 (I) |

-continued
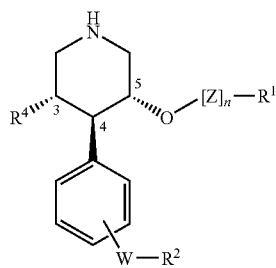
| No. | Structure | Appearance | R_f (system) | Rt (method) |
|---|---|---|---|---|
| 57 | 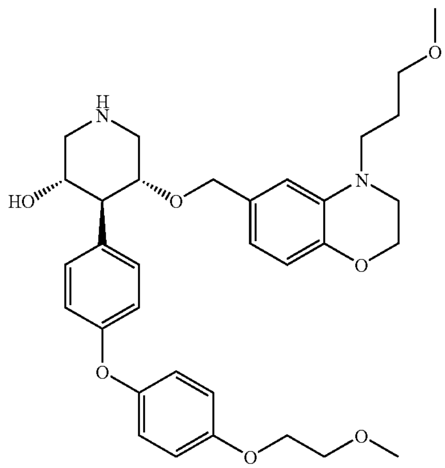 | yellowish foam | 0.19 (B) | 3.86 (I) |
| 58 | 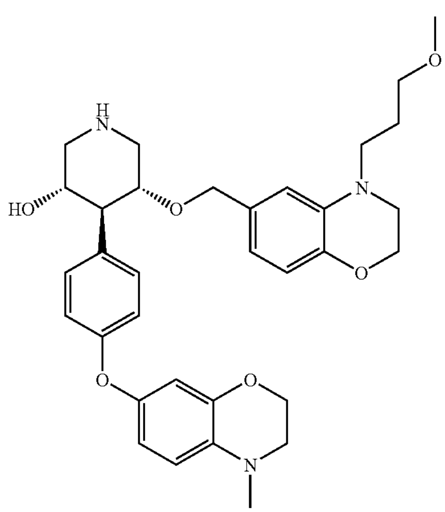 | yellowish foam | 0.16 (B) | 3.74 (I) |

-continued
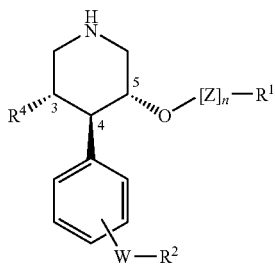
| No. | Structure | Appearance | R$_f$ (system) | Rt (method) |
|---|---|---|---|---|
| 59 | 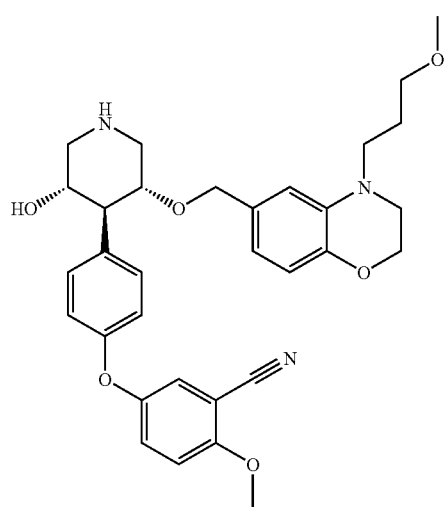 | yellowish foam | 0.16 (B) | 3.86 (I) |
| 60 | 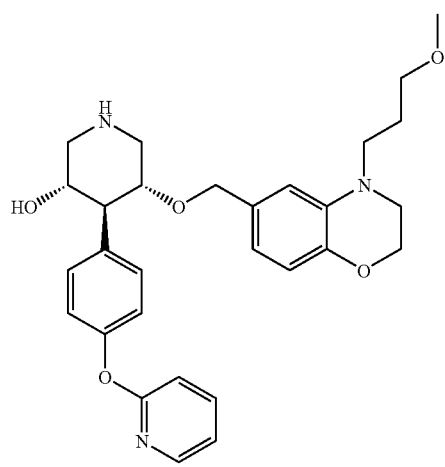 | colourless foam | 0.11 (B) | 3.49 (I) |

-continued
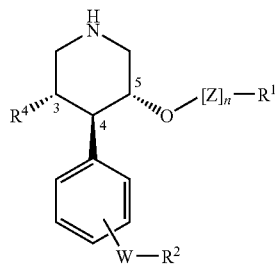
| No. | Structure | Appearance | R_f (system) | Rt (method) |
|---|---|---|---|---|
| 61 | 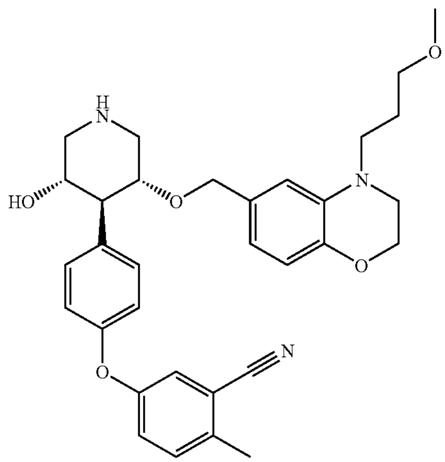 | colourless foam | 0.21 (B) | 4.04 (I) |
| 62 | 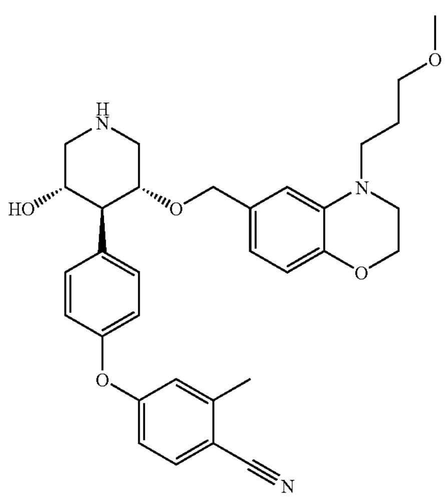 | colourless oil | 0.25 (B) | 4 (I) |

-continued
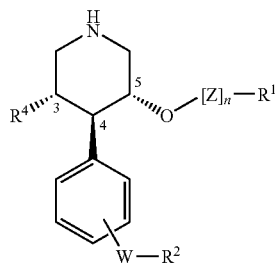
| No. | Structure | Appearance | R_f (system) | Rt (method) |
|---|---|---|---|---|
| 63 | 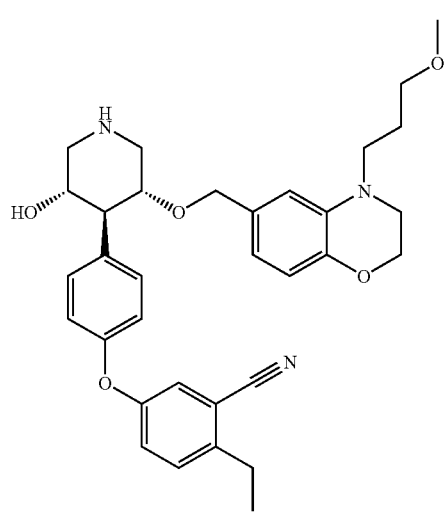 | white foam | 0.27 (B) | 4.23 (I) |
| 64 | 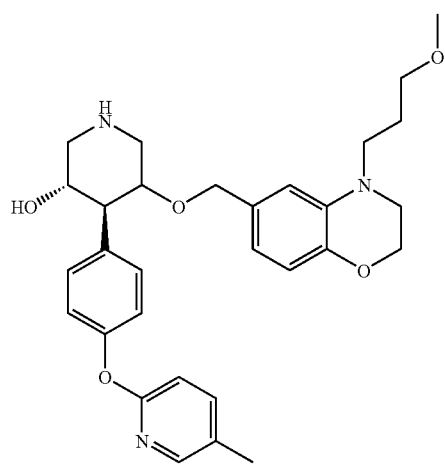 | white foam | 0.16 (B) | 3.57 (I) |

-continued
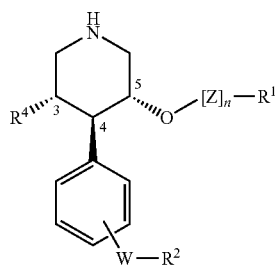
| No. | Structure | Appearance | R_f (system) | Rt (method) |
|---|---|---|---|---|
| 65 | 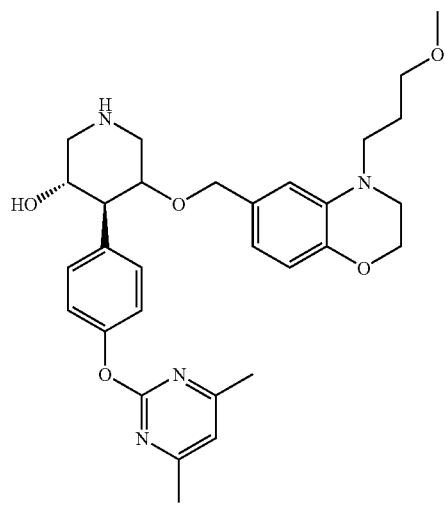 | white foam | 0.13 (B) | 3.33 (I) |
| 66 | 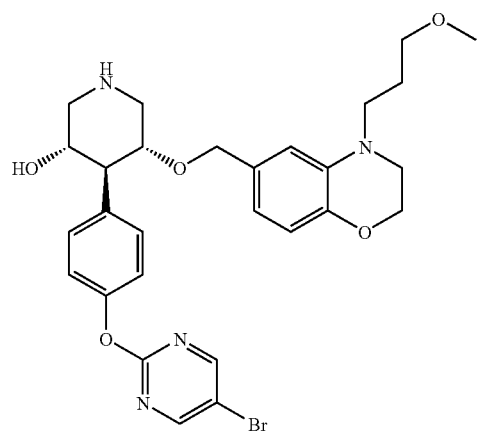 | beige wax | 0.18 (B) | 3.64 (I) |

-continued
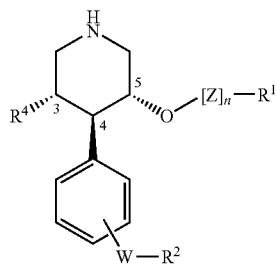
| No. | Structure | Appearance | R_f (system) | Rt (method) |
|---|---|---|---|---|
| 67 | 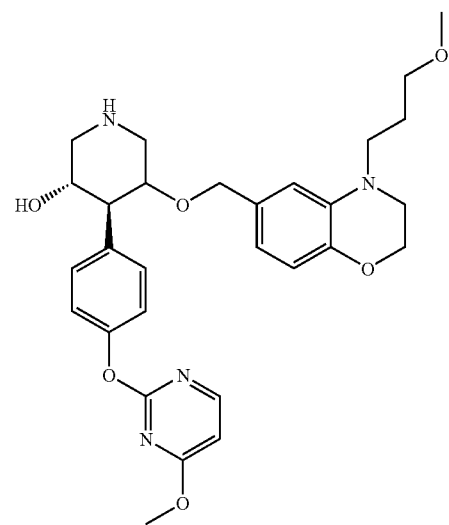 | white foam | 0.10 (B) | 3.39 (I) |
| 68 | 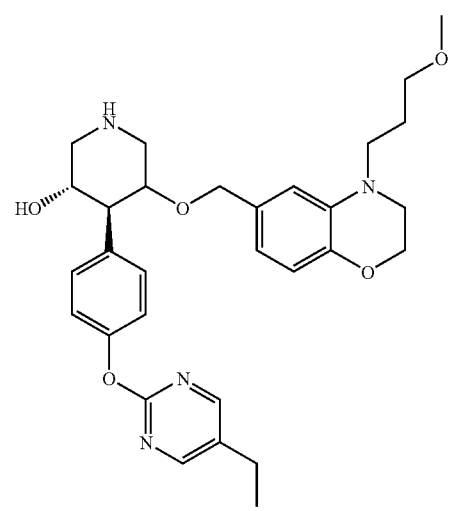 | white foam | 0.09 (B) | 3.47 (I) |

-continued
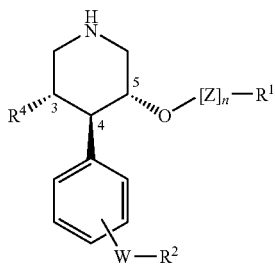
| No. | Structure | Appearance | R$_f$ (system) | Rt (method) |
|---|---|---|---|---|
| 69 | 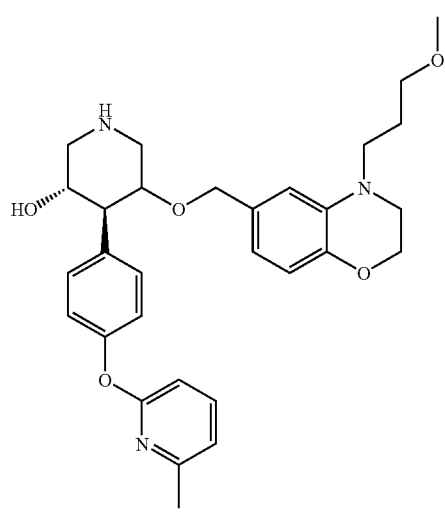 | white foam | 0.15 (B) | 3.323 (I) |
| 70 | 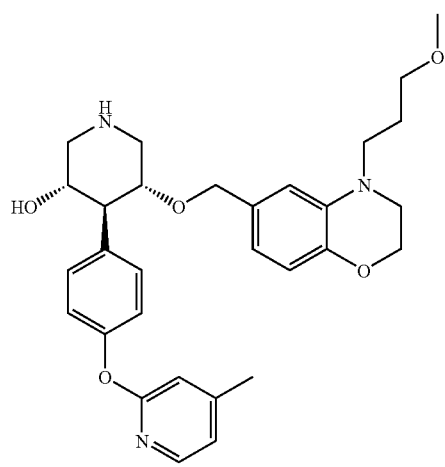 | white foam | 0.17 (B) | 3.42 (I) |

-continued
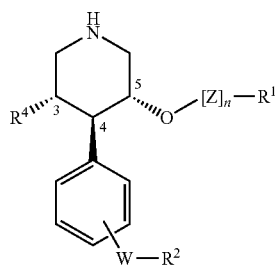
| No. | Structure | Appearance | R_f (system) | Rt (method) |
|---|---|---|---|---|
| 71 | 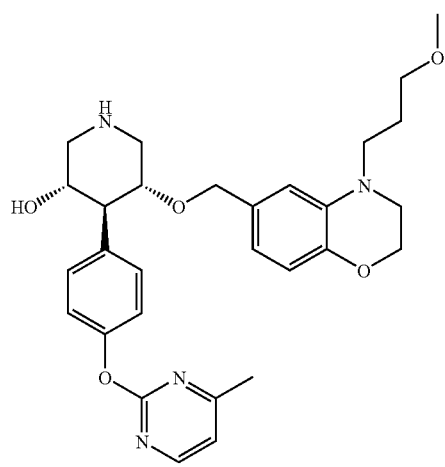 | yellowish oil | 0.31 (B) | 3.19 (I) |
| 72 | 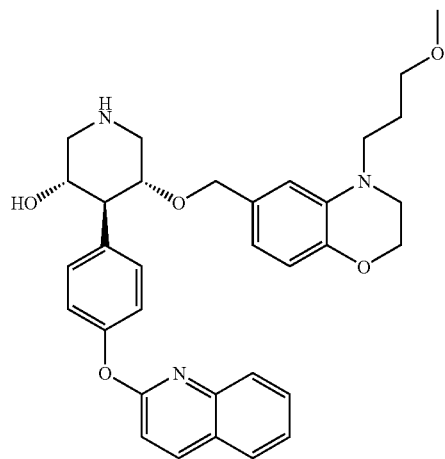 | yellowish oil | 0.30 (B) | 3.96 (I) |

-continued
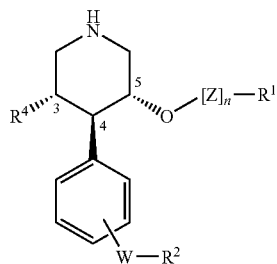
| No. | Structure | Appearance | R$_f$ (system) | Rt (method) |
|---|---|---|---|---|
| 73 | 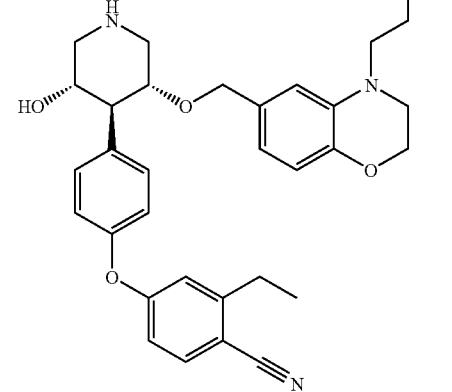 | white foam | 0.27 (B) | 4.1 (I) |
| 74 | 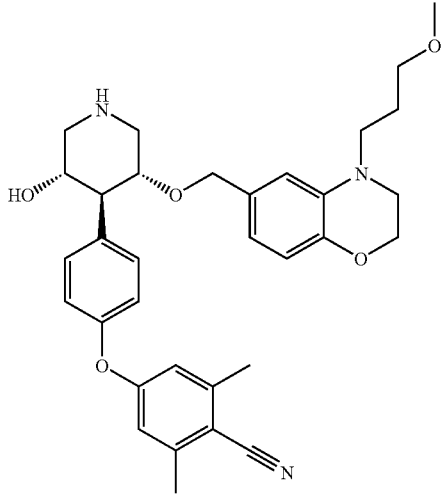 | white foam | 0.30 (B) | 4.06 (I) |

-continued
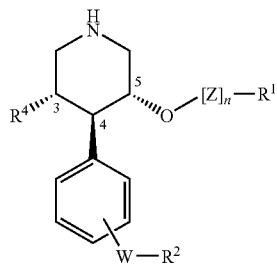
| No. | Structure | Appearance | R*f* (system) | Rt (method) |
|---|---|---|---|---|
| 75 | 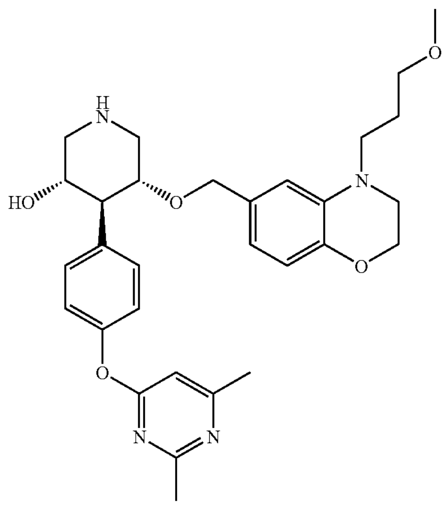 | colourless foam | 0.14 (B) | 2.799 (I) |
| 76 | 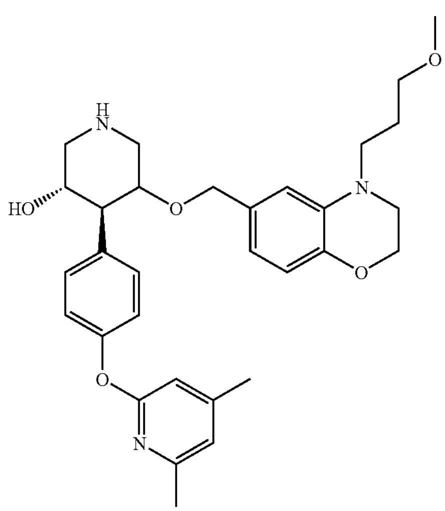 | yellowish foam | 0.27 (B) | 3.115 (I) |

-continued
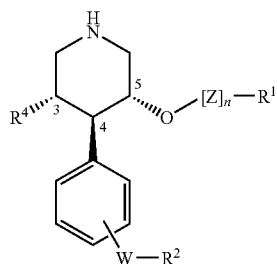
| No. | Structure | Appearance | R$_f$ (system) | Rt (method) |
|---|---|---|---|---|
| 77 | 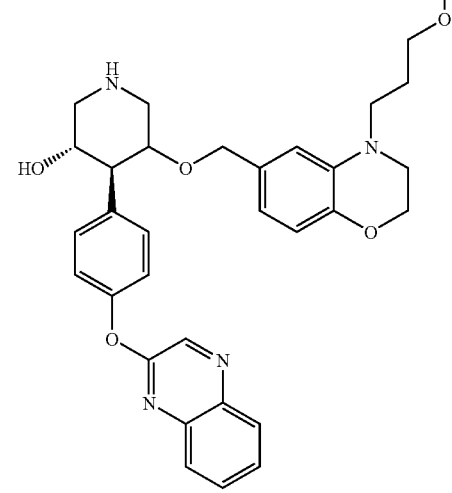 | yellowish film | 0.18 (C) | 3.768 (I) |
| 78 | 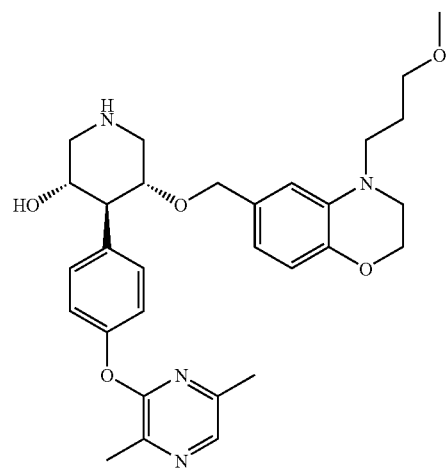 | yellowish film | 0.21 (B) | 3.456 (I) |

-continued
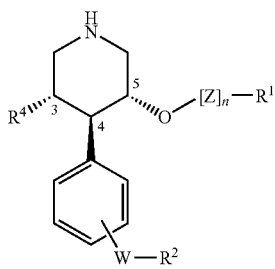
| No. | Structure | Appearance | $R_f$ (system) | Rt (method) |
|---|---|---|---|---|
| 79 | 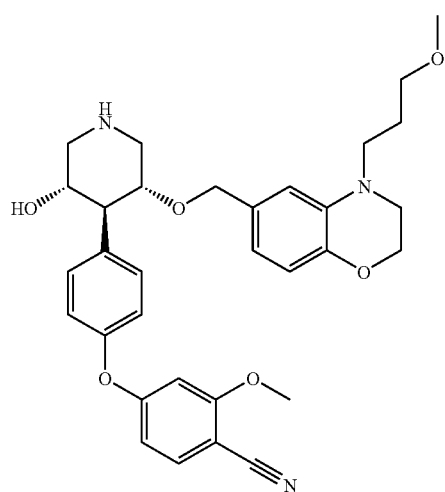 | white wax | 0.18 (B) | 3.79 (I) |
| 80 | 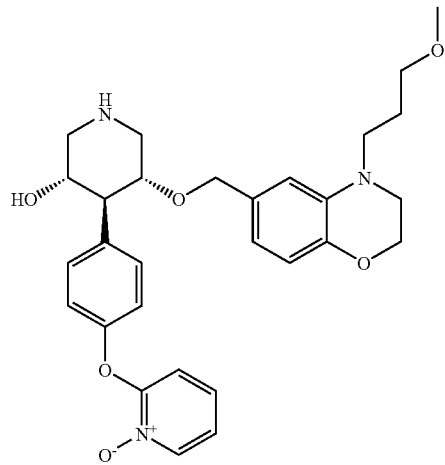 | colourless film | 0.15 (F) | 2.72 (I) |

-continued
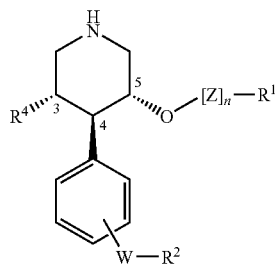
| No. | Structure | Appearance | R_f (system) | Rt (method) |
|---|---|---|---|---|
| 81 | 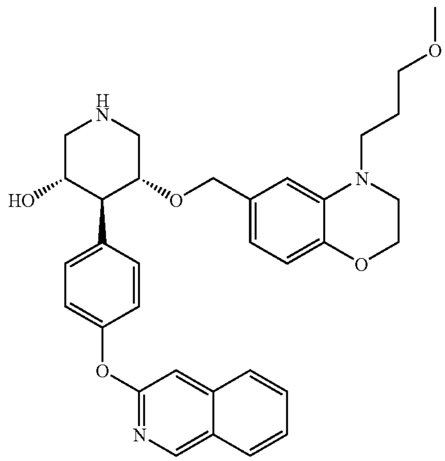 | white wax | 0.18 (B) | 3.94 (I) |
| 82 | 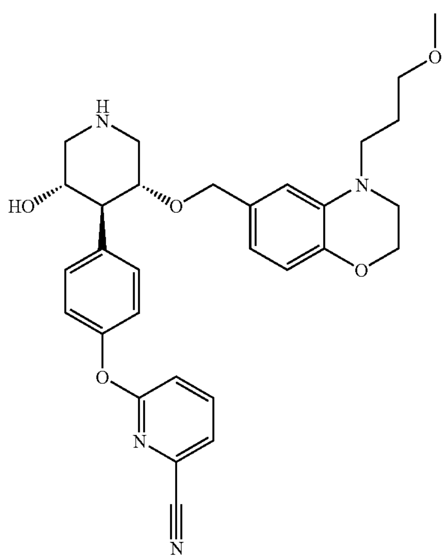 | colourless foam | 0.20 (C) | 3.59 (I) |

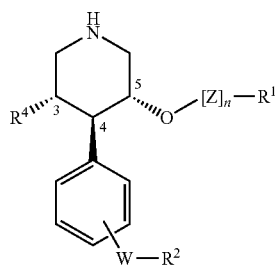
| No. | Structure | Appearance | R_f (system) | Rt (method) |
|---|---|---|---|---|
| 83 | 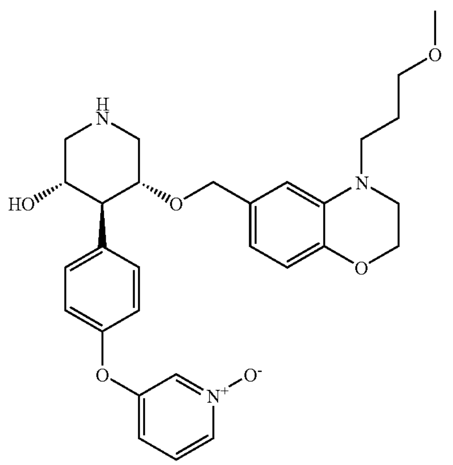 | colourless film | 0.17 (F) | 2.86 (I) |
| 84 | 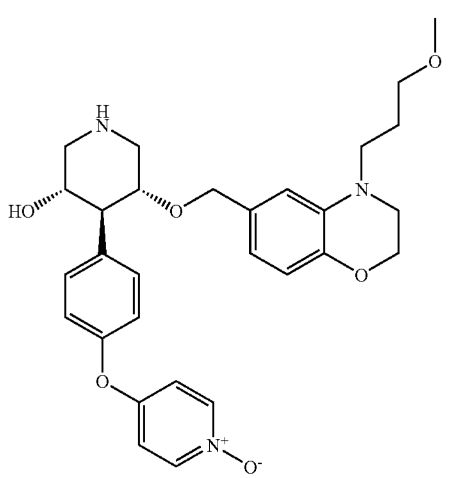 | white foam | 0.05 (B) | 2.78 (I) |

-continued

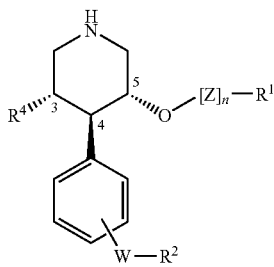

| No. | Structure | Appearance | R$_f$(system) | Rt (method) |
|---|---|---|---|---|
| 85 | 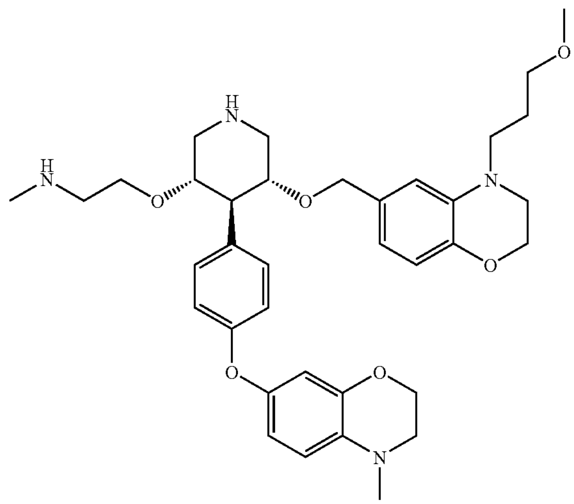 | white resin | 0.10 (G) | 3.52 (I) |

Thin-layer chromatography eluent systems:
A dichloromethanetmethanol=95:5
B dichloromethane/methanol=9:1
C dichloromethane/methanol/25% conc. ammonia=200:20:1
D dichloromethane/methanol/25% conc. ammonia=200:10:1
E dichloromethane/methanol/25% conc. ammonia=90:10:.1
F dichloromethane/methanol/25% conc. ammonia=200:40:1
G dichlordmethane/methanol/25% conc. ammonia=97:3:1
HPLC Gradients on Hypersil BDS C-18 (5 um); column: 4×1:25 mm
I 90% water*/10% acetonitrile* to 0% water*/100% acetonitrile* in 5 minutes+2.5 minutes (1.5 ml/min)
II 95% water*/5% acetonitrile* to 0% water*/100% acetonitrile* in 40 minutes (0.8 ml/min)

*contain 0.1% trifluoroacetic acid

The following abbreviations are used:

M.p. melting point (temperature)
Rf ratio of distance migrated by a substance to the distance of the solvent from the starting point in thin-layer chromatography
Rt retention time of a substance in HPLC (in minutes)

General Method A. (N-Cbz Deprotection I)

A solution of 1 mmol of "N-Cbz derivative" in 5 ml of tetrahydrofuran and 50 ml of methanol is hydrogenated in the presence of 100-200 mg Pd/C 10% at 0-20° C. for 0.5-5 hours. The reaction mixture is clarified by filtration and the filtrate is evaporated. The title compound is obtained from the residue by flash chromatography (SiO$_2$60F).

General Method B: (Alcohol Desilylation)

A solution of 1 mmol of "silyl ether" in 5 ml of tetrahydrofuran is mixed with 2.0-4.0 mmol of tetrabutylammonium fluoride (1M solution in tetrahydrofuran), and the solution is stirred at room temperature for 1-5 hours. The reaction solution is then diluted with water and extracted twice with tert-butyl methyl ether. The combined organic phases are dried over sodium sulphate and evaporated. The title compound is obtained from the residue by flash chromatography (SiO$_2$60F).

General Method C: (Phenol Arylation I)

A solution of 1 mmol of "phenol", 2-5 mmol of "boronic acid", 2.2 mmol of copper (II) acetate, 5 mmol of triethylamine or pyridine and 700-800 mg of molecular sieves (4A, powder) in 10 ml of anhydrous dichloromethane is stirred at room temperature for 12-72 hours. The reaction mixture is clarified by filtration and the filtrate is evaporated. The title compound is obtained from the residue by flash chromatography (SiO$_2$60 F).

General Method D: (Phenol Arylation II)

A solution of 1 mmol of "phenol", 3-6 mmol of "2-heteroaryl halide" and 4-6 mmol of potassium carbonate in 4 ml of anhydrous N,N-dimethylformamide is stirred at 120° C.-180° C. for 1-12 hours. The reaction mixture is clarified by filtration and the filtrate is evaporated. The title compound is obained from the residue by flash chromatography (SiO$_2$60 F).

General Method E: (N-Cbz Deprotection II)

A solution of 1 mmol of "N-Cbz derivative" in 30 ml of methanol, 10 ml of dioxane and 30 ml of 40% strength aqueous potassium hydroxide solution is stirred under reflux for 2-5 hours. 200 ml of water and 200 ml of ethyl acetate are added to the reaction mixture, and then the organic phase is separated off. The aqueous phase is extracted once with 200 ml of ethyl acetate, and the combined organic phases are dried with sodium sulphate and evaporated. The title compound is obtained from the residue by flash chromatography (SiO$_2$60 F).

Example 1

5-[4-(3-Methoxypropyl)3.4-dihydro-2H-benzo[1,4]oxazin-6-ylmethoxy]-4 -(4-phenoxyphenyl)-piperidin-3-ol The title compound is obtained as a colourless oil in analogy to Method A from 67.7 mg of benzyl 3-hydroxy-5-[4-(3-methoxypropyl)3,4-dihydro-2H-benzo[1,4]oxazin-6 -ylmethoxy]4-(4-phenoxyphenyl)piperidine-1-carboxylate.

The starting materials are prepared as follows:

a) Benzyl 3-hydroxy-5-[4-(3-methoxypropyl)3,4-dihydro-2 H-benzo[1,4]oxazin-6-ylmethoxy]-4-(4-phenoxyphenyl)piperidine-1-carboxylate The title compound is obtained as a colourless film in analogy to Method B from 103.4 mg of benzyl 3-[4-(3-methoxypropyl)3,4-dihydro-2H-benzo[1,4]oxazin-6-ylmethoxy]4-(4-phenoxy-phenyl)-5 trisopropylsilanyloxypiperidine-1-carboxylate. Rf (EtOAc/heptane 1:1)=0.20, Rt=5.30.

b) Benzyl 3-[4-(3-methoxypropyl)-3,4-dihydro-2H-benzo[1,4]oxazin-6-ylmethosy]-4-(4-phenoxyohenyl)-5 -triisopropylsilanyloxypiperidine-1-carboxylate The title compound is obtained as a colourless oil in analogy to Method C from 0.2 g of benzyl 4-(4-hydroxyphenyl)-3-[4-3-methoxypropyl)-3,4-dihydro-2H-benzo[1,4]oxazon-6-ylmethoxy]-5 -triisopropylsilanyloxypiperidine-1-carboxylate, 0.161 g of phenyl boronic acid, 0.104 g of copper (II) acetate and 0.18 ml of triethylamine. Rf (ETOAc/heptane 1.2)=0.31.

c) Benzyl 4-(4-hydroxyphenyl-3-[4-(3-methoxypropyl)-3,4-dihydro-2/h-benzol[1,4]oxazin-6-ylmethoxyl]-5 -triisopropylsilanyloxypiperdine-1-carboxylate A solution of 18.5 g of benzyl 4-(4-hydroxyphenyl)-3-[4-(3-methoxypropyl)-3-oxo-3,4-dihydro-2H-benzol [1,4]oxazin-6ylmethoxy]-5-triisopropylsilanyloxypiperidine-1-carboxylate in 250 ml of tetrahydrofuran is mixed with 125.4 ml of borane-tetrahydrofuran) complex (1M in tetra-hydrofuran and stirred at 70° C. for 1 hour (conversion checked by HPLC or DC). The reaction mixture is cooled to room temperature and, after addition of 130 ml of methanol evaporated. The title compolund is obtained as a colourless oil from the residue by flash chromatography (SiO$_2$60 F). Rf (EtOAc/heptane 1:2)=0.10.

d) Benzyl 4-(4-hydroxyphenyl)-3-[4-(3-methoxypropyl)-3-oxo-3,4-dihydro-2H-benzo[1,4]oxazin-6-ylmethoxyl]-5 -triisopropylsilanyloxypiperidine-1-carboxylate 2.42 g of tetrakis(triphenylphosphine)palladium(0) are added to a solution of 22.6 g of benzyl 4-(4-allyloxyphenyl)-3-[4-(3-methoxypropyl)-3-oxo-3,4-dhydro-2benzo[1,4]ox-azin-6-ylmethoxy]-5 -triisopropylsilanyloxypiperidine-1-carboxylate in 440ml of methanol under argon. After 5 minutes, 11.71 g of potassium carbonate are added, and the reaction mixture is stirred at room temperature for 4 hours (conversion checked by HPLC or DC). The solvept is then removed in vacuo, and the residue is mixed with 500 ml of water and extracted twice with 500 ml of tert-butyl methyl ether each time. The combined organic phases are washed once with 500 ml of water and 500 ml of brine. The organic phase is dried with sodium sulphate and evaporated. The title compound (19.59 g) is obtained as a yellow resin from the residue by flash chromatography (SiO$_2$60 F). Rf (EtOAc/heptane 1:1)=0.22.

e) Benzyl 4-(4-allyloxyphenyl)-3-[4-(3-methoxypropyl)-3-oxo-3,4-dihydro-2H-benzo[1,4]oxazin-6ylmethoxy]-5 -triisopropylsilanyloxypiperidine-1-carboxylate 1.61 g of sodium hydride dispersion (60%) are added to a solution of 19.76 g of benzyl 4-(4-allyloxyphenyl)-3-hydroxy-5 -triisopropylsilanyloxypiperidine-1-carboxylate and 9.95 g of 6-chloromethyl-4-(3-methoxypropyl)-4H-benz[1,4]-oxazin-3-one in 285 ml of N,N-dimethylformamide while the reaction mixture is stirred at 10° C. for 1 hour and at room temperature for 18 hours. The mixture is poured into 1M aqueous sodium bicarbonate solution (700 ml) and extracted with tert-butyl methyl ether 2×800 ml). The organic phases are washed successively with water (2×500 ml) and brine (1×500 ml), dried with sodium sulphate and evaporated. The title compound is obtained from the residue by flash chromatography (SiO$_2$60 F). Rf (EtOAc/heptane 2:3)=0.30, Rt=7.15.

f) Benzyl 4-(4-allyloxyphenyl)-3-hydroxy-5-triisopropylsilanyloxypiperidine-1carboxylate A mixture of 25.0 g of benzyl 3-hydroxy-4-(4hydroxyphenyl)-5-triisopropylsilanyloxypiperidine-1carboxylatebo in 350 ml of N,N-dimethylformamide is stirred with 13.9 g of potassium carbonate and 7.0 ml of allyl bromide at 70° C. for 24 hours. The reaction mixture is clarified by filtration and the filtrate is evaporated. The residue is mixed with water (750 ml) and extracted with ethyl acetate (2×750 ml). The combined organic phases are washed with brine (1×750 ml), dried with sodium sulphate and evaporated. The title compound is obtained from the residue by flash chromatography (SiO$_2$60 F). Rf (EtOAc/heptane 1:2)=0.28; Rt=6.54 g) Benzyl 3-hydroxy-4-(4-hydroxyphenyl)-5-triisopropylsilanyloxypiperidine-1-carboxylate 90 ml of saturated aqueous sodium bicarbonate solution and -1.57 ml of benzyl chloroformate are added to a solution of 3.140 g of 4-(4-hydroxyphenyl-5-triisoproylsilanyoxyperidin-3-ol in 90 ml of ethyl acetate. The mixture is vigorously stirred for 30 minutes, and the phases are then separated. The aqueous phase is back-extracted with 100 ml of ethyl acetate, and the combined organic phases are dried over sodium sulphate and evaporated. The title compound is obtained as a colourless solid from the residue by flash chromatography (SiO$_2$F60). Rf (dichloromethane/methanol/25% conc. ammonia 200:20:1)=0.49; Rt=5.89.

h) (4-(4-Hydroxyphenyl)-5-triisopropylsilanyloxypiperiden-3-ol

A solution of 113.0 g of 4-(4-benzyloxyphenyl)-1-(1-phenylethyl-5-triisopropylsilanyloxy-piperidin-3-ol in 1.51 of methanol is hydrogenated in the presence of 8.5 g of Pd/C 10% at room temperature for 8 hours. The reaction mixture is clarified by filtration and the filtrate is evaporated. The title compound is obtained as a colourless solid from the residue by flash chromatography (SiO$_2$60 F). Rf(dichloromethane/methahol/25% conc.ammonia 200:20.1)=0.19; Rt=3.80.

i) 4-(4-Benzyloxyphenyl)-1-(1-phenylethyl)-5-triisopropylsilanyloxypiperidin-3ol 150 ml of borane-tethrahydrofuran comprex (1M in tetrahydrofuran) are added dropwise to a solution of 20.00 g 4-(4-benzyloxypheny)-(1-(1-phenylethyl)-3-triisopropylsilanyloxy- 1,2,3,4-tetrahydropyridine in 280 ml of 1,2dimethoxyethane at 0° C. The reaction solution is then stirred at 30° C. for 3 hours. The solution is cooled to room temperature and hydrolysed with 70 ml of water. The hydrolysed solution is stirred for 5 minutes and then 56.00 g of sodium percarbonate are added, and the suspension is stirred at 50° C. for 1 hour. The reaction mixture is poured into 600 ml of water and extracted with 2×500 ml of ethyl acetate. The combined organic phases are washed with 400 ml each of water and brine and evaporated. The title compound is obtained as a yellowish oil from the residue by flash chromatography (SiO$_2$ F60). Rf (EtOAc/heptane 1:2)=0.23; Rt=5.75.

j) 4-(4-Benzyloxyphenyl)-1-(1-phenylethyl)-3-triisopropylsilanyloxy-1,2,3,4-tetrahydro-pyridine A suspension of 14.70 g of 4-(4-benzyloxyphenyl)-1-(1-phenylethyl)-1,2,3,4-tetrahydro-pyridin-3-ol [257928-45-3] in 250 ml of dichloromethane is mixed with 6.80 ml of 2,6-lutidine and cooled to 0° C. 12.60 ml of triisopropysilyl trifluoromethanesulphonate are added dropwise, and the reaction mixture is stirred at 0° C. for 1 hour. The reaction solution is poured into 400 ml of water, and the phases are separated. The aqueous phase is back-extracted with 200 ml of dichloromethane, and the combined organic phases are dried with sodium sulphate and evaporated. The title compound is obtained as a yellow-brown oil from the residue by flash chromatography (SiO$_2$ F60). Rf (EtOAc/heptane 1:2)= 0.66; Rt=5.83.

k) 6-Chloromethyl-4-(3-methoxypropyl)-4H-benz [(1,4]-oxazin-3-one

A solution of 10.05 g of 6-hydroxymethyl-4-(3-methoxypropyl)-4H-benzo[1,4]oxazin-3-one in 6.40 ml of pyridine and 100 ml of dichloromethane is slowiy added dropwise at 0-5° C. to a precooled solution of 7.65 ml of thionyl chloriode in 20 ml of dichloromethane. The reaction mixture is stirred for 1 hour each at 0° C. and then at room temperature, and subsequently poured into 200 ml of ice-water. The mixture is extracted with dichloromethane (2×200 ml). The organic phases are washed successively with 1M aqueous sodium bicarbonate solution (2×200 ml) and brine, dried with sodium, sulphate and evaporated. The title compound is obtained as a colourless oil from the residue by flaash chromatography (SiO$_2$ 60 F). Rf (EtOAc/heptane 2:1)=0.60; Rt=4.05.

l) 6-Hydroxymethyl-4-(3-methoxypropyl)-4H-benzo [1,4]oxazin-3-one

A suspension of 1.79 g of 6-hydroxymethyl-4H-benzo[1, 4]oxazin-3-one, 2.20 ml of 1-chloro-3-methoxypropane, 10 g of KF on aluminium oxide and 0.033 g of potassium iodid in 150 ml of acetonitrile is stirred under reflux for 72 hours. The reaction mixture is cooled and clarified by filtration, and the filltrate is evaporated to dryness. The title compound is obtained from the residue by flash chromatography (SiO$_2$ 60 F). Rf (CH$_2$Cl$_2$/MeOH 9:1)=0.60; Rt =2.74.

m),6-1Hydroxymethyl-4H-benzo[1,4]oxazin-3-one

A mixture of 6.9 g of methyl 3-oxo-3,4-dihydro-2H-benzo [1,4]oxazine-6-carboxylate in 230 ml of tetrahydrofuran is cooled to −40° C. 88.9 ml of diisobutylaluminium hydride (1.5M in toluene) are added dropwise at −40° C. over the course of 30 minutes. The reaction mixture is stirred at −40° C. to −20° C. for 1.5 hours and then cautiously poured into 150 ml of 2N HCl (cold). The organic phase is separated off, and the aqueous phase is extracted with tetrahydrofuran (5×100 ml). The organic phases are washed with brine (1×100 ml), filtered through cotton wool and evaporated. The title compound is obtained as beige crystals from the residue by crystallization (from ethanol). Rf=0.16 (EtOAc/heptane 2.1); Rt=2.23; m.p.: 186-187° C.

The following compounds are prepared in an analogous manner to the process described in Example 1:

2  4-[4-(3-Methoxyphenoxy)phenyl]-5-[4-(3-methoxypropyl)-3,4-dihydro-2H-benzo[1,4]oxazin-6 -ylmethoxy]piperidin-3-ol 3  4-[4-(3-Ethoxyphenoxy)phenyl]-5-[4-(3-methoxypropyl)-3,4-dihydro-2H-benzo[1,4]oxazin-6 -ylmethoxy]piperidin-3-ol 4  4-[4-(3-Fluorophenoxy)phenyl]-5-[4-(3-methoxypropyl)-3,4-dihydro-2H-benzo[1,4]oxazin-6 -ylmethoxy]piperidin-3-ol 5  4-[4-(3-Fluorophenoxy)phenyl]-5-[4-(3-methoxypropyl)-3,4-dihydro-2H-benzo[1,4]oxazin-6 -ylmethoxy]piperidin-3-ol 6  5-[4-(3-Methoxypropyl)-3,4-dihydro-2H-benzo[1,4]oxazin-6-ylmethoxy]-4-[4-(3 -trifluoromethylphenoxy)phenyl]piperidin-3-ol 7  5-[4-(3-Methoxypropyl)-3,4-dihydro-2H-benzo[1,4]oxazin-6-ylmethoxy]-4-[4-(3 -trifluoromethylphenoxy)phenyl]piperidin-3-ol 11  5-[4-(3-Methoxypropyl)-3,4-dihydro-2H-benzo[1,4]oxazin-6-ylmethoxy]-4-(4-o-tolyloxyphenyl)piperidin-3-ol 12  5-[4-(3-Methoxypropyl)-3,4-dihydro-2H-benzo[1,4]oxazin-6-ylmethoxy]-4-[4-(4-trifluoromethylphenoxy)phenoxy) phenyl]piperidin-3-ol 13  5-[4-(3-Methoxyphenoxy)-3,4-dihydro-2H-benzo[1,4]oxazin-6ylmethoxy]-4-(4-m-tolyloxyphenyl)piperidin-3-ol 15  4-[4-(3-Ethylphenoxy)phenyl]-5-[4-(3-methoxypropyl)-3,4-dihydro-2H-benzo[1,4]oxazin-6-ylmethoxy ]piperidin-3-ol 16  5-[4-(3-Methoxypropyl)-3,4-dihydro-2H-benzo[1,4]oxazin-6ylmethoxy]piperdin-4-(4-p-tolyloxyphenyl)piperidin-3-ol 17  4-{4-[3-(2-Methoxyethoxy)phenoxy]phenyl}-5-[4-(3-methoxypropyl)-3,4-dihydro-2H-benzo[1,4]oxazin-6 -ylmethoxy]piperidin-3-ol 18  1-[4-(4-{3-Hydroxy-5-[4-(3-methoxypropyl)-3,4-dihydro-2H-benzo[1,4]oxazin-6-ylmethoxy]piperidin-4 -yl}phenoxy)phenyl]ethanone 19  4-[4-(1H-Indol-5-yloxy-phenyl]-5-[4-(3-methoxypropyl)-3,4-dihydro-2H-benzo[1,4]oxazin-6-ylmethoxy]piperidin-3-ol 21  4-[4-(Benzo[1,3]dioxol-5yloxy)phenyl]-5-[4-(3-methoxypropyl)-3,4-dihydro-2H-benzo[1,4]oxazin-6 -ylmethoxy]piperdin-3-ol 22  4-[4-(4-Methoxyphenoxy)phenyl]-5-[4-(3-methoxypropyl)-3,4-dihydro-2H-benzo[1,4]oxazin-6-ylmethoxy]piperidin-3-ol 23  4-[4-(3-Dimethylaminophenoxy)phenyl]-5-[4-(3-methoxypropyl)-3,4-dihydro-2H-benzo[1,4]oxazin-6-ylmethoxy]piperidin-3-ol 24  4-(4-{3-Hydroxy-5-[4-(3-methoxypropyl)-3,4-dihydro-2H-benzo[1,4]oxazin-6-ylmethoxy]piperidin-4-yl}phenoxy)benzonitrile 25  4-[4-(4-Ethylphenoxy)phenyl]-5-[4-(3-methoxypropyl)-3,4-dihydro-2H-benzo[1,4]oxazin-6-ylmethoxy]piperidin-3-ol 26  4-[4-(4-Methoxy-3methylphenoxy)phenyl]-5-[4-(3-methoxypropyl)-3,4-dihydro-2H-benzo[1,4]oxazin-6 -ylmethoxy]piperidin-3-ol 27  5-[4-(3-Methoxypropyl)-3,4-dihydro-2H-benzo[1,4]oxazin-6-ylmethoxy]-4-[4-(1-methyl-1H-indol-5-yloxy)phenyl ]piperidin-3-ol 28  4-[4-(2,3-Dihydrobenzo[1,4]dioxin-6-yloxy)phenyl]-5-[4-(3-methoxypropyl)-3,4-dihydro-2H-benzo[1,4]oxazin-6 ylmethoxy]piperidin-3-ol 29  4-[4-(2,3-Dihydrobenzofuran-5-yloxy)phenyl]-5-[4-(3-methoxypropyl)-3,4-dihydro-2H-benzo[1,4]oxazin-6 ylmethoxy]piperdin-3-ol 30  4-[4-(3,4-Dimethylphenoxy)phenyl]-5-[4-(3-methoxypropyl)-3,4-dihydro-2H-benzo[1,4]oxazin-6-ylmethoxy]piperidin-3-ol 32  4-[4-(Benzofuran-5-yloxy)phenyl]-5-[4-(3-methoxypropyl)-3,4-dihydro-2H-benzo[1,4]oxazin-6-ylmethoxy]piperidin-3-ol 33  4-[4-(3,4-Dimethoxyphenoxy)phenyl]-5-[4-(3-methoxypropyl)-3,4-dihydro-2H-benzo[1,4]oxazin-6-ylmethoxy]piperidin-3-ol 34  4-[4-(4-Isopropylphenoxy)phenyl]-5-[4-(3-methoxypropyl)-3,4-dihydro-2H-benzo[1,4]oxazin-6-ylmethoxy]piperidin-3-ol 35  4-[4-(4-Isopropoxyphenoxy)phenyl]-5-[4-(3-methoxypropyl)-3,4-dihydro-2H-benzo[1,4]oxazin-6-ylmethoxy]piperidin-3-ol 38  4-[4-(3-Isopropylphenoxy)phenyl]-5-[4-(3-methoxypropyl)-3,4-dihydro-2H-benzo[1,4]oxazin-6-ylmethoxy]piperidin-3-ol 39  3-(4-[3-Hydroxy-5-[4-(3-methoxypropyl)3,4dihydro-2H-benzo[1,4]oxazin-6-ylmethoxy]piperidin-4-yl]phenoxy)benzonitrile 40  N-[4-(4-[3-Hydroxy-5-[4-(3-methoxypropyl)-3,4-dihydro-2H-benzo[1,4]oxazin-6-ylmethoxy]piperidin-4 -yl]phenoxy)phenyl]acetamide 46  4-[4-(4-Ethoxyphenoxy)phenyl]-5-[4-(3-methoxypropyl)-3,4-dihydro-2H-benzo[1,4]oxazin-6-ylmethoxy]piperidin-3-ol 47  4-[4-(3-Hydroxy-5[4-(3-methoxypropyl)-3,4-dihydro-2H-benzo[1,4]oxazin-6-ylmethoxy]piperidin-4 -yl]phenoxy)-N,N-dimethylbenzamide 48  4-[4-(3-Hydroxy-5[4-(3-methoxypropyl)-3,4-dihydro-2H-benzo[1,4]oxazin-6-ylmethoxy]piperidin-4 -yl]phenoxy)-N-methylbenzamide 49  4-[4-(3-Hydroxy-5[4-(3-methoxypropyl)-3,4-dihydro-2H-benzo[1,4]oxazin-6-ylmethoxy]piperidin-4-yl]phenoxy)benzamide 50  5-[4-(3-Methoxypropyl)-3,4-dihydro-2H-benzo[1,4]oxazin-6-ylmethoxy]-4-[4-(pyridin-3-yloxy)phenyl]piperidin-3ol 51  4-[4-(4-Methoxymethylphenoxy)phenyl]-5-[4-(3-methoxypropyl)-3,4-dihydro-2H-benzo[1,4]oxazin-6-ylmethoxy]piperdin-3-ol 52  4-[4-(4-Dimethylaminophenoxy)phenyl]-5-[4-(3-methoxypropyl)-3,4-dihydro-2H-benzo[1,4]oxazin-6-ylmethoxy]piperdin-3-ol 53  5-[4-(3-Methoxypropyl)-3,4-dihydro-2H-benzo[1,4]oxazin-6-ylmethoxy]4-[4-(pyridin-4-yloxy)phenyl]piperidin-3-ol 54  4-[4-(4-Methanesulphonylphenoxy)phenyl]-5-[4-(3-methoxypropyl)-3,4-dihydro-2H-benzo[1,4]oxazin-6-ylmethoxy]piperidin-3-ol 55  4-{4-[4-(3-Methoxypropoxy)phenoxy]phenyl}-5-[4-(3-methoxypropyl)-3,4-dihydro-2H-benzo[1,4]oxazin-6 -ylmethoxy]piperidin-3-ol 57  4-{4-[4-(2-Methoxyethoxy)phenoxy]phenyl}-5-[4-(3-methoxypropyl)-3,4-dihydro-2H-benzo[1,4]oxazin-6 -ylmethoxy]piperidin-3-ol 58  5-[4-(3-Methoxypropyl)-3,4-dihydro-2H-benzo[1,4]oxazin-6ylmethoxy]piperdin-4-[4-(4-methyl-3,4 dihydro-2H-benzo[1,4]oxazin-7-yloxy)phenyl]piperidin-3-ol 79  4-(4-{3-Hydroxy-5-[4-(3-methoxypropyl)-3,4-dihydro-2H-benzo[1,4]oxazin-6ylmethoxy]piperidin-4 -yl}phenoxy)-2-methoxybenzonitrile Example 9

4-{4-[4-(1-Hydroxy-1methylethyl)phenoxy]phenyl}-5-[4-(3-methoxypropyl)-3,4-dihydro-2H-benzo[1,4 ]oxazin-6-ylmethoxy]piperidin-3ol The title compound is obtained as a colourless film in anaolgy to Method A from 22.6 mg of benzyl 3-hydroxy-4-[4-[4-(1-hydroxy-1-methylethyl)phenoxy]phenyl)-5-[4-(3-methoxypropyl)-3,4 -dihydro-2H-benzo[1,4]oxazin-6-ylmethoxy]piperidine-1-carboxylate.

The starting materials are prepared as follows.

a) Benzyl 3-hydroxy-4-{4-[4-(1-hydroxy-1-methylethyl)phenoxy]phenyl}-5-[4-(3-methoxypropyl)-3,4 -dihydro-2H-benzo[1,4]oxazin-6-ylmethoxy]piperidine-1-carboxylate 0.06 ml of methylmagnesium bromide solution (3M solution in diethyl ether) is added dropwise to a solution of 49 mg of benzyl 4-[4-4-acetylphenoxy)phenyl]-3-hydroxy-5-[4-3-methoxypropyl)-3,4 -dihydro-2H-benzo[1,4]oxazin-6-ylmethoxy]piperidine-1carboxylate in 0.3 ml of tetrahydrofuran under argon at room temperature and stirred for 2 hours. 3 ml of 0.5M aqueous HCl solution are added to the reaction mixture, and it is extracted with 15 ml of ethyl acetate. The organic phase is separated off, dried with sodium sulphate and evaporated. The title compound is obtained from the residue by flash chromatography (SiO$_2$ 60F). Rf (EtOAc/heptane 3:1)= 0.22; Rt=4.84.

b) Benzyl 4-[4-(4-acetylphenoxy)phenyl]-3-hydroxy-5-[4-(3-methoxypropyl)-3,4dihydro-2H-benzo[1,4 ]oxazin-6-ylmethoxy]piperidine-1-carboxylate The title compound is obtained as a colourless film in analogy to Method B from 187.3 mg of benzyl 4-[4-(4-acetylphenoxy)phenyl]-3-[4-(3-methoxpropyl)-3,4-dihyro-2H- benzo[1,4]oxazin-6 -ylmethoxy]5-triisopropylsilanyloxypiperidine-1carboxylate Rf (EtOAc/heptane 3:1)=0.24; Rt=4.97.

c) Benzyl 4-[4-(4-acetylphenoxy)phenyl]-3-[4-(3-methoxypropyl)-3,4-dihydro-2H-benzo[1,4]oxazin-6 -ylmethoxy]-5-triisopropylsilanyloxypiperidine-1-carboxylate The title compound is obtained as a colourless oil analogy to Method C from 0.2 g of benzyl, 4-(4-hydroxyphenyl)-3-[4-(3-methoxypropyl)-3,4-dihydro-2H-benzo[1,4]oxazin-6-ylmethoxy]-5 -triisopropylsilanyloxypiperidine-1carboxylate (Example 1C), 0.245 g of 4-(acetylphenylboronic acid, 0.113 g of copper(II) acetate and 0.19 ml of triethylamine, Rf (EtOAc/heptane 1:2)=0.16.

The following compound is prepared in an analogous manner to the process described in Example 9:
10 4-[4-[4(1 -Methoxy-1-methylethyl)phenoxy]pheny]-5-[4-(3-methoxypropyl)-3,4-dihydro-2H-benzo[1,4 ]oxazin-6ylmethoxy]piperidin-3ol Example 14

4-{4-[3-(3-methoxypropoxy)phenoxy]phenyl}-5-[4-(3methoxypropyl)-3,4-dihydro-2H-benzo[1,4 ]oxazin-6-ylmethoxyl]piperidin-3-ol The title compound is obtained as a colourless oil in analogy to Example 1 in 3 steps (Methods A, B and C) from 0.2 g of benzyl 4-(4-hydroxphenyl)-3-[4-(3methoxypropyl)-3,4-dihydro-2H-benzo[1,4 ]oxazin-6-ylmethoxyl]-5triisopropylsilanyloxypiperidine-1-carboxylate (Example 1c), 0.3254 g of 3 -(3methoxypropoxy)phenylboronic acid, 0.1134 g of copper(II) acetate acid 0.19 ml of triethylamine.

The startingi materials are prepared as follows:

a) 3-(3-Methoxypropoxy)phenylboronic acid 6.71 ml of n-butyllithium solution (1.6M in hexane) are added dropwise to a solution of 2.5 g of 1 -bromo-3-(3-methoxypropoxy)benzene in 14 ml of dry tetrahydrofuran at −78° C. After stirring at this temperature for 15 minutes, 2.78 ml of triisopropyl borate are added, and the mixture is then slowly warmed to room temperature, 20 ml of 1N ,HCl and 5 ml of conc. HCl are added to the reaction mixture, and the organic solvents are evaporated off in vacuo. The precipitate which has separated out is filtered off with suction and washed twice with ice-water. Drying under high vacuum affords 0.987 g of the title compound as a yellowish brown solid. Rt=3.04.

b) 1 -Bromo-3-(3-methoxvpropoxy)benzene

A mixture of 5.0 g of 3-bromophenol, 7.99 g of potassium carbonate and 3.77 g of 1-chloro-3-methoxypropane in 90 ml of dimethylformamide is stirred at 100° C. for 4.5 hours. The reaction mixture is clarified by filtration and the filtrate is evaporated in vacuo. The residue is taken up in 100 ml of tert-butyl methyl ether, and the organic phase is washed once each wit 50 ml of 1N NaOH, 50 ml of water and 50 ml of brine. The organic phase is dried with sodium sulphate, filtered and evaporated. 7.08 g of the title compound are obtained as an orange oil. Rt=4.91.

Example 59

5-(4{3-Hydroxy-5-[4-(3-methoxypropyl)3,4-dihydro-2H-benzo[1,4]oxazin-6-ylmethoxy]-piperidin-4 -yl}phenoxy)-2-methoxybenzonitrile The title compound is obtained as a yellowish foam in analogy to Example 1 in 3 steps (Methods A, B and C) from 0.2 g of benzyl 4-(4-hydroxyphenyl)-3-[4-(3methoxypropyl)-3,4 -dihydro-2H-benzo[1,4]oxazin-6ylmethoxy]-5-triisopropylsilanyloxypiperidin-1carboxylate (Example 1c), 0.2604 g of 3-cyano-4methoxyphenylboronic acid, 0.1134 g of copper(II) acetate and 0.19 ml of triethylamine.

The starting material is prepared as follows a) 3-Cyano-4-methoxyphenylboronic acid 16.23 ml of n-butyllithium solution (1.6M in hexane) are added dropwise to a solution of 5.00 g of 5-bromo-2-methoxybenzonitrile in 90 ml of dry tetrahydrofuran at −78° C. After stirring at this temperature for 45 minutes, 6.71 ml of triisopropylborate are added, and the mixture is then slowly warmed to −20° C. 50 ml of 1N HCl are added to the reaction mixture. The phase is separated and the aqueous phase is extracted three more times with 100 ml of diethyl ether each time. The combihled organic phases are dried with sodium sulphate, filtered and evaporated. The remaining oil is mixed with pentane, and the precipitate which separates out is filtered off with suction and washed once with a little dichloromethane. Drying under high vacuum affords the title compound as a white solid. Rt=2.74.

Example 61

5-(4-{3-Hydroxy-5-4-(3-methoxypropyl-3,4-dihydro-2H-benzo[1,4 ]oxazin-6-ylmethoxyl-piperidin-4-yl}phenoxy)2-methylbenzonitrile The title compound is obtained as a yellow foam in analogy to Example 1 in 3 steps (Methods A, B and C) from 0.2 g of benzyl 4-(4-hydroxphenyl)-3-[4 -(3-methoxypropyl)-3,4-dihydro-2H-benzo[1,4]oxazin-6ylmethoxy]-5 -triisopropylsilanyloxypiperidine-1-carboxylate (Example 1c), 0.2293 g of 3-cyano-4methylphenylboronic acid, 0.1134 g of copper(II) acetate and 0.19 ml of triethylamine.

The starting material is prepared as follows:

a) 3-Cyano-4-methylphenylboronic acid 17.5 ml of n-butyllithium solution (1.6M in hexane) are added dropwise to a solution of 5 g of 5-bromo-2-methylbenzonitrile in 80 ml of dry tetrahydrofuran at −78° C. After stirring at this temperature for 35 minutes, 7.3 ml of triisopropyl borate are added. After one hour, 50 ml of 1N HCl are added to the reaction mixture at −78° C., and the mixture is warmed to room temperature. The phases are separated and the aqueous phase is extracted three more times with 100 ml of diethyl ether each time. The combined organic phases are dried with sodium sulphate, and the solvent is concentrated to 5 ml. The residue is mixed with 150 ml of pentane. The precipitate which has separated out is filtered off with suction and washed twice with pentane. Drying under high vacuum results in 2.85 g of the title compond as a pale yellow solid. Rt=2.98.

Example 62

4-(4-{3-Hydroxy-5-[4-(3-methoxypropyl)-3,4-dihydro-2H-benzo[1,4]oxazin-6-ylmethoxyl]-piperidin-4-yl}phenoxy)-2-methylbenzonitrile The title compound is obtained as a colourless oil in analogy to Example 1 in 3 steps (Methods A, B and C) from 0.2 g of benzyl 4-(4-hydroxyphenyl)-3-[4-(3-methoxypropyl)-3,4-dihydro-2H-benzo[1,4]oxazin-6-ylmethoxy]-5-triisopropylsilanyloxypiperidine-1carboxylate (Example 1c), 0.0923 g of 4-cyano-3-methylphenylboronic acid, 0.1134 g of copper(II) acetate and 0.12 ml of pyridine.

The starting material is prepared as follows:

a) 4-Cyano-3-methylphenylboronic acid 10.21 ml of n-butyllithium solution (1.6M in hexane) are added dropwise to a solution of 3.00 g of 4-bromo-2-methylbenzonitrile in 50 ml of dry tetrahydrofuran at −78° C. after stirring at this temperature for 30 minutes, 4.22 ml of triisopropyl borate are added, and then the mixture is stirred at −78° C. for a further 45 minutes. 30 ml of 1N are added to the reaction mixture. The phases are separated and the aqueeous phase is extracted three more times with 100 ml of diethyl ether/tetrahydrofuran (1,1) each time. The combined organic phases are dried with sodium sulphate, filtered and concentrated to 4 ml in vacuo. The remaining oil is mixed with 100 ml of pentane, and the precipitate which has separated out is filtered off with suction and washed twice with penteane. Drying under high vacuum results in 1.82 g of the title compound as a white solid. Rt. 2.93.

Example 63

2-Ethyl-5-(4-{3-hydroxy-5-[4-(3-methoxypropyl)-3,4-dihydro-2 H-benzor[1,4]oxazin-6-ylmethoxy]piperidin-4-yl}phenoxy)benzonitrile The title compound is obtained as a white foam in analogy to Example 1 in 3 steps (Methods A, B and C) from 0.2 g of benzyl 4-(4hydroxyphenyl)-3-[4-(3-methoxypropyl)-3,4-dihydro-2-H-benzo[1,4]oxazin-6-ylmethoxy]-5-triisopropylsilanyloxypiperdine-1-carboxylate (Example 1c), 0.1003 g of 3-cyano-4-ethylphenylboronic acid, 0.1134 g of copper(II) acetate and 0.12. ml of pyridine.

The starting materials are prepared as follows:

a) 3-Cyano-4-ethlylphenylboronic acid 9.13 ml of n-butyllithium solution (1.6M in hexane) are added dropwise to a solution of 3.00 g of 5-bromo-2-ethylbenzonitrile in 50 ml of dry tetrahydrofuran at −78° C. After stirring at this temperature for 20 minutes, 3.78 ml of triisopropyl borate are added dropwise. The reaction mixture is stirred at −78° C. for 45 minutes and then 30 ml of 1N HCl are added. After warming to room temperature, the phases are separated and the aqueous phase is extracted three more times with 100 ml of diethyl ether/tetrahydrofuran (1:1) each time. The combined organic phases are dried with sodium sulphate, filtered and concentrated to 4 ml in vacuo. The remaining oil is mixed with 100 ml of pentane and the precipitate which has separated out is filtered off with suction and washed twice with a little pentane. Drying under high vacuum results in 1.27 g of the title compound as a beige solid. Rt=3.34.

b) 5-Bromo-2-ethylbenzonitrile 9.74 ml of 2-ethylbenzonitrile are added dropwise to 100 g of Na-X zeolite (Linde 13X, STREM) with vigorous stirring. After the exothermic reaction, 5.6 ml of bromine are added dropwise at 55° C., add vigorous stirring of the mixture is continued. The temperature is kept at 45-50° C., by means of an ice bath. After the addition is complete, the ice bath is removed, and the mixture is stirred at 50° C. for 20 hours. 300 ml of methanol are added to the reaction mixture while stirring and the suspension is clarified by filtration through Hyflow. The filtrate is evaporated and the residue is partitioned between 100 ml of ethyl acetate and 50 ml of saturated sodium bicarbonate solution. The organic phase is dried with sodium sulphate, filtered and evaporated. The title compound is obtained as a beige crystalline solid from the residue by flash chromatography. Rt=4.87.

Example 73

2-Ethyl-4-(4-{3-hydroxy-5-[4-(3-methoxypropyl)-3,4-dihydro-2H-benzo[1,4]oxazin-6-ylmethoxy]piperidin-4-yl}phenoxy)benzonitrile.

The title compound is obtained as a white foam in analogy to Example 1 in 3 steps (Methods A, B and C) from 0.2 g of benzyl 4-(4-hydroxyphenyl)-3-[4-(3methoxypropyl)-3,4-dihydro-2H-benzo[1,4]oxazin-6ylmethoxy]-5-triisopropylsilanyloxypiperidine-1carboxylate (Example 1c) 0.1071 g of 4-cyano-3-ethylphenylboronic acid, 0.1134 g of copper(II) acetate and 0.12 ml of pyridine.

The starting material is prepared as follows:

a) 4-Cyano-3-ethylphenylboronic acid 3.66 ml of n-butyllithium solution (1.6M in hexane) are added dropwise to a solution of 1.14 g of 4-bromo-2-ethylbenzonitrile in 20 ml of dry tetrahydrofuran at −78° C. After stirring at this temperature for 20 minute, 1.51 ml of triisopropyl borate are added. After 45 minutes, 12 ml of 1N HCl are added to the reaction mixture, which is warmed to room temperature. The phases are separated and the aqueous phase is extracted three more times with 100 ml of diethyl ether/tetrahydrofuran (1.1) each time. The combinred organic phases are dried with sodium sulphate, filtered and concentrated to 4 ml in vacuo. The remainig oil is mixed with 40 ml of pentane, and the precipitate which has separated out is filtered off with suction and washed twice with pentane. Drying under high vacuum results in the title compound as a yellow solid. Rt=3.27.

Example 74

4-(4-{3-Hydroxy-5-[4-(3-methoxypropyl)-3,4dihydro-2H-benzo[1,4]oxazin-6-ylmethoxy]-piperdin-4-yl}phenoxy)-2,6-dimethylbenzonitrile The tile compound is obtained as a white foam in analogy to Example 1 in 3 steps (Methods A, B and C) from 0.2 g of benzyl 4-(4-hydroxyphenyl)-3-[4-(3-methoxypropy)-3,4-dihydro-2H-benzo[1,4]oxazin-6-ylmethoxy]-5triisopropylsilanyloxypiperidine-1-carboxylate (Example 1c), 0.1172 g of 4-cyano-3,5-dimethylphenylboronic acid, 0.1134 g of copper (II) acetate and 0.12 ml of pyridine.

The starting material is prepared as follows:

a) 4-Cyano-3,5-dimethylphenylboronic acid 4.55 ml of n-butyllithium solution (1.6M in hexane) are added dropwise to a solution of 1.39 g of 4-bromo-2,6-dimethylbenzonitrile in 25 ml of dry tetrahydrofuran at −78° C. After stirring at this temperature for 20 minutes, 1.88 ml of triisopropyl borate are added. After 45 minutes, 15 ml of 1N aqueous HCl are added to the reaction mixture, which is warmed to room temperature. The phases are separated and the aqueous phase is extracted three more times with 100 ml of diethyl ether/tetrahydrofuran (1:1) each time. The combined organic phases are dried with sodium sulphate, filtered and concentrated to 4 ml in vacuo. The remaining oil is mixed with 50 ml of pentane, and the precipitate which has separated out is filtered off with suction and washed twice with pentane. Drying under high vacuum results in the title compound as a beige solid. Rt=3.20.

Example 8

4-[4-(3-Chlorophenoxy)phenyl]-5-[4-(3-methoxypropyl)-3,4-dihydro-2H-benzo1,4]oxazin-6 -yl-methoxylpiperidin-3-ol The title compound is obtained as a colourless film in analogy to Method E from 93.9 mg of benzyl 4-[4-(3-clorophenoxy)phenyl]-3-hydroxy-5-[4-(3methoxypropyl)-3,4-dihydro-2H-benzo[1,4]oxazin-6-ylmethoxy]piperidine-1-carboxylate.

The starting materials are prepared as follow:

a) Benzyl 4-[4-(3chlorophenoxy)phenyl]-3-hydroxy-5-[4-(3-methoxypropyl)-3,4-dihydro-2H-benzo[1,4]oxazin-6-ylmethoxy]piperidine-1-carboxylate The title compound is obtained as a colourless oil in analogy to Method B from 131.7 mg of benzyl 4-[4-(3chlorophenoxy)phenyl]-3-[4-(3methoxypropyl)-3,4-dihydro-2H-benzo[1,4]oxazin-6 -ylmethoxy]-5-triisopropylsilanyloxypiperidine-1-carboxylate. Rf (ETOAc/heptane 1:1=0.17; Rt=5.55.

b) 4-[4-(3-chlorophenoxy)phenyl]-3-[4-(3-methoxypropyl)-3,-4-dihydro-2H-benzo-[1,4]oxazin-6-ylmethoxy]-5trisopropylsilanyloxypiperidine-1-carboxylate The title compound is obtained as a yellow oil in analogy to Method C from 0.2 g of benzy 4-(4-hydroxyphenyl)-3 -[4-(3-methoxypropyl)-3,4 -dihydro-2H-benzo[1,4]oxazin-6-ylmethoxy]-5-triisopropylsilanyloxypiperidine-1-carboxylate (Example 1c), 0.2241 g of 3-chlorophenyl-boronic acid, 0.113 g of copper(II) acetate and 0.19 ml of triethylamine. Rf (EtOAc/heptane 1:2) 0.26.

The following compounds are prepared in an analogous manner to the process described in Example 8:

20   4-[4-(4-Chlorophenoxy)phenyl]-5-[4-(3-methoxvpropyl)-3,4   -dihydro-2H-benzo[1,4]oxazin-6-methoxy] piperidin3ol
31   5-[4-(3-Methoxypropyl)-3,4-dihydro-2H-benzo[1,4oxazin-6-ylmethoxy]-4-4-(3 -methylsulphanylphenoxy)phenyl]piperidin-3ol
36   5-[4-(3-Methoxypropyl)-3,4-dihydro-2H-benzo[1,4]oxazin-6-ylmethoxy]-4-[4 -(4-methyl-sulphanylphenoxy)phenyl]piperidin-3-ol
37   4-[4-(3-Chloro-4-methylphenoxy)phenyl]-5-[4-(3-methoxypropyl)-3,4-dihydro-2H-benzor[1,4]oxazin-6 -methoxy]piperidin-3-ol
41   4-[4-(3,4-Dichlorophenoxy)pheny]-5-[4-(3-methoxypropyl)-3,4-dihydro-2H-benzo-[1,4]oxazin-6 -ylmethoxy]piperidin-3-ol
42   4-[4-(4-Choro-3-methylphenoxy)phenyl]-5-[4-(3-methoxypropyl)-3,4-dihydro-2H-benzo[1,4   ]oxazin-6yl-methoxy]piperidin-3ol
43   4-[4-(3Chloro-4isopropoxyphenoxy)phenyl]-5-[4-(3-methoxypropyl)-3,4-dihydro-2H-benzo[1,4  ]oxazin-6yl-methoxy]piperidin-3-ol
44   4-[4-(3-Chloro-4-methoxvphenoxy)phenyl]-5-[4-(3-methoxypropyl)-3,4-dihydro-2H-benzo[1,4 ]oxazin-6-yl-methoxy]piperidin-3-ol
45   4-[4-(3-Chloro-4ethoxyphenoxy)phenyl]-5-[4-(3-methoxypropyl)-3,4-dihydro-2H-benzo[1,4   ]oxazin-6yl-methoxy]piperdin-3-ol Example 56

4-[4-(Benzo[b]thiophen-5-yloxy)phenyl]-5-[4-(3methoxypropyl)-3,4-dihydro-2H-benzo[1,4 ]oxazin-6-ylmethoxy]piperdin-3ol The title compound is obtained as a colourless foam in analogy to Example 8 in 3 steps (Methods C, B and E) from 0.2 g of benzyl 4-(4-hydroxyphenyl)-3-[4-(3-methoxypropyl)-3,4-dihydro-2H-benzo[1,4 ]oxazin-6-ylmethoxy]-5-triisopropylsilanyloxypiperidine-1-carboxylate (Example 1c), 0.2502 g of benzo[b]thiophene-5-boronic acid. 0.1134g of copper(II) acetate and 0.19 ml of triethylamine.

The starting material is prepared as follows:

a) Benzo[b]l thiophene-5-boronic acid

A solution of 0.6 g of 2-(l-benzothiophen-5-yl) 4,4,5,5-tetramethyl-1,3,2-dioxaborolane in 2.5 m of dichloromethane is added dropwise to a solution of boron trichloride in dichloromethane (1M, 14.3 ml) at −78° C. After 15 minutes, the reaction mixture is warmed to room temperature, and 8 ml of methanol are added dropwise. It is then evaporated to dryness and dried under high vacuum overnight. 0.350 g of the title compound is obtained as a grey powder Rt=3.33.

Example 60

5-[4-(3-Methoxypropyl)-3,4-dihydro-2H-benzo[1.4] oxazin-6-ylmethoxy]-4 -[4-(pyridin-2 -yloxy)-phenyl]piperidin-3-ol The title compound is obtained as a colourless oil in analogy to Method A from 68.8 mg of benzyl 3-hydroxy-5-[4-(3-methoxypropyl)-3,4-dihydro-2H-benzo[1,4]oxazin-6 ylmethoxy]-4-[4-(pyridin-2 -yloxy)phenyl]piperidine-1-carboxylate.

The starting materials are prepared as follows:

a) Benzyl 3-hydroxy-5-[4-(3-methoxypropyl)-3,4-dihydro-2H-benzo[1,4 ]oxazin-6-ylmethoxy]-4 -[4-pyridin-2-yloxy)phenyl]piperdine-1-carboxylate The title compound is obtained as a colourless film in analogy to Method B from 180 mg of benzyl 3-[4-(3-methoxypropyl)-3,4-dihydro-2H-benzo[1,4]oxazin-6ylmethoxy]-4-[4 -(pyridin-2-yloxy)phenyl]-5triisopropylsilanyloxypiperidine-1carboxylate. Rf (EtOAc/heptane 3:1)=0, 12; Rt=4.76.

b) Benzyl 3-[4-(3-methoxypropyl)3,4-dihydro-2H-benzo[1,4]oxazin6-ylmethoxy]-4-[4 -(pyridin-2-yloxy)phenyl]-5-triisopropysilanyloxypiperidine-1-carboxylate The title compound is obtained as a yellowish oil in analogy to Method D from 0.2 g of benzyl 4-(4-hydroxyphenyl)-3-[4-(3-methoxypropyl)-3,4dihydro-2H-benzo[1,4]oxazin-6 -ylmethoxy]-5-triisopropylsilanyloxypiperdine-1carboxylate (Example 1c), 0.133 g of 2-bromopyridine and 0.157 g of potassium carbonate. Rf-(EtOAc/heptane 2.3)=0.20

The -following compounds are prepared in an analogous manner to the process described in Example 60:

64 5-[4-(3-Methoxypropyl)-3,4-dihydro-2H-benzo[1,4]oxazin-6-ylmethoxy]-4-[4-(5-methyl-pyridin-2 -yloxy)phenyl]piperidin-3-ol 65 4-[4-(4,6-Dimethylprimidin-2-yloxy)phenyl]-5[4-(3-methoxypropyl)-3,4-dihydro-2 H-benzo[1,4]oxazin-6-ylmethoxy]piperdin-3-ol 67 5-[4-(3-Methoxypropyl)-3,4-dihydro-2H-benzo[1,4]oxazin-6-ylmethoxy]-4-[4-(4-methoxypyridin-2 -yloxy)phenyl]piperidin-3-ol 68 4-[4-(5-Ethylpyrimidin-2-yloxy)phenyl]-5[4-(3-methoxypropyl)-3,4-dihydro-2 H-benzo[1,4]oxazin-6-ylmethoxy]piperdin-3-ol 69 5-[4-(3-Methoxypropyl)-3,4-dihydro-2H-benzo[1,4]oxazin-6-ylmethoxy]-4-[4-(6-methyl-pyridin-2 -yloxy)phenyl]piperidin-3-ol 70 5-[4-(3-Methoxypropyl)-3,4-dihydro-2H-benzo[1,4]oxazin-6-ylmethoxy]-4-[4 -(4-methyl-pyridin-2-yloxy)phenyl]piperidin-3-ol 71 5-[4-(3-Methoxypropyl)-3,4-dihydro-2H-benzo[1,4]oxazin-6-ylmethoxy]-4-[4 -(5-methyl-pyridin-2-yloxy)phenyl]piperidin-3-ol 72 5-[4-(3-Methoxypropyl)-3,4-dihydro-2H-benzo[1,4]oxazin-6-ylmethoxy]-4-[4-(quinolin-2 -yloxy)phenyl]piperidin-3-ol 75 4-[4-(2,6-Dimethylprimidin-4-yloxy)phenyl]-5[4-(3-methoxypropyl)-3,4-dihydro-2H-benzo[1,4]oxazin-6-ylmethoxy]piperdin-3-ol 76 4-[4-(4,6-Dimethylprimidin-2-yloxy)phenyl]-5[4-(3-methoxypropyl)-3,4-dihydro-2H-benzo[1,4]oxazin-6-ylmethoxy]piperdin-3-ol 77 5-[4-(3-Methoxypropyl)-3,4-dihydro-2H-benzo[1,4]oxazin-6-ylmethoxy]-4-[4 -(quinoxalin-2-yloxy)phenyl]piperidin-3-ol 78 4-[4-(3,6-Dimethylprimidin-2-yloxy)phenyl]-5[4-(3-methoxypropyl)-3,4-dihydro-2H-benzo[1,4]oxazin-6-ylmethoxy]piperdin-3-ol 81 4-[4-(Isoquinolin-3-yloxy)phenyl]-5[4-(3-methoxypropyl)-3,4-dihydro-2H-benzo[1,4 ]oxazin-6-ylmethoxy]piperdin-3-ol 82 6-(4,3{-Hydroxy-5[4-(3-methoxypropyl)-3,4-dihydro-2H-benzo[1,4]oxazin-6 -ylmethoxy]piperdin-4-yl}phenoxy)piridine-2carbonitrile Example 66

4-[4-(5-Bromopyrimidin-2-yloxy)phenyl]-5-[4-(3methoxypropyl)-3,4-dihydro-2H-benzo[1,4]oxazin-6-ylmethoxy]piperdin-3ol A solution of 139.8 mg of benzyl 4-[4-(5-bromopyrimidin-2-yloxy)phenyl]-3-hydroxy-5-[4 -(3-methoxypropyl)-3,4-dihydro-2H-benzo[1,4]oxazin-6-ylmethoxy]piperidine-1-carboxylate in 0.5 ml of dichloromethane is added to a mixture of 0.232 ml of boron trifluoride etherate and 0.4 ml of ethanethiol. The reaction mixture is stirred at room temperature under argon for 20 hours. The solvent is then evaporated off, and 2 ml of water are added to the residue. The aqueous phase is extracted three times with 5 ml of ethyl acetate each time. The combined organic phases are dried with sodium sulphate, filtered and evaporated. The title compound is obtained as a beige wax from the residue by flash chromatography ($SiO_2$ 60F).

The starting materials are prepared as follows:

a) 4-[4-(5-bromopyrimidin-2-yloxy)phenyl]-3-hydroxy-5-[4-(3methoxypropyl)-3,4-dihydro-2 H-benzo[1,4]oxazin-6-ylmethoxy]piperdin-1-carboxylate The title compound is obtained as a yellow oil in analogy to Method B from -399.7 mg of benzyl 4-[4-(5-bromopyrimidin-2-yloxyphenyl]-3-[4-(3-methoxypropyl)-3,4-dihydro-2 H-benzo[1,4]oxazin-6-ylmethoxy]-5-triisopropylsilanyloxypiperidine-1-carboxylate. Rf (EtOAc/heptane 2:1)=0.24; Rt=4.92.

b) 4-[4-(5-bromopyrimidin-2-yloxy)phenyl]-3-[4-(3methoxypropyl)-3,4-dihydro-2 H-benzo[1,4]oxazin-6-ylmethoxy]-5-triisopropylsilanyloxypiperidine-1-carboxylate The title compound is obtained as a yellow oil in analogy#to Method D from 0.2 g of benzyl 4-(4-hydroxyphenyl)3 -[4-(3-methoxypropyl)-3,4-dihydro-2H-benzo[1,4] orazin-6-ylmethoxy]-5-triisopropylsilanyloxypiperidine-1 -carboxylate (Example 1c), 0.3292 g of 5-bromo-2-chloropyrimidine and 0.2427 g of potassium carbonate. Rf (EtOAc/heptane 1:2)=0.27.

Example 80

5-[4-(3-Methoxypropyl)-3,4dihydro-2H-benzo1,4oxazin-6-ylmethoxy]-4[4-(1 -oxypyidin-2-yloxy)phenyl]piperidin-3-ol The compound is obtained as a colourless film in analogy to Method A from 27.1 mg of benzyl 3-hydroxy-5-[4-(3-methoxypropyl)-3,4-dihydro-2H-benzo[1,4]oxazin-6 -yl methoxy]-4-[4-(1-oxypyridin-2-yloxy)phenyl]piperidine1-carboxylate.

The starting materials are prepared as follows:

a) Benzyl 3-hydroxy-5-[4-(3-methoxypropyl)-3,4-dihydro-2H-benzo[1,4]oxazin-6 -ylmethoxy]-4-[4-(1-oxypyridin-2-yloxy)phenyl]piperidine-1carboxylate The title compound is obtained as a white foam in analogy to Method B from 38.6 mg of benzyl 3-[4-(3-methoxypropyl)-3,4-dihydro-2H-benzo[1,4]oxazin-6-ylmethoxy]-4-[4

-(1-oxypyridin-2-yloxy)phenyl]-5-triisopropylsilanyloxypiperidine-1-carboxylate. Rf (dichloromethane/methanol/25% conc. ammonia 200:20:1)=0.27; Rt=3.93.

b) Benzyl 3-[4-(3-methoxypropyl)-3,4-dihydro-2H-benzo[1,4]oxazin-6-ylmethoxy]-4-[4-(1-oxypyridin-2-yloxy)phenyl]-5-triisopropylsilanyloxypiperidine-1-carboxylate 0.6 ml of a boron-tetrahydrofuran complex solution (1M in tetrahydrofuran) is added dropwise to a solution of 134.8 mg of benzyl 3-[4-(3-methoxypropyl)-3-oxo-3,4-dihydro-2H-benzo[1,4]oxazin-6-ylmethoxy]4-[4-(1-oxypyridin-2-yloxy)phenyl]-5-triisopropylsilanyloxy-piperidine-1-carboxylate in 2 ml of tetrahydrofuran at 0° C. After 5 hours, 2 ml of methanol are slowly added at 0° C., and the resulting mixture is evaporated. The title compound is obtained as a white film from the residue by flash chromatography (SiO$_2$ 60F). Rf (dichloromethane/methanol/25% conc. ammonia 200:10:1)=0.07.

c) Benzyl 3-[4-(3-methoxypropyl)-3-oxo-3,4-dihydro-2H-benzo[1,4]oxazin-6-ylmethoxy]-4-[4-(1-oxypyridin-2-yloxy)phenyl]-5-triisopropylsilanyloxypiperidine-1-carboxylate 144 mg of chloroperbenzoic acid are added to a solution of 162.9 mg of benzyl 3-[4-(3-methoxypropyl)-3-oxo-3,4-dihydro-2-H-benzo[1,4]oxazin-6-ylmethoxy]-4-[4pyridin-2-yloxy)-phenyl]-5-triisopropylsilanyoxypiperidine-1-carboxylate in 5 ml of dichloromethane, and the mixture is stirred at room temperature for 90 minutes. The reaction mixture is evaporated, and the title compound is obtained as a white solid from the residue by flash chromatography (SiO$_2$ 60F). Rf (dichloromethane/methanol/25% conc. ammonia 200:10:1)=0.22.

d) Benzyl 3-[4-(3-methoxypropyl)-3oxo-3,4-dihydro-2H-benzo[1,4]oxazin-6-ylmethoxy]-4-[4-(pyridin-2-yloxy)phenyl]-5-triisopropylsilanyloxypiperidine-1-carboxylate The title compound is obtained as a yellow oil in analogy of Method D from 0.2 g of benzl 4-(4-hydroxyphenyl)-3-[4-(3-methoxypropyl)-3-oxo-3,4dihydro-2H-benzo[1,4]oxazin-6-ylmethoxy]-5-triisopropylsilanyoxypiperidine-1-carboxylate (Example 1d), 0.19 g of 2-chloropyridine and 0.231 g of potassium carbonate. Rf (EtOAc/heptane2:3)=0.16.

Example 83

5-[4-(3-Methoxypropyl)-3,4-dihydro-2H-benzo[1,4]oxazin-6-ylmethoxy]-4-[4-(1-oxypyridin-3-yloxy)phenyl]piperidin-3-ol The title compound is obtained as a colourless film in analogy to Method A from 25.4 mg of benzyl 3-hydroxy-5-[4-(3methoxypropyl)-3,4-dihydro-2H-benzo[1,4]oxazin-6-ylmethoxy]-4-[4-(1-oxypyridin-3yloxy)phenyl]piperidine-1- carboxylate.

The starting materials are prepared as follows:

a) Benzyl 3-hydroxy-5-[4-(3-methoxypropyl)-3,4-dihydro-2H-benzo[1,4]oxazin-6-ylmethoxy]-4-[4-(1-oxypyridin-3-yloxy)phenyl]piperidine-1-carboxylate benzyl 3-[4-(3-methoxypropyl-3,4-dihydro-2H-benzo[1,4]orazin-6-ylmethoxy]-4-[4-(1-oxypyridin-3-yloxy)phenyl]-5-triisopropylsilanyloxypiperidine-1-carboxylate.
The title comnpound is obtained as a white foam in analogy to Method B from 48.3 mg of Rf (dichloromethane/methanol/25% conc. ammonia 200:20:1)=0.29; Rt=4.05.

b) Benzyl 3-[4-(3-methoxypropyl)-3,4-dihydro-2H-benzo[1,4]oxazin-6-ylmethoxy]-4-[4-(1-oxypyridin-3-yloxy)phenyl]-5-triisopropylsilanyloxypiperidine-1-carboxylate 0.95 ml of a borane-tetrahydrofuran complex solution (1M in tetrahydrofuran) is added dropwise to a solution of 194.5 mg of benzyl 3-[4-(3-methoxypropyl)-3-oxo-3,4-dihydro-2H-benzo[1,4]oxazin-6-ylmethoxy]-4-[4-(1-oxypyridin-3-yloxy)phenyl]-5-triisopropylsilanyloxy-piperidine-1-carboxylate in 2 ml of tetrahydrofuran at 0° C. After 30 minutes, 0.9 ml of methanol is slowly added at 0° C., and the resulting mixture is concentrated. The title compound is obtained as a white foam from the residue by flash chromatography (SiO$_2$ 60F). Rf (dichloromethane/methanol/25% conc. ammonia 200:10:1)=0.14.

c) Benzyl 3-[4-(3-methoxypropyl)-3-oxo-3,4-dihydro-2H-benzo[1,4]oxazin-6-ylmethoxy]-4-[4-(1-oxypyridin-3-yloxy)phenyl]-5-triisopropylsilanyloxypiperidine-1-carboxylate 241.1 mg of m-chloroperbenzoic acid are added to a solution of 163.8 mg of benzyl 3-[4-(3-methoxypropyl)-3-oxo-3,4-dihydro-2H-benzo[1,4]oxazin-6-ylmethoxy]-4-[4-pyridin-3yloxy)-phenyl]-5-triisopropylsilanyloxypiperidine-1carboxylate in 3.3 ml of dichloromethane and stirred at room temperature for 15 hours. The reaction mixture is concentrated, and the title compound is obtained as a white foam from the residue by flash chromatography (SiO$_2$ 60F). Rf (dichloromethane/methanol/25% conc. ammonia 200:10:1)=0.17.

d) Benzyl 3-[4-(3-methoxypropyl)-3-oxo-3,4-dihydro-2H-benzo[1,4]oxazin-6-ylmethoxy]-4-[4-(pyridin-3-yloxy)phenyl]-5-triisopropylsilanyloxypiperidine-1-carboxylate The title compound is obtained as a yellow oil in analogy to Method C from 0.81 g of benzyl 4-(4-hydroxyphenyl)-3-[4-(3-methoxypropyl)-3-oxo-3,4-dihydro-2H-benzo[1,4]oxazin-6-ylmethoxy]-5-triisopropylsilanyloxypiperidine-1-carboxylate (Example 1d), 0.5601 g of 3-pyridine boronic acid, 0.4506 g of copper(II) acetate and 0.77 ml of triethylamine. Rf (EtOAc/heptane 1:1)=0.10.

Example 84

5-[4-(3-Methoxypropyl)-3,4-dihydro-2H-benzo[1,4]oxazin-6-ylmethoxy]-4-[4-(1-oxypyridin-4-yloxy)phenyl]piperidin-3-ol The title compound is obtained as a colourless film in analogy to Method A from 150 mg of benzyl 3-hydroxy-5-

[4-(3-methoxypropyl)-3,4-dihydro-2H-benzo[1,4]oxazin-6ylmethoxy]-4-[4-1 -oxypyridin-4-yloxy)phenyl]piperidine-1-carboxylate.

The starting materials are prepared as follows:

a) Benzyl 3-hydroxy-5[4-(3-methoxypropyl)-3,4-dihydro-2H-benzo[1,4]oxazin-6-ylmethoxy]-4[4-(1oxypyridin-4-yloxy)phenyl]piperidine-1-carboxylate The title compound is obtained as a brownish resin in analogy to Method B from 171 mg of benzyl 3-[4-(3-methoxypropyl)-3,4-dihydro-2H-benzo[1,4]oxazin-6-ylmethoxy]-4-[4-(1-oxy-pyridin-4-yloxy)phenyl]-5-triisopropylsilanyloxypiperidine-1-carboxylate. Rf (CH$_2$Cl$_2$/MeOH 95:5)=0.28, Rt=4.06.

b) Benzyl 3-[4-(3-methoxypropyl)-3,4-dihydro-2H-benzo[1,4]oxazin-6-ylmethoxy]-4-[4-(1 -oxypyridin-4-yloxy)phenyl]-5- triisopropylsilanyloxypiperidine-1-carboxylate The title compound is obtained as a brown resin in analogy to Method D from 400 mg of benzyl 4-(4hydroxyphenyl)-3[4-(3methoxypropyl)-3,4-dihydro-2H-benzo[1,4]oxazin-6-ylmethoxy]-5 -triisopropylsilanyloxypiperidine-1-carboxylate (Example 1c), 91.9 mg of 4-chloropyridine N-oxide and 156.8 mg of potassium carbonate. Rf (CH$_2$Cl$_2$/MeOH 95:5)= 0.38.

Example 85

(2-{5-[4-(3-Methoxypropyl)-3,4-dihydro-2H-benzo[1,4]oxazin-6-ylmethoxy]-4 -[4-(4-methyl-3,4-dihydro-2H-benzo[1,4]oxazin-7-yloxy)phenyl]piperidin-3yloxy}ethyl)methylamine 246 mg of sodium/mercury amalgram are added to a solution of 110 mg of N-{2-[5-[4-(3-methoxypropyl)-3,4 -dihydro-2H-benzo[1,4]oxazin-6ylmethoxy]-4-[4-(4-methyl-3,4-dihydro-2H-benzo[1,4 ]oxazin-7-yloxy)phenyl]-1-(toluene-4-sulphonyl)piperidin-3 -yloxy]ethyl}-4N-dimethylbenzene sulphonamide and 80 mg of anhydrous sodium dihydrogenphosphate in 4 ml of methanol under argon. After the reaction is complete, the reaction mixture is diluted with water and extracted with ethyl acetate (3×)—the combined organic phases are washed with brine, dried with sodium sulphate and evaporated. The title compound is obtained as a white resin from the residue by flash chromatography (SiO$_2$ 60F).

The starting materials are prepared as follows:

a) N-{2-[5-[4-(3-Methoxypropyl)-3,4-dihydro-2H-benzo[1,4]oxazin-6-ylmethoxy ]-4-[4-(4-methyl-3,4-dihydro-2H-benzo[1,4]oxazin-7-yloxy)phenyl]-1-(toluene-4-sulphonyl)-piperidin-3-yloxy ]ethyl}-4,N-dimethylbenzene sulphonamide 95 mg of sodium hydride dispersion (60%) are added to a solution of 145 mg of 5-[4-(3-methoxypropyl)3,4 -dihydro-2H-benzo[1,4]oxazin-6-ylmethoxy]-4-[4-(4-methyl-3,4-dihydro-2 H-benzo[1,4]oxazin-7-yloxy)phenyl]-1-(toluene-4-sulphonyl)piperidin-3-ol and 740 mg of 2-[methyl(toluene-4 -sulphonyl)amino]ethyl toluene-4-sulphonate in 5 ml of tetrahydrofuran while stirring at room temperature. The reaction mixture is stirred at 45° C. for 72 hours. The mixture is poured into 1M aqueous sodium bicarbonate solution (5 ml) and extracted with tert-butyl methyl ether (2×50 ml). The organic phases are washed successively with water (2×10 ml) and brine (1×10 ml), dried with sodium sulphate and evaporated. The title compound is obtained from the residue by flash chromatography (SiO$_2$ 60F). Rf=0.08 (EtOAc/heptane 1:1); Rt=5.83.

b) 5-[4-(3-Methoxypropyl)-3,4-dihydro-2H-benzo[1,4]oxazin-6-ylmethoxy]-4 -[4-(4methyl-3,4-dihydro-2H-benzo[1,4]oxazin-7-yloxy)phenyl]-1-(toluene-4-sulphonyl)piperidin-3ol A mixture of 105.7 mg of 5-[4-(3-methoxypropyl)-3,4-dihydro-2H-benzo[1,4]oxazin-6-ylmethoxy]-4-[4 -(4-methyl-3,4-dihydro-2H-benzo[1,4]oxazon-7-yloxy)phenyl]piperidin-3-ol (Example 58) in 3.3 ml of ethyl acetate and 3.3 ml of 2N aqueous sodium carbonate solution is mixed with 37.7 mg of p-toluenesulphonyl chloride and stirred for 15 hours. The phases are separated, and the organic phase is extracted twice more with 10 ml of ethyl acestate each time. The combined organic phases are washed once with brine (10 ml), dried with sodium sulphate and concentrated. The title compound remains as a white foam. Rt=5.05.

c) 2-[Methyl(toluene-4-sulphonyl)amino]ethyl toluene-4sulphonate 10.55 g of p-toluenesulphonyl chloride are added to a solution of 2.13 ml of 2-(methylamino)-ethanol and 8 ml of triethylamine in 25 ml of dichloromethane while cooling in ice, and the mixture is stirred at room temperature for 20 hours. The reaction mixture is diluted with 100 ml of tert-butyl methyl ether and washed with 0.1M HCl (50 ml), water (50 ml) and brine (50 ml). The organic phase is dried with sodium sulphate and evaporated, whereupon the title compound crystallizes as white solid. Rt=4.67.

What is claimed is:
1. A compound of the formula

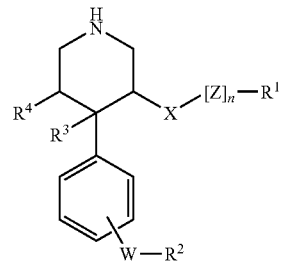

(I)

in which
(F) R$^1$ is 3,4-dihydro-2H-benzo[1,4]oxazinyl substituted by 1-4 acetamidinyl-C$_{1-6}$alkyl, acyl-C$_{1-6}$alkoxy-C$_{1-6}$alkyl, (N-acyl)-C$_{1-6}$alkoxy-C$_{1-6}$alkylamino, C$_{1-6}$alkoxy, C$_{1-6}$alkoxy-C$_{1-6}$alkoxy, C$_{1-6}$alkoxy-C$_{1-6}$alkoxy-C$_{1-6}$alkyl, C$_{1-6}$alkoxy-C$_{1-6}$alkyl, (N—C$_{1-6}$alkoxy)-C$_{1-6}$alkylaminocarbonyl-C$_{1-6}$alkoxy, (N—C$_{1-6}$alkoxy)-C$_{1-6}$alkylaminocarbonyl-C$_{1-6}$alkyl, C$_{1-6}$alkoxy-C$_{1-6}$alkylcarbamoyl, C$_{1-6}$alkoxy-C$_{1-6}$alkylcarbonyl, C$_{1-6}$alkoxy-C$_{1-6}$alkylcarbonylamino, 1-C$_{1-6}$alkoxy-C$_{1-6}$alkylimidazol-2-yl, 2-C$_{1-6}$alkoxy-C$_{1-6}$alkyl-4-oxoimidazol-1-yl, 1-C$_{1-6}$alkoxy-C$_{1-6}$ alkyltetrazol-5-yl, 5-C$_{1-6}$alkoxy-C$_{1-6}$alkyltetrazol-1-yl, 6-alkoxyaminocarbonyl-C$_{1-6}$alkoxy, C$_{1-6}$alkoxyaminocarbonyl-C$_{1-6}$alkyl, C$_{1-6}$alkoxycarbonyl, C$_{1-6}$alkoxycarbonyl-C$_{1-6}$alkoxy, C$_{1-6}$alkoxycarbonyl-C$_{1-6}$alkyl, $C_{1-6}$alkoxycarbonylamino-$C_{1-6}$alkoxy, $C_{1-6}$alkoxycarbonylamino-$C_{1-6}$alkyl, $C_{1-6}$alkyl, (N—$C_{1-6}$alkyl)-$C_{1-6}$alkoxy-$C_{1-6}$alkylcarbamoyl, (N—$C_{1-6}$alkyl)-$C_{1-6}$alkoxy-$C_{1-6}$alkylcarbonylamino, (N—$C_{1-6}$alkyl)-$C_{1-6}$alkoxy-carbonylamino, (N—$C_{1-6}$-alkyl)-$C_{0-6}$ alkylcarbonylamino-$C_{1-6}$alkoxy, (N—$C_{1-6}$alkyl)-$C_{0-6}$alkylcarbonylamino-$C_{1-6}$alkyl, (N—$C_{1-6}$alkyl)-$C_{1-6}$alkylsulphonylamino-$C_{1-6}$alkoxy, (N—$C_{1-6}$alkyl)-$C_{1-6}$alkylsulphonylamino-$C_{1-6}$alkyl, $C_{1-6}$alkylamidinyl, $C_{1-6}$alkylaminocarbonyl-$C_{1-6}$alkoxy, di-$C_{1-6}$alkylaminocarbonyl-$C_{1-6}$alkoxy, $C_{1-6}$alkylaminocarbonyl-$C_{1-6}$alkoxy-$C_{1-6}$alkyl, $C_{1-6}$alkylaminocarbonyl-$C_{1-6}$alkyl, $C_{1-6}$alkylaminocarbonylamino-$C_{1-6}$alkoxy, $C_{1-6}$alkylaminocarbonylamino-$C_{1-6}$alkyl, di-$C_{1-6}$alkylaminocarbonyl-$C_{1-6}$alkyl, $C_{1-6}$alkylamino-$C_{2-6}$alkoxy, di-$C_{1-6}$alkylamino-$C_{2-6}$alkoxy, $C_{1-6}$alkylamino-$C_{1-6}$alkyl, di-$C_{1-6}$alkylamino-$C_{1-6}$alkyl, $C_{1-6}$alkylcarbamoyl, di-$C_{1-6}$alkylcarbamoyl, $C_{0-6}$alkylcarbonylamino-$C_{1-6}$alkoxy, $C_{0-6}$alkylcarbonylamino, $C_{0-6}$alkylcarbonylamino-$C_{1-6}$alkyl, $C_{1-6}$alkylcarbonyloxy-$C_{1-6}$alkoxy, $C_{1-6}$alkylcarbonyloxy-$C_{1-6}$alkyl, $C_{1-6}$alkylsulphonyl, $C_{1-6}$alkylsulphonyl-$C_{1-6}$alkoxy, $C_{1-6}$alkylsulphonyl-$C_{1-6}$ alkyl, $C_{1-6}$alkylsulphonylamino-$C_{1-6}$alkoxy, $C_{1-6}$alkylsulphonylamino-$C_{1-6}$alkyl, carbamoyl, carbamoyl-$C_{1-6}$alkoxy, carbamoyl-$C_{1-6}$alkyl, carboxy-$C_{1-6}$ alkoxy, carboxy-$C_{1-6}$alkoxy-$C_{1-6}$alkyl, carboxy-$C_{1-6}$ alkyl, cyano, cyano-$C_{1-6}$alkoxy, cyano-$C_{1-6}$alkyl, $C_{3-6}$cycloalkyl-carbonylamino-$C_{1-6}$alkoxy, $C_{3-6}$cycloalkylcarbonylamino-$C_{1-6}$alkyl, cyclopropyl-$C_{1-6}$ alkyl, O,N-dimethylhydroxylamino-$C_{1-6}$alkyl, halogen, hydroxy-$C_{2-6}$alkoxy-$C_{1-6}$alkoxy, hydroxy-$C_{2-6}$ alkoxy-$C_{1-6}$alkyl, hydroxy-$C_{1-6}$alkyl, (N-hydroxy)-$C_{1-6}$ alkylaminocarbonyl-$C_{1-6}$alkoxy, (N-hydroxy)-$C_{1-6}$ alkylaminocarbonyl-$C_{1-6}$alkyl, (N-hydroxy)-aminocarbonyl-$C_{1-6}$alkoxy, (N-hydroxy) aminocarbonyl-$C_{1-6}$alkyl, 2-oxooxazolidinyl-$C_{1-6}$ alkoxy, 2-oxooxazolidinyl-$C_{1-6}$alkyl, O-methyloximyl-$C_{1-6}$alkyl or trifluoromethyl or by 3-acetamidomethylpyrrolidinyl, 3-$C_{1-6}$alkoxy-$C_{1-6}$alkylpyrrolidinyl, 3,4-dihydroxypyrrolidinyl, 2,6-dimethylmorpholinyl, 3,5-dimethylmorpholinyl, dioxanyl, dioxolanyl, 4,4-dioxothiomorpholinyl, dithianyl, dithiolanyl, 2-hydroxymethylpyrrolidinyl, 4-hydroxypiperidinyl, 3-hydroxypyrrolidinyl, imidazolyl-alkoxy, imidazolylalkyl, 2-methylimidazolylalkoxy, 2-methylimidazolylalkyl, 3-methyl-[1,2,4]-oxadiazol-5-ylalkoxy, 5-methyl[1,2,4]-oxadiazol-3-ylalkoxy, 3-methyl-[1,2,4]-oxadiazol-5-ylalkyl, 5-methyl-[1,2,4]-oxadiazol-3-ylalkyl, 4-methylpiperazinyl, 5-methyltetrazol-1-ylalkoxy, 5-methyltetrazol-1-ylalkyl, morpholinyl, [1,2,4]-oxadiazol-5-ylalkoxy, [1,2,4]-oxadiazol-5-ylalkyl, oxazol-4-ylalkoxy, oxazol-4-ylalkyl, 2-oxo-[1,3]oxazinyl, 2-oxooxazolidinyl, 2-oxoimidazolidinyl, 2-oxopyrrolidinyl, 4-oxopiperidinyl, 2-oxopyrrolidinylalkoxy, 2-oxopyrrolidinylalkyl, 2-oxotetrahydro-pyrimidinyl, 4-oxothiomorpholinyl, piperazinyl, piperidinyl, pyrrolidinyl, pyrrolyl, [1,2,4]-triazol-1-ylalkoxy, [1,2,4]-triazol-4-ylalkoxy, [1,2,4]-triazol-4-ylalkyl, tetrazol-1-ylalkoxy, tetrazol-2-ylalkoxy, tetrazol-5-ylalkoxy, tetrazol-1-ylalkyl, tetrazol-2-ylalkyl, tetrazol-5-ylalkyl, thiazol-4-ylalkoxy, thiazol-4-ylalkyl, or thiomorpholinyl;

$R^2$ is phenyl or a heterocyclyl which is linked via a C atom, each of which radicals may be substituted by 1-4 $C_{1-6}$alkanoyl, $C_{1-6}$alkoxy, $C_{1-6}$alkoxy-$C_{1-6}$alkoxy, $C_{1-6}$alkoxy-$C_{1-6}$alkyl, $C_{1-6}$alkoxycarbonylamino, $C_{1-6}$alkyl, $C_{0-6}$alkylcarbonylamino, $C_{1-6}$alkylenedioxy, $C_{1-6}$alkylsulphanyl, $C_{1-6}$alkylsulphonyl, optionally N-mono- or N,N-di-$C_{1-6}$-alkylated amino, optionally N-mono- or N,N-di-$C_{1-6}$-alkylated carbamoyl, optionally esterified carboxy, cyano, cyano-$C_{1-6}$alkyl, $C_{3-8}$cycloalkoxy, $C_{3-8}$cycloalkyl, halogen, hydroxy-$C_{1-6}$alkyl, nitro, oxide, oxo, trifluoromethyl, trifluoromethoxy or optionally N—$C_{1-6}$-alkylated piperazinyl-$C_{1-6}$alkyl;

$R^3$ is hydrogen;

$R^4$ is optionally N-mono- or N,N-di-$C_{1-6}$-alkylated amino-$C_{1-6}$alkoxy or hydroxy;

$R^5$ is acyl, $C_{2-8}$alkenyl, $C_{1-6}$alkyl, aryl-$C_{1-6}$alkyl or hydrogen;

$R^6$ is acyl, $C_{1-6}$alkoxy-$C_{1-6}$alkyl, $C_{1-6}$alkyl or aryl-$C_{1-6}$ alkyl or hydrogen;

$R^7$ is $C_{1-6}$ alkoxycarbonyl-$C_{1-6}$alkyl, $C_{1-6}$alkyl, carboxy-$C_{1-6}$alkyl or hydrogen;

W is oxygen;

X is a bond, oxygen or sulphur, where the bond originating from an oxygen or sulphur atom leads to a saturated C atom of group Z or to $R^1$, or a group >CH—$R^5$, >CHOR$^6$, —O—CO—, >CO, >C=NOR$^7$, —O—CHR$^5$— or —O—CHR$^5$—CO—NR$^6$—;

Z is $C_{1-6}$alkylene, $C_{2-8}$alkenylene, hydroxy-$C_{1-6}$alkylidene, —O—, —S—, —O-alk-, —S-alk-, -alk-O—, -alk-S— or -alk-NR$^6$—, where alk is $C_{1-6}$alkylene; and where (a) if Z is —O-alk- or —S-alk-, then X is —CHR$^5$—; and (b) if X is a bond, then Z is $C_{2-8}$alkenylene, -alk-O— or -alk-S—;

n is 1 or, if X is —O—CO— or —O—CHR$^5$—CO—NR$^6$—, 0 or 1;

and its salt or compound in which one or more atoms are replaced by their stable, nonradioactive isotopes, especially pharmaceutically acceptable salt.

2. A compound according to claim 1, which corresponds to the formula (IA)

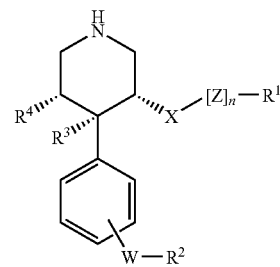

(IA)

in which $R^1$, $R^2$, $R^3$, $R^4$, W, X, Z and n have the meaning stated for the compound of the formula (I) in claim 1.

3. A compound according to claim 1, wherein $R^1$ is 3,4-dihydro-2H-benzo[1,4]oxazinyl substituted by halogen-, oxide-, oxo-, $C_{1-6}$alkoxy-, $C_{1-6}$alkoxy-$C_{1-6}$alkoxy-, $C_{1-6}$alkoxy-$C_{1-6}$alkyl-, $C_{1-6}$alkoxycarbonylamino-$C_{1-6}$alkoxy-, $C_{1-6}$alkoxycarbonylamino-$C_{1-6}$alkyl-, $C_{1-6}$alkyl-, $C_{0-6}$alkylcarbonylamino-$C_{1-6}$alkoxy-, $C_{0-6}$alkylcarbonylamino-$C_{1-6}$alkyl-, $C_{1-6}$alkoxy-$C_{1-6}$alkoxy-$C_{1-6}$alkyl-, cyano-$C_{1-6}$alkoxy-, cyano-$C_{1-6}$alkyl- or trifluoromethyl.

4. A compound according to claim 1, where X is oxygen, sulphur, —O—CHR$^5$—, —O—CHR$^5$—CO—NR$^6$— or —CO— and Z is methylene or -alk-O—.

5. A compound according to claim 1, wherein $R^2$ in the meaning of a heterocyclyl linked via a C atom is a radical selected from pyridyl, pyrimidinyl, pyrazinyl, benzo[b]thienyl, quinolyl, isoquinolyl, quinoxalinyl, indolyl, 3,4-dihydro-2H-benzo[1,4]oxazinyl, 2,3-dihydrobenzofuranyl and benzofuranyl.

6. A method for the treatment of high blood pressure, glaucoma, myocardial infarction, restenoses or stroke, where a therapeutically effective amount of a compound of the formula (I) according to claim 1 is administered to a patient in need thereof.

7. A pharmaceutical product comprising a compound of the formula (I) according to claim 1, and usual excipients.

8. A pharmaceutical combination in the form of a product or of a kit composed of individual components consisting a) of a compound of the formula (I) according to claim 1, and b) at least one pharmaceutical form whose active ingredient has a cardiovascular effect.

9. A compound according to claim 2, wherein $R^1$ is 3,4-dihydro-2H-benzo[1,4]oxazinyl substituted by halogen-, oxide-, oxo-, $C_{1-6}$alkoxy-, $C_{1-6}$alkoxy-$C_{1-6}$alkoxy-, $C_{1-6}$alkoxy-$C_{1-6}$alkyl-, $C_{1-6}$alkoxycarbonylamino-$C_{1-6}$alkoxy-, $C_{1-6}$alkoxycarbonylamino-$C_{1-6}$alkyl-, $C_{1-6}$alkyl-, $C_{0-6}$alkylcarbonylamino-$C_{1-6}$alkoxy-, $C_{0-6}$alkylcarbonylamino-$C_{1-6}$alkyl-, $C_{1-6}$alkoxy-$C_{1-6}$alkoxy-$C_{1-6}$alkyl-, cyano-$C_{1-6}$alkoxy-, cyano-$C_{1-6}$alkyl- or trifluoromethyl.

10. A compound according to claim 2, where X is oxygen, sulphur, —O—CHR$^5$—, —O—CHR$^5$—CO—NR$^6$— or —CO— and Z is methylene or -alk-O—.

11. A compound according to claim 2, wherein $R^2$ in the meaning of a heterocyclyl linked via a C atom is a radical selected from pyridyl, pyrimidinyl, pyrazinyl, benzo[b]thienyl, quinolyl, isoquinolyl, quinoxalinyl, indolyl, 3,4-dihydro-2H-benzo[1,4]oxazinyl, 2,3-dihydrobenzofuranyl and benzofuranyl.

12. A method for the treatment of high blood pressure, glaucoma, myocardial infarction, restenoses or stroke, where a therapeutically effective amount of a compound of the formula (IA) according to claim 2 is administered to a patient in need thereof.

13. A pharmaceutical product comprising a compound of the formula (IA) according to claim 2, and usual excipients.

14. A pharmaceutical combination in the form of a product or of a kit composed of individual components consisting a) of a compound of the formula (IA) according to claim 2, and b) at least one pharmaceutical form whose active ingredient has a cardiovascular effect.

* * * * *